(12) United States Patent
Ding et al.

(10) Patent No.: US 8,008,483 B2
(45) Date of Patent: Aug. 30, 2011

(54) sEH INHIBITORS AND THEIR USE

(75) Inventors: Yun Ding, Waltham, MA (US); Reema K. Thalji, Collegeville, PA (US); Joseph P. Marino, Jr., King of Prussia, PA (US)

(73) Assignee: Glaxosmithkline, LLC, Philadelphia, PA (US)

( * ) Notice: Subject to any disclaimer, the term of this patent is extended or adjusted under 35 U.S.C. 154(b) by 0 days.

(21) Appl. No.: 12/682,077

(22) PCT Filed: Oct. 10, 2008

(86) PCT No.: PCT/US2008/079525
§ 371 (c)(1),
(2), (4) Date: Apr. 8, 2010

(87) PCT Pub. No.: WO2009/049165
PCT Pub. Date: Apr. 16, 2009

(65) Prior Publication Data
US 2010/0210628 A1 Aug. 19, 2010

Related U.S. Application Data

(60) Provisional application No. 60/979,164, filed on Oct. 11, 2007.

(51) Int. Cl.
| | | |
|---|---|---|
| C07D 401/12 | (2006.01) | |
| C07D 401/14 | (2006.01) | |
| C07D 403/12 | (2006.01) | |
| C07D 403/14 | (2006.01) | |
| A61K 31/53 | (2006.01) | |
| A61P 9/08 | (2006.01) | |
| A61P 9/10 | (2006.01) | |
| A61P 9/12 | (2006.01) | |
| A61P 11/06 | (2006.01) | |
| A61P 11/00 | (2006.01) | |
| A61P 13/12 | (2006.01) | |
| A61P 1/16 | (2006.01) | |

(52) U.S. Cl. ........ 544/197; 544/198; 544/208; 544/209; 514/245

(58) Field of Classification Search .................. 544/197, 544/198, 208, 209; 514/245
See application file for complete search history.

(56) References Cited

U.S. PATENT DOCUMENTS
| | | |
|---|---|---|
| 2004/0029902 A1 | 2/2004 | Singh et al. |
| 2006/0194803 A1 | 8/2006 | Kubota et al. |
| 2007/0225283 A1 | 9/2007 | Hammock et al. |

FOREIGN PATENT DOCUMENTS
| | | |
|---|---|---|
| EP | 1464335 | 10/2004 |
| WO | WO 2005/028467 | 3/2005 |
| WO | WO2008/105968 | 9/2008 |
| WO | WO2009/049154 | 4/2009 |
| WO | WO2009049157 A1 | 4/2009 |

OTHER PUBLICATIONS

Dorrance, Phd., et al.: "An Epoxide Hydrolase Inhibitor, 12-(3-Adamantan-1-Yl-Ureido)Dodecanoic Acid (AUDA), Reduces Ischemic Cerebral Infact Size In Stroke-Prone Spontaneously Hypertensive Rats" Journal of Cardiovascular Pharmacology, Dec. 2005, vol. 46, No. 6, pp. 842-848.

Fornage, et al.: "The Soluble Epoxide Hydrolase Gene Harbors Sequence Variation Associated With Susceptibility To And Protection From Incident Ischemic Stroke" Human Molecular Genetics, 2005, vol. 14, No. 19, pp. 2829-2837.

Fretland, et al.: "Epoxide Hydrolases: Biochemistry and Molecular Biology", Chemico-Biological Interactions. 2000; vol. 129, pp. 41-59.

Imig, et al.: "Soluble Epoxide Hydrolase Inhibition Lowers Arterial Blood Pressure in Angiotensin II Hypertension" Hypertension. 2002; vol. 39 (Part 2), pp. 690-694.

Imig, et al.: "An Orally Active Epoxide Hydrolase Inhibitor Lowers Blood Pressure and Provides Renal Protection In Salt-Sensitive Hypertension" Hypertension. 2005; vol. 46 (Part 2): pp. 975-981.

Imig, et al.: "Cardiovascular Therapeutic Aspects of Soluble Epoxide Hydrolase Inhibitors" Cardiovascular Drug Reviews. 2006; vol. 24, No. 2, pp. 169-188.

Inceoglu, et al.: "Inhibition Of Soluble Epoxide Hydrolase Reduces LPS-Induced Thermal Hyperalgesia And Mechanical Allodynia In A Rat Model Of Inflammatory Pain" Life Sciences. 2006; vol. 79, pp. 2311-2319.

(Continued)

Primary Examiner — Venkataraman Balasubramanian
(74) Attorney, Agent, or Firm — Linda E. Hall; John Lemanowicz

(57) ABSTRACT

The invention is directed to novel sEH inhibitors and their use in the treatment of diseases mediated by the sEH enzyme. Specifically, the invention is directed to compounds according to Formula I:

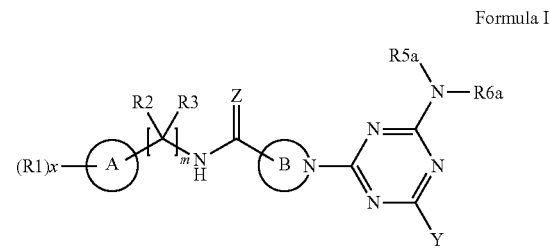

Formula I wherein R1, R2, R3, R5a, R6a A, B, Y, x, and m are defined below, and to pharmaceutically-acceptable salts thereof. The compounds of the invention are sEH inhibitors and can be used in the treatment of diseases mediated by the sEH enzyme, such as hypertension. Accordingly, the invention is further directed to pharmaceutical compositions comprising a compound of the invention. The invention is still further directed to methods of inhibiting sEH and treatment of conditions associated therewith using a compound of the invention or a pharmaceutical composition comprising a compound of the invention.

16 Claims, No Drawings

OTHER PUBLICATIONS

Jones, P.D. et al.: "Synthesis And SAR Of Conformationally Restricted Inhibitors Of Soluble Epoxide Hydrolase" Bioorganic & Medicinal Chemistry Letters, Oct. 1, 2009, vol. 16, No. 19, pp. 5212-5216.

Jung, et al.: "Soluble Epoxide Hydrolase Is A Main Effector Of Angiotensin II-Induced Hypertension" Hypertension. 2005; vol. 45 (Part 2), pp. 759-765.

Koerner, et al.: "Polymorphisms In The Human Soluble Epoxide Hydrolase Gene *EPHX2* Linked To Neuronal Survival After Ischemic Injury" The Journal of Neuroscience. Apr. 25, 2007; vol. 27, No. 17, pp. 4642-4649.

Krotz, et al.: "Membrane Potential-Dependent Inhibition Of Platelet Adhesion To Endothelial Cells By Epoxyeicosatrienoic Acids" Arterioscler Thrombosis Vascular Biology. 2004; vol. 24, pp. 595-600.

Lee, et al.: "Genetic Variation in Soluble Epoxide Hydrolase (*EPHX2*) And Risk Of Coronary Heart Disease: The Atherosclerosis Risk In Communities (ARIC) Study" Human Molecular Genetics. 2006; vol. 15, No. 10, pp. 1640-1649.

Loch, et al.: "Prevention of Hypertension In DOCA-Salt Rats By An Inhibitor Of Soluble Epoxide Hydrolase" Cell Biochemistry and Biophysics. 2007; vol. 47, pp. 87-97.

Sato, et al.: "Soluble Epoxide Hydrolase Variant (Glu287Arg) Modifies Plasma Total Cholesterol and Triglyceride Phenotype in Familial Hypercholesterolemia: Intrafamilial Association Study In An Eight-Generation Hyerlipidemic Kindred" Journal Of Human Genetics. 2004; vol. 49, pp. 29-34.

Sinal, et al.: "Targeted Disruption Of Soluble Epoxide Hydrolase Reveals A Role In Blood Pressure Regulation" The Journal Of Biological Chemistry. 2000; vol. 275, No. 51, pp. 40504-40510.

Spector, et al.: "Epoxyeicosatrienoic Acids (Eets): Metabolism And Biochemical Function" Progress In Lipid Research. 2004; vol. 43, pp. 55-90.

Wei, et al.: "Sequence Variation In The Soluble Epoxide Hydrolase Gene And Subclinical Coronary Atherosclerosis: Interaction With Cigarette Smoking" Atherosclerosis. 2007; vol. 190, pp. 26-34.

Xu, et al.: "Prevention And Reversal Of Cardiac Hypertrophy By Soluble Epoxide Hydrolase Inhibitors" Proceedings National Academy Of Sciences. 2006; vol. 103, No. 49, pp. 18733-18738.

Zhao, et al.: "Soluble Epoxide Hydrolase Inhibition Protects the Kidney from Hypertension-Induced Damage" Journal of the American Society of Nephrology, 2004, vol. 15, pp. 1244-1253.

SEH INHIBITORS AND THEIR USE

This application is a 371 of International Application No. PCT/US2008/079525, filed 10 Oct. 2008, which claims the benefit of U.S. Provisional Application No. 60/979,164, filed 11 Oct. 2007, which are incorporated herein in their entirety.

FIELD OF THE INVENTION

The invention is directed to novel sEH inhibitors and their use in the treatment of diseases mediated by the sEH enzyme.

BACKGROUND OF THE INVENTION

Epoxide functional groups may be found in drugs, xenobiotic materials, and endogenous biomolecules. Epoxide hydrolases, found in both plants and animals, are enzymes that convert epoxides to diols by hydrolysis. In mammals, soluble epoxide hydrolase ("sEH") is primarily responsible for the metabolism of arachidonic acid derivatives known as epoxyeicosatrienoic acids ("EETs"). sEH converts EETs into dihydroxyeicosatrienoic acids ("DHETs"). Several publications have described the beneficial vasodilatory, anti-inflamatory, and anti-thrombotic effects of EETs. See E.g. Spector et al., *Prog. Lipid Res.*, 43, 55-90, 2004; Imig, *Cardiovasc. Drug Rev.*, 24, 169-188, 2006. DHETs are generally inactive and thus do not exhibit the beneficial effects of EETs.

Conversely, microsomal epoxide hydrolase ("mEH") catalyzes the hydrolysis of a broad range of epoxide substrates including carcinogenic polycyclic aromatic hydrocarbons and reactive epoxides, thus it provides an important detoxification pathway. Polymorphisms in mEH may lead to differences in bioactivation of pro-carcinogens and several human epidemiological studies suggest that mEH genotype is associated with altered cancer risk. Fretland & Omiecinski, *Chemico-Biol. Int.*, 129, 41-59, 2000.

Pharmacological, knockout mouse phenotype and genetic polymorphism studies suggest that elevated EET levels are protective in numerous cardiovascular disorders including hypertension [Sinal et al., *J. Biol. Chem.*, 275, 40504-40510, 2000; Imig et al., *Hypertension*, 39, 690-694, 2002; Jung et al., *Hypertension*, 45, 759-765, 2005; Loch et al., *Cell Biochem Biophys.*, 47, 87-98, 2007], heart failure [Xu et al., *Proc. Natl. Acad. Sci. U.S.A.*, 103, 18733-18738, 2006], renal dysfunction/end organ damage [Zhao et al., *J. Am. Soc. Nephrol.*, 15; 1244-1253, 2004; Imig et al., *Hypertension*, 46; 975-981, 2005], stroke [Dorrance et al., *J. Cardiovasc. Pharmacol.*, 46; 842-848, 2005; Fornage et al., *Hum. Mol. Genet.*, 14; 2829-2837, 2005; Koerner et al., *J. Neurosci.*, 27; 4642-4649, 2007], atherosclerosis and thrombosis [Sato et al., *J. Hum. Genet.*, 49; 29-34, 2004; Lee et al., *Hum Mol Genet.*, 15; 1640-1649, 2006; Wei et al., *Atherosclerosis*, 190; 26-34, 2007; Krotz et al., *Arterioscler. Thromb. Vasc. Biol.*, 24; 595-600, 2004] and inflammation [Inceoglu et al., *Life Sci.*, 79; 2311-2319, 2006].

One approach to the treatment of such conditions designed to take advantage of the beneficial effect of EETs has been to inhibit the action of sEH thereby preventing EET degradation. In light of the role sEH plays in the degradation of EETs, it is desirable to prepare compounds that inhibit its activity. Thus, there is a need to identify compounds that inhibit sEH, which can be used in the treatment of a variety of conditions mediated by the sEH enzyme.

SUMMARY OF THE INVENTION

The invention is directed to novel sEH inhibitors and their use in the treatment of diseases mediated by the sEH enzyme. Specifically, the invention is directed to compounds according to Formula I:

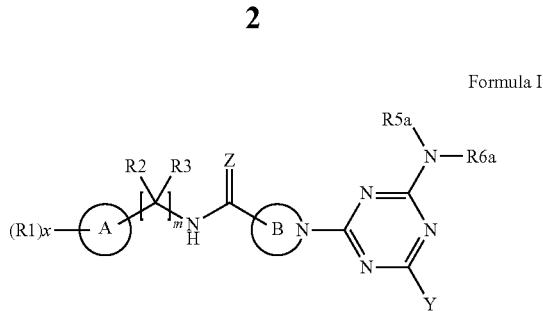

Formula I wherein R1, R2, R3, R5a, R6a A, B, Y, Z, x, and m are defined below, and to pharmaceutically-acceptable salts thereof.

The compounds of the invention are sEH inhibitors and can be used in the treatment of diseases mediated by the sEH enzyme, such as hypertension. Accordingly, the invention is further directed to pharmaceutical compositions comprising a compound of the invention. The invention is still further directed to methods of inhibiting sEH and treatment of conditions associated therewith using a compound of the invention or a pharmaceutical composition comprising a compound of the invention.

DETAILED DESCRIPTION OF THE INVENTION

In describing the invention, chemical elements are identified in accordance with the Periodic Table of the Elements. Abbreviations and symbols utilized herein are in accordance with the common usage of such abbreviations and symbols by those skilled in the chemical and biological arts. For example, the following abbreviations are used herein:

"aq" is an abbreviation for aqueous
"BOP" is an abbreviation for (Benzotriazol-1-yloxy)tris (dimethylamino)phosphonium hexafluorophosphate
"° C." is an abbreviation for degrees Celsius
"DIEA" is an abbreviation for di-isopropylethylamine
"DMAP" is an abbreviation for dimethylaminopyridine
"DMF" is an abbreviation for dimethylformamide
"DMSO" is an abbreviation for Dimethylsulfoxide
"EDCI" is an abbreviation for N-(3-Dimethylaminopropyl)-N'-ethylcarbodiimide hydrochloride
"equiv" is an abbreviation for equivalent
"HOBT" is an abbreviation for 1-Hydroxybenzotriazole
"HPLC" is an abbreviation for High Pressure Liquid Chromatography
"g" is an abbreviation for gram or grams
"L" is an abbreviation for liter or liters
"LC-MS" is an abbreviation for Liquid chromatography-Mass spectrometry
"mL" is an abbreviation for milliliter or milliliters
"min" is an abbreviation for minute or minutes
"mmol" is an abbreviation for millimole or millimolar
"N" is an abbreviation for Normal and refers to the number of equivalents of reagent per liter of solution
"Ph" is an abbreviation for phenyl
"sat" is an abbreviation for saturated
"TFA" is an abbreviation for trifluoroacetic acid
"THF" is an abbreviation for tetrahydrofuran

TERMS AND DEFINITIONS

"Alkyl" refers to a monovalent saturated hydrocarbon chain having the specified number of member atoms. For example, C1-C8 alkyl refers to an alkyl group having from 1 to 8 member atoms. Alkyl groups may be optionally substituted with one or more substituents as defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Cycloalkyl" refers to a monovalent saturated or unsaturated hydrocarbon ring having the specified number of member atoms. For example, C3-C6 cycloalkyl refers to a cycloalkyl group having from 3 to 6 member atoms. Unsaturated Cycloalkyl groups have one or more carbon-carbon double bonds within the ring. Cycloalkyl groups are not aromatic. Cycloalkyl groups having from 3 to 7 member atoms or less are monocyclic ring systems. Cycloalkyl groups having at least 7 member atoms may be monocyclic, bridged or fused bicyclic ring systems. Cycloalkyl groups may be optionally substituted with one or more substituents as defined herein. Cycloalkyl includes cyclopropyl, cyclopropenyl, cyclobutyl, cyclobutenyl, cyclopentyl, cyclopentenyl, cyclohexyl, cyclohexenyl, cycloheptanyl, and cycloheptenyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" refers to the time required for half of a quantity of a substance to be converted to another chemically distinct specie in vitro or in vivo.

"Halo" refers to the halogen radical fluoro, chloro, bromo, or iodo.

"Haloalkyl" refers to an alkyl group that is substituted with one or more halo substituents. Haloalkyl includes trifluoromethyl.

"Heteroaryl" refers to a monovalent aromatic ring containing from 1 to 4 heteroatoms as member atoms in the ring. Heteroaryl groups containing more than one heteroatom may contain different heteroatoms. Heteroaryl groups may be optionally substituted with one or more substituents as defined herein. Unless otherwise specified, heteroaryl groups are monocyclic ring systems or are fused, spiro, or bridged bicyclic ring systems. Monocyclic heteroaryl rings have 5 or 6 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, tetrazolyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, and napthyridinyl.

"Heteroatom" refers to a nitrogen, sulphur, or oxygen atom.

"Heterocycloalkyl" refers to a saturated or unsaturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituent as defined herein. Unless otherwise specified, heterocycloalkyl groups are monocyclic, bridged, or fused ring systems. Monocyclic heterocycloalkyl rings have from 4 to 7 member atoms. Bridged or bicyclic heterocycloalkyl rings have from 7 to 11 member atoms. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, azepinyl, 1,3-dioxolanyl, 1,3-dioxanyl, 1,4-dioxanyl, 1,3-oxathiolanyl, 1,3-oxathianyl, 1,3-dithianyl, azetidinyl, azabicylo[3.2.1]octyl, azabicylo[3.3.1]nonyl, azabicylo[4.3.0]nonyl, oxabicylo[2.2.1]heptyl, and phthalimidyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted or substituted with one or more substituents as defined herein. "Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Compounds

The invention is directed to compounds according to Formula I:

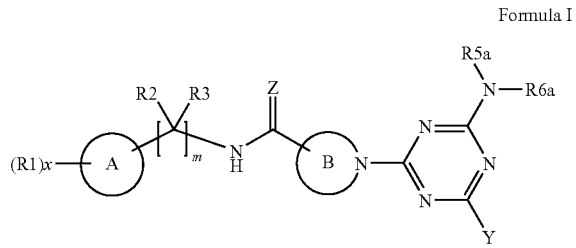

Formula I wherein:
A is phenyl, monocyclic heteroaryl, or C5-C6 cycloalkyl;
when A is phenyl or monocyclic heteroaryl each R1 is independently selected from the group consisting of:

halo, CN, Ra, ORb, C(O)ORc, C(O)NRcRc, NRcRc, NRcC(O)Rb, NRcS(O₂)Ra, SRb, S(O₂)Ra, and S(O₂)NRcRc;

when A is C5-C6 cycloalkyl each R1 is independently selected from the group consisting of: Ra, ORb, C(O)ORc, C(O)NRcRc, NRcRc, and NRcC(O)Rb;

x is an integer from 0 to 5;
R2 is H;
R3 is H;
m is 1 or 2;
Z is O or S;
B is B1, B2, B3, B4, or B5;
B1 is

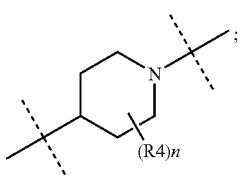

B2 is

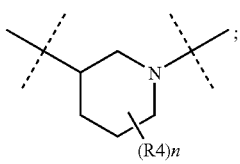

B3 is

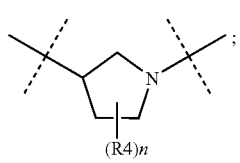

B4 is

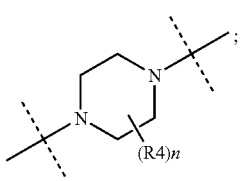

B5 is

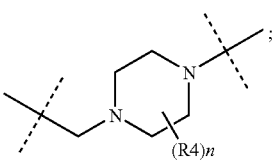

each R4 is independently C1-C3 alkyl;
n is an integer from 0 to 4;
Y is H, OH, R7, R8, R9, R10, R11, R12, or NR5bR6b;

R5a and R5b are each independently H, R51, R52, R53, R54, R55, —C(O)Rb, —C(O)NRcRc, —S(O₂)Ra, or —S(O₂)NRcRc;

each R51 is C1-C6 alkyl optionally substituted with one or more substituents selected from the group consisting of: halo, ORd, SRd, C(O)ORc, C(O)NReRe, NReRe, Rg, Rh, Ri, Rj;

each R52 is C3-C6 cycloalkyl optionally substituted with one or more substituents selected from the group consisting of: halo, ORd, SRd, C(O)ORc, C(O)NReRe, NReRe, C1-C3 alkyl, and C1-C3 haloalkyl;

R53 is monocyclic heterocycloalkyl optionally substituted with one or more C1-C3 alkyl;

R54 is phenyl optionally substituted with one or more substituents selected from the group consisting of: halo, CN, Ra, ORb, C(O)ORc, C(O)NRcRc, NRcRc, NRcC(O)Rb, NRcS(O₂)Ra, SRb, S(O₂)Ra, and S(O₂)NReRe;

R55 is monocyclic heteroaryl optionally substituted with one or more substituents selected from the group consisting of: halo, —CN, C1-C3 alkyl, C1-C3 haloalkyl, ORd, and NReRe;

R6a and R6b are each independently H, R51, or R52; or

R5a and R6a and/or R5b and R6b, independently in each instance, taken together with the nitrogen atom to which they are attached form a saturated monocyclic ring having from 5 to 7 member atoms wherein said ring optionally contains one additional heteroatom as a member atom and wherein said ring is optionally substituted with one or more substituents selected from the group consisting of: C1-C3 alkyl, ORd, and NRfRf;

R7 is C1-C8 alkyl optionally substituted with one or more substituents selected from the group consisting of: halo, ORd, SRd, NReRe, C3-C6 cycloalkyl, Ri, and Rj;

R8 is C3-C6 cycloalkyl optionally substituted with one or more substituents selected from the group consisting of: halo, ORd, SRd, NReRe, C1-C3 alkyl, and C1-C3 haloalkyl;

R9 monocyclic heterocycloalkyl optionally substituted with one or more C1-C3 alkyl;

R10 is phenyl optionally substituted with one or more substituents selected from the group consisting of: halo, CN, Ra, ORb, C(O)ORc, C(O)NReRe, NReRe, NRcC(O)Rb, NRcS(O₂)Ra, SRb, S(O₂)Ra, and S(O₂)NRcRc R11 is heteroaryl optionally substituted with one or more substituents selected from the group consisting of: halo, CN, Ra, ORb, C(O)ORc, C(O)NReRe, NReRe, NRcC(O)Rb, NRcS(O₂)Ra, SRb, S(O₂)Ra, and S(O₂)NRcRc;

R12 is —OR7, —OR8, —OR9, —OR10, —OR11, —SR7, —SR8, —SR9, —SR10, or SR11;

each Ra is independently C1-C6 alkyl or C1-C6 haloalkyl;
each Rb is independently H, C1-C6 alkyl or C1-C6 haloalkyl;
each Rc is independently H or C1-C6 alkyl;
where there are two Rc groups attached to a nitrogen;
both Rc groups, independently in each instance, taken together with the nitrogen atom to which they are attached form a saturated monocyclic ring having from 5 to 7 member atoms wherein said ring optionally contains one additional heteroatom as a member atom and wherein said ring is optionally substituted with one or more substituents selected from the group consisting of: C1-C3 alkyl, ORd, and NRfRf;

each Rd is independently H, C1-C3 alkyl or C1-C3 haloalkyl;

each Re is independently H, C1-C3 alkyl, CH₂—CF₃; or
both Re groups, independently in each instance, taken together with the nitrogen atom to which they are attached form a saturated monocyclic ring having from 5 to 7 member atoms wherein said ring optionally contains one additional heteroatom as a member atom and wherein said ring is optionally substituted with one or more substituents selected from the group consisting of: C1-C3 alkyl, ORd, and NRfRf;

each Rf is independently H or C1-C3 alkyl.

each Rg is C3-C6 cycloalkyl optionally substituted with one or more substituents selected from the group consisting of: halo, ORd, SRd, C(O)ORc, C(O)NReRe, NReRe, and C1-C3 alkyl;

each Rh is monocyclic heterocycloalkyl optionally substituted with one or more C1-C3 alkyl;

each Ri is phenyl optionally substituted with one or more substituents selected from the group consisting of: halo, —CN, C1-C3 alkyl, C1-C3 haloalkyl, ORd, and NReRe;

each Rj is monocyclic heteroaryl optionally substituted with one or more substituents selected from the group consisting of: halo, —CN, C1-C3 alkyl, C1-C3 haloalkyl, ORd, and NReRe; and each Rk is independently H, C1-C3 alkyl, C1-C3 haloalkyl, or benzyl optionally substituted with one or more substituents selected from the group consisting of: halo, —CN, C1-C3 alkyl, C1-C3 haloalkyl, ORd, and NReRe.

The meaning of any functional group or substituent thereon at any one occurrence in Formula I, or any subformula thereof, is independent of its meaning, or any other functional group's or substituent's meaning, at any other occurrence, unless stated otherwise.

The compounds according to Formula I may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass any stereoisomer and all mixtures thereof. Thus, compounds according to Formula I containing one or more chiral center may be used as racemic mixtures, enantiomerically enriched mixtures, or as enantiomerically pure individual stereoisomers.

Individual stereoisomers of a compound according to Formula I which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof. Likewise, all tautomeric forms are also included in Formula I whether such tautomers exist in equilibrium or predominately in one form.

In certain embodiments, compounds according to Formula I may contain an acidic functional group and are therefore capable of forming pharmaceutically-acceptable base addition salts by treatment with a suitable base. In certain other embodiments, compounds according to Formula I may contain a basic functional group and are therefore capable of forming pharmaceutically-acceptable acid addition salts by treatment with a suitable acid. Thus, the skilled artisan will appreciate that pharmaceutically-acceptable salts of the compounds according to Formula I may be prepared. Indeed, in certain embodiments of the invention, pharmaceutically-acceptable salts of the compounds according to Formula I may be preferred over the respective free base or free acid because such salts impart greater stability or solubility to the molecule thereby facilitating formulation into a dosage form. Accordingly, the invention is further directed to pharmaceutically-acceptable salts of the compounds according to Formula.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

Because of their potential use in medicine, the salts of the compounds of formula (I) are preferably pharmaceutically acceptable. Suitable pharmaceutically acceptable salts can include acid or base addition salts.

A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

A pharmaceutically acceptable base addition salt can be formed by reaction of a compound of formula (I) with a suitable inorganic or organic base (e.g. triethylamine, ethanolamine, triethanolamine, choline, arginine, lysine or histidine), optionally in a suitable solvent such as an organic solvent, to give the base addition salt which is usually isolated for example by crystallisation and filtration.

Other suitable pharmaceutically acceptable salts include pharmaceutically acceptable metal salts, for example pharmaceutically acceptable alkali-metal or alkaline-earth-metal salts such as sodium, potassium, calcium or magnesium salts; in particular pharmaceutically acceptable metal salts of one or more carboxylic acid moieties that may be present in the compound of formula (I).

Other non-pharmaceutically acceptable salts, e.g. oxalates, may be used, for example in the isolation of compounds of the invention, and are included within the scope of this invention.

The invention includes within its scope all possible stoichiometric and non-stoichiometric forms of the salts of the compounds of formula (I).

As used herein, the term "compounds of the invention" means both the compounds according to Formula I and the pharmaceutically-acceptable salts thereof. The term "a compound of the invention" also appears herein and refers to both a compound according to Formula I and its pharmaceutically-acceptable salts.

In the solid state, compounds of the invention can exist in crystalline, semi-crystalline and amorphous forms, as well as mixtures thereof. The skilled artisan will appreciate that pharmaceutically-acceptable solvates of a compound of the invention may be formed wherein solvent molecules are incorporated into the solid-state structure during crystallization. Solvates may involve water or nonaqueous solvents, or mixtures thereof. In addition, the solvent content of such solvates can vary in response to environment and upon storage. For example, water may displace another solvent over time depending on relative humidity and temperature.

Solvates wherein water is the solvent that is incorporated into the solid-state structure are typically referred to as "hydrates." Solvates wherein more than one solvent is incorporated into the solid-state structure are typically referred to as "mixed solvates". Solvates include "stoichiometric solvates" as well as compositions containing variable amounts of solvent (referred to as "non-stoichiometric solvates"). Stoichiometric solvates wherein water is the solvent that is incorporated into the solid-state structure are typically referred to as "stoichiometric hydrates", and non-stoichiometric solvates wherein water is the solvent that is incorporated into the solid-state structure are typically referred to as "non-stoichiometric hydrates". The invention includes both stoichiometric and non-stoichiometric solvates.

In addition, crystalline forms of a compound of the invention, including solvates thereof, may contain solvent molecules, which are not incorporated into the solid-state structure. For example, solvent molecules may become trapped in the crystals upon isolation. In addition, solvent molecules may be retained on the surface of the crystals. The invention includes such forms.

The skilled artisan will further appreciate that compounds of the invention, including solvates thereof, may exhibit polymorphism (i.e. the capacity to occur in different crystalline packing arrangements). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different IR spectra and X-ray powder diffraction patterns, which may be used for identification. Polymorphs may also exhibit different melting points, which may be used for identification. The skilled artisan will appreciate that different polymorphs may be produced, for example, by changing or adjusting the reaction conditions or reagents, used in making the compound. For example, changes in temperature, pressure, or solvent may result in the production of different polymorphs. In addition, one polymorph may spontaneously convert to another polymorph under certain conditions.

Representative Embodiments

In one embodiment:
A is phenyl, thiophenyl, or pyridyl;
R1 is $CF_3$, halo, $OCF_3$, CN, $OC_1$-$C_6$ alkyl, morpholino, $CO_2H$, or $N(CH_3)_2$;
x is 1, 2, or 3;
B is B1, B2 or B3;
n is 0;
Z is O;
Y is C1-C3 alkyl, phenyl, thiophenyl, or pyridyl; wherein the phenyl, thiophenyl or pyridyl may be substituted by —$CO_2H$, $SO_2Me$, $CF_3$, halo, or CN;
R5a is hydrogen or C1-C6 alkyl; and
R6a is hydrogen or C1-C6 alkyl;
or a pharmaceutically acceptable salt thereof.
In another embodiment:
A is phenyl;
R1 is $CF_3$, halo, $OCF_3$, CN, $OC_1$-$C_6$ alkyl, or morpholino;
x is 1, or 2;
B is B1;
n is 0
Z is O;
Y is methyl;
R5a is hydrogen; and
R6a is methyl;
or a pharmaceutically acceptable salt thereof.

Specific examples of compounds of the present invention include the following:
1-(4-(Methylamino)-6-{[(2R)-2-phenylpropyl]amino}-1,3,5-triazin-2-yl)-N-{[2-(trifluoromethyl)phenyl]methyl}-4-piperidinecarboxamide;

1-[4-[[2-(Dimethylamino)ethyl](methyl)amino]-6-(methylamino)-1,3,5-triazin-2-yl]-N-{[2-(trifluoromethyl)phenyl]methyl}-4-piperidinecarboxamide;

1-[4-[(1,1-Dimethylethyl)amino]-6-(4-methyl-1-piperazinyl)-1,3,5-triazin-2-yl]-N-{[2-(trifluoromethyl)phenyl]methyl}-4-piperidinecarboxamide;

1-[4-(Methylamino)-6-(4-methyl-1-piperazinyl)-1,3,5-triazin-2-yl]-N-{[2-(trifluoromethyl)phenyl]methyl}-4-piperidinecarboxamide;

1-[4-{[2-(Dimethylamino)ethyl]amino}-6-(methylamino)-1,3,5-triazin-2-yl]-N-{[2-(trifluoromethyl)phenyl]methyl}-4-piperidinecarboxamide;

N-[2-(1-Cyclohexen-1-yl)ethyl]-1-(4-(methylamino)-6-{[(2R)-2-phenylpropyl]amino}-1,3,5-triazin-2-yl)-4-piperidinecarboxamide;

1-[4-(Methylamino)-6-(4-pyridinylamino)-1,3,5-triazin-2-yl]-N-{[2-(trifluoromethyl)phenyl]methyl}-4-piperidinecarboxamide;

1-[4-(Methylamino)-6-(1-piperazinyl)-1,3,5-triazin-2-yl]-N-{[2-(trifluoromethyl)phenyl]methyl}-4-piperidinecarboxamide;

1-[4-Amino-6-(4-methyl-1-piperazinyl)-1,3,5-triazin-2-yl]-N-{[2-(trifluoromethyl)phenyl]methyl}-4-piperidinecarboxamide;

1-[4-(Methylamino)-1,3,5-triazin-2-yl]-N-{[2-(trifluoromethyl)phenyl]methyl}-4-piperidinecarboxamide;

1-(4-{[(2R)-2-Phenylpropyl]amino}-1,3,5-triazin-2-yl)-N-{[2-(trifluoromethyl)phenyl]methyl}-4-piperidinecarboxamide;

1-[4-({2-[(Phenylmethyl)thio]ethyl}amino)-1,3,5-triazin-2-yl]-N-{[2-(trifluoromethyl)phenyl]methyl}-4-piperidinecarboxamide;

1-[4-(4-Methyl-1-piperazinyl)-1,3,5-triazin-2-yl]-N-{[2-(trifluoromethyl)phenyl]methyl}-4-piperidinecarboxamide;

1-[4-(4-Morpholinyl)-1,3,5-triazin-2-yl]-N-{[2-(trifluoromethyl)phenyl]methyl}-4-piperidinecarboxamide;

1-[4,6-Bis(4-methyl-1-piperazinyl)-1,3,5-triazin-2-yl]-N-{[2-(trifluoromethyl)phenyl]methyl}-4-piperidinecarboxamide;

1-(4,6-Bis{[(2R)-2-phenylpropyl]amino}-1,3,5-triazin-2-yl)-N-{[2-(trifluoromethyl)phenyl]methyl}-4-piperidinecarboxamide;

1-{4,6-Bis[[2-(dimethylamino)ethyl](methyl)amino]-1,3,5-triazin-2-yl}-N-{[2-(trifluoromethyl)phenyl]methyl}-4-piperidinecarboxamide;

1-(4,6-Dihexahydro-1H-azepin-1-yl-1,3,5-triazin-2-yl)-N-{[2-(trifluoromethyl)phenyl]methyl}-4-piperidinecarboxamide;

1-[4,6-Bis(methylamino)-1,3,5-triazin-2-yl]-N-{[2-(trifluoromethyl)phenyl]methyl}-4-piperidinecarboxamide;

1-[4-Hydroxy-6-(4-methyl-1-piperazinyl)-1,3,5-triazin-2-yl]-N-{[2-(trifluoromethyl)phenyl]methyl}-4-piperidinecarboxamide;

1-[4-(Methoxy)-6-(4-methyl-1-piperazinyl)-1,3,5-triazin-2-yl]-N-{[2-(trifluoromethyl)phenyl]methyl}-4-piperidinecarboxamide;

1-[4-(4-Methyl-1-piperazinyl)-6-(methylthio)-1,3,5-triazin-2-yl]-N-{[2-(trifluoromethyl)phenyl]methyl}-4-piperidinecarboxamide;

1-[4-[(1-Methylethyl)amino]-6-(4-methyl-1-piperazinyl)-1,3,5-triazin-2-yl]-N-{[2-(trifluoromethyl)phenyl]methyl}-4-piperidinecarboxamide;

N-[(2,4-Dichlorophenyl)methyl]-1-[4-(methylamino)-6-(4-methyl-1-piperazinyl)-1,3,5-triazin-2-yl]-4-piperidinecarboxamide;

1-[4-(Methylamino)-6-(4-methyl-1-piperazinyl)-1,3,5-triazin-2-yl]-N-{[4-(trifluoromethyl)phenyl]methyl}-4-piperidinecarboxamide;

1-[4-(Methylamino)-6-(4-methyl-1-piperazinyl)-1,3,5-triazin-2-yl]-N-({2-[(trifluoromethyl)oxy]phenyl}methyl)-4-piperidinecarboxamide;

N-[(2-Chlorophenyl)methyl]-1-[4-(methylamino)-6-(4-methyl-1-piperazinyl)-1,3,5-triazin-2-yl]-4-piperidinecarboxamide;

N-(Cyclohexylmethyl)-1-[4-(methylamino)-6-(4-methyl-1-piperazinyl)-1,3,5-triazin-2-yl]-4-piperidinecarboxamide;

1-[4-(Methylamino)-6-(4-methyl-1-piperazinyl)-1,3,5-triazin-2-yl]-N-(2-pyridinylmethyl)-4-piperidinecarboxamide;

N-[(2-Trifluoro-phenyl)methyl)-benzyl]-1-[4-(methylamino)-6-(4-methyl-1-piperazinyl)-1,3,5-triazin-2-yl]-3-piperidinecarboxamide;

1-[4-(Methylamino)-6-(4-methyl-1-piperazinyl)-1,3,5-triazin-2-yl]-N-({2-[(trifluoromethyl)oxy]phenyl}methyl)-3-piperidinecarboxamide;

N-[(2,4-Dichlorophenyl)methyl]-1-[4-(methylamino)-6-(4-methyl-1-piperazinyl)-1,3,5-triazin-2-yl]-3-piperidinecarboxamide;

1-[4-(Methylamino)-6-(4-methyl-1-piperazinyl)-1,3,5-triazin-2-yl]-N-{[2-(trifluoromethyl)phenyl]methyl}-3-pyrrolidinecarboxamide;

1-[4-(Methylamino)-6-(4-methyl-1-piperazinyl)-1,3,5-triazin-2-yl]-N-({2-[(trifluoromethyl)oxy]phenyl}methyl)-3-pyrrolidinecarboxamide;

2-{-4-[4-(Methylamino)-6-(4-methyl-1-piperazinyl)-1,3,5-triazin-2-yl]-1-piperazinyl}-N-({2-[(trifluoromethyl)oxy]phenyl}methyl)acetamide;

2-{-4-[4-(Methylamino)-6-(4-methyl-1-piperazinyl)-1,3,5-triazin-2-yl]-1-piperazinyl}-N-{[2-(trifluoromethyl)phenyl]methyl}acetamide;

N-[(2,4-Dichlorophenyl)methyl]-2-{-4-[4-(methylamino)-6-(4-methyl-1-piperazinyl)-1,3,5-triazin-2-yl]-1-piperazinyl}acetamide;

4-[4-(Methylamino)-6-(4-methyl-1-piperazinyl)-1,3,5-triazin-2-yl]-N-{[2-(trifluoromethyl)phenyl]methyl}-1-piperazinecarboxamide;

4-[4-(Methylamino)-6-(4-methyl-1-piperazinyl)-1,3,5-triazin-2-yl]-N-({2-[(trifluoromethyl)oxy]phenyl}methyl)-1-piperazinecarboxamide;

1-[4-(Methylamino)-6-(2-methylphenyl)-1,3,5-triazin-2-yl]-N-{[2-(trifluoromethyl)phenyl]methyl}-4-piperidinecarboxamide;

1-{4-(Methylamino)-6-[4-(trifluoromethyl)phenyl]-1,3,5-triazin-2-yl}-N-{[2-(trifluoromethyl)phenyl]methyl}-4-piperidinecarboxamide;

1-[4-[4-(Acetylamino)phenyl]-6-(methylamino)-1,3,5-triazin-2-yl]-N-{[2-(trifluoromethyl)phenyl]methyl}-4-piperidinecarboxamide;

1-[4-[4-(Dimethylamino)phenyl]-6-(methylamino)-1,3,5-triazin-2-yl]-N-{[2-(trifluoromethyl)phenyl]methyl}-4-piperidinecarboxamide;

1-{4-(Methylamino)-6-[3-(trifluoromethyl)phenyl]-1,3,5-triazin-2-yl}-N-{[2-(trifluoromethyl)phenyl]methyl}-4-piperidinecarboxamide;

1-[4-(2-Chlorophenyl)-6-(methylamino)-1,3,5-triazin-2-yl]-N-{[2-(trifluoromethyl)phenyl]methyl}-4-piperidinecarboxamide;

1-[4-(3-Chlorophenyl)-6-(methylamino)-1,3,5-triazin-2-yl]-N-{[2-(trifluoromethyl)phenyl]methyl}-4-piperidinecarboxamide;

1-[4-(3-Fluorophenyl)-6-(methylamino)-1,3,5-triazin-2-yl]-N-{[2-(trifluoromethyl)phenyl]methyl}-4-piperidinecarboxamide;

1-[4-(4-Fluorophenyl)-6-(methylamino)-1,3,5-triazin-2-yl]-N-{[2-(trifluoromethyl)phenyl]methyl}-4-piperidinecarboxamide;

1-{4-(Methylamino)-6-[2-(methoxy)phenyl]-1,3,5-triazin-2-yl}-N-{[2-(trifluoromethyl)phenyl]methyl}-4-piperidinecarboxamide;

1-[4-[2,4-Bis(methoxy)phenyl]-6-(methylamino)-1,3,5-triazin-2-yl]-N-{[2-(trifluoromethyl)phenyl]methyl}-4-piperidinecarboxamide;

1-[4-(2,6-Dimethylphenyl)-6-(methylamino)-1,3,5-triazin-2-yl]-N-{[2-(trifluoromethyl)phenyl]methyl}-4-piperidinecarboxamide;

1-{4-(Methylamino)-6-[3-(methoxy)phenyl]-1,3,5-triazin-2-yl}-N-{[2-(trifluoromethyl)phenyl]methyl}-4-piperidinecarboxamide;

1-[4-[4-(Ethoxy)phenyl]-6-(methylamino)-1,3,5-triazin-2-yl]-N-{[2-(trifluoromethyl)phenyl]methyl}-4-piperidinecarboxamide;

1-(4-(Methylamino)-6-{3-[(trifluoromethyl)oxy]phenyl}-1,3,5-triazin-2-yl)-N-{[2-(trifluoromethyl)phenyl]methyl}-4-piperidinecarboxamide;

1-(4-(Methylamino)-6-{4-[(trifluoromethyl)oxy]phenyl}-1,3,5-triazin-2-yl)-N-{[2-(trifluoromethyl)phenyl]methyl}-4-piperidinecarboxamide;

1-[4-[3-Chloro-4-(ethoxy)phenyl]-6-(methylamino)-1,3,5-triazin-2-yl]-N-{[2-(trifluoromethyl)phenyl]methyl}-4-piperidinecarboxamide;

1-[4-[3-(Dimethylamino)phenyl]-6-(methylamino)-1,3,5-triazin-2-yl]-N-{[2-(trifluoromethyl)phenyl]methyl}-4-piperidinecarboxamide;

1-[4-(Methylamino)-6-(3-pyridinyl)-1,3,5-triazin-2-yl]-N-{[2-(trifluoromethyl)phenyl]methyl}-4-piperidinecarboxamide;

1-[4-(Methylamino)-6-(4-pyridinyl)-1,3,5-triazin-2-yl]-N-{[2-(trifluoromethyl)phenyl]methyl}-4-piperidinecarboxamide;

1-{4-(Methylamino)-6-[4-(methoxy)phenyl]-1,3,5-triazin-2-yl}-N-{[2-(trifluoromethyl)phenyl]methyl}-4-piperidinecarboxamide;

1-{4-(Methylamino)-6-[3-(methyloxy)phenyl]-1,3,5-triazin-2-yl}-N-{[2-(trifluoromethyl)phenyl]methyl}-4-piperidinecarboxamide;

1-[4-[4-(Ethoxy)phenyl]-6-(methylamino)-1,3,5-triazin-2-yl]-N-{[2-(trifluoromethyl)phenyl]methyl}-4-piperidinecarboxamide;

1-[4-(3-Cyanophenyl)-6-(methylamino)-1,3,5-triazin-2-yl]-N-{[2-(trifluoromethyl)phenyl]methyl}-4-piperidinecarboxamide;

1-[4-(4-Cyanophenyl)-6-(methylamino)-1,3,5-triazin-2-yl]-N-{[2-(trifluoromethyl)phenyl]methyl}-4-piperidinecarboxamide;

1-{4-(Methylamino)-6-[4-(methylsulfonyl)phenyl]-1,3,5-triazin-2-yl}-N-{[2-(trifluoromethyl)phenyl]methyl}-4-piperidinecarboxamide;

1-[4-[4-(Ethylsulfonyl)phenyl]-6-(methylamino)-1,3,5-triazin-2-yl]-N-{[2-(trifluoromethyl)phenyl]methyl}-4-piperidinecarboxamide;

1-[4-(2-Fluorophenyl)-6-(methylamino)-1,3,5-triazin-2-yl]-N-{[2-(trifluoromethyl)phenyl]methyl}-4-piperidinecarboxamide;

1-(4-(Methylamino)-6-{4-[(trifluoromethyl)oxy]phenyl}-1,3,5-triazin-2-yl)-N-{[2-(trifluoromethyl)phenyl]methyl}-4-piperidinecarboxamide;

1-(4-(Methylamino)-6-{3-[(trifluoromethyl)oxy]phenyl}-1,3,5-triazin-2-yl)-N-{[2-(trifluoromethyl)phenyl]methyl}-4-piperidinecarboxamide;

1-[4-Methyl-6-(methylamino)-1,3,5-triazin-2-yl]-N-{[2-(trifluoromethyl)phenyl]methyl}-4-piperidinecarboxamide;

1-(4-Amino-6-methyl-1,3,5-triazin-2-yl)-N-{[2-(trifluoromethyl)phenyl]methyl}-4-piperidinecarboxamide 1-[4-Ethyl-6-(4-methyl-1-piperazinyl)-1,3,5-triazin-2-yl]-N-{[2-(trifluoromethyl)phenyl]methyl}-4-piperidinecarboxamide;

1-[4-Ethyl-6-(4-morpholinyl)-1,3,5-triazin-2-yl]-N-{[2-(trifluoromethyl)phenyl]methyl}-4-piperidinecarboxamide;

1-(4-Amino-6-ethyl-1,3,5-triazin-2-yl)-N-{[2-(trifluoromethyl)phenyl]methyl}-4-piperidinecarboxamide 1-[4-Amino-6-(1-methylethyl)-1,3,5-triazin-2-yl]-N-{[2-(trifluoromethyl)phenyl]methyl}-4-piperidinecarboxamide;

1-[4-Amino-6-(2-methylpropyl)-1,3,5-triazin-2-yl]-N-{[2-(trifluoromethyl)phenyl]methyl}-4-piperidinecarboxamide;

1-(4-Amino-6-phenyl-1,3,5-triazin-2-yl)-N-{[2-(trifluoromethyl)phenyl]methyl}-4-piperidinecarboxamide;

1-[4-Ethyl-6-(methylamino)-1,3,5-triazin-2-yl]-N-{[2-(trifluoromethyl)phenyl]methyl}-4-piperidinecarboxamide;

N-[(4-Chlorophenyl)methyl]-1-[4-(methylamino)-6-phenyl-1,3,5-triazin-2-yl]-4-piperidinecarboxamide 1-[4-(Methylamino)-6-phenyl-1,3,5-triazin-2-yl]-N-[(2,4,6-trimethylphenyl)methyl]-4-piperidinecarboxamide;

N-[(2,4-Dichlorophenyl)methyl]-1-[4-(methylamino)-6-phenyl-1,3,5-triazin-2-yl]-3-piperidinecarboxamide;

1-[4-(Methylamino)-6-phenyl-1,3,5-triazin-2-yl]-N-{[2-(trifluoromethyl)phenyl]methyl}-3-piperidinecarboxamide;

1-[4-(Methylamino)-6-phenyl-1,3,5-triazin-2-yl]-N-{[2-(trifluoromethyl)phenyl]methyl}-4-piperidinecarboxamide;

1-[4-(Methylamino)-6-(3-thienyl)-1,3,5-triazin-2-yl]-N-{[2-(trifluoromethyl)phenyl]methyl}-4-piperidinecarboxamide;

1-[4-[4-(1,1-Dimethylethyl)phenyl]-6-(methylamino)-1,3,5-triazin-2-yl]-N-{[2-(trifluoromethyl)phenyl]methyl}-4-piperidinecarboxamide;

N-{[4-cyano-2-(trifluoromethyl)phenyl]methyl}-1-[4-methyl-6-(methylamino)-1,3,5-triazin-2-yl]-4-piperidinecarboxamide;

1-[4-methyl-6-(methylamino)-1,3,5-triazin-2-yl]-N-({2-[(trifluoromethyl)thio]phenyl}methyl)-4-piperidinecarboxamide;

1-[4-methyl-6-(methylamino)-1,3,5-triazin-2-yl]-N-({2-[(trifluoromethyl)thio]phenyl}methyl)-4-piperidinecarboxamide;

1-[4-methyl-6-(methylamino)-1,3,5-triazin-2-yl]-N-{[4-(methyloxy)-2-(trifluoromethyl)phenyl]methyl}-4-piperidinecarboxamide;

N-[(2,4-dichlorophenyl)methyl]-1-{4-[(2-hydroxyethyl)amino]-6-methyl-1,3,5-triazin-2-yl}-4-piperidinecarboxamide;

N-({4-bromo-2-[(trifluoromethyl)oxy]phenyl}methyl)-1-[4-methyl-6-(methylamino)-1,3,5-triazin-2-yl]-4-piperidinecarboxamide; and N-{[4-fluoro-2-(trifluoromethyl)phenyl]methyl}-1-[4-methyl-6-(methylamino)-1,3,5-triazin-2-yl]-4-piperidinecarboxamide;

or a pharmaceutically acceptable salt thereof.

A specific compound of the invention is N-({4-bromo-2-[(trifluoromethyl)oxy]phenyl}methyl)-1-[4-methyl-6-(methylamino)-1,3,5-triazin-2-yl]-4-piperidinecarboxamide; or a pharmaceutically acceptable salt thereof.

Compound Preparation

The compounds according to Formula I are prepared using conventional organic syntheses. Suitable synthetic routes are depicted below in the following general reaction schemes. All functional groups are as defined in Formula I unless otherwise defined. Starting materials and reagents depicted below in the general reaction schemes are commercially available or can be made from commercially available starting materials using methods known by those skilled in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

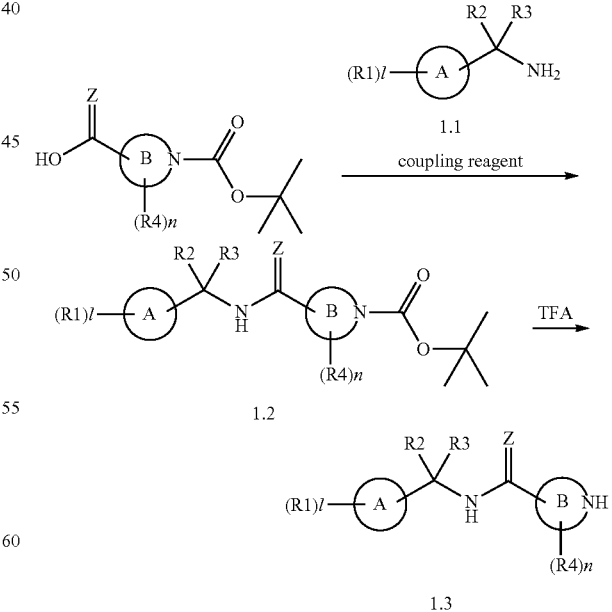

Scheme 1

Scheme 1 represents a general reaction scheme for preparing intermediate 1.3. As shown in Scheme 1, amide 1.2 can be prepared by treatment of the boc-protected amino acid (commercially available or made from commercially available starting materials using methods known to those skilled in the art) with amine 1.1 and an amide coupling reagent (such as EDCI or BOP) in a solvent (such as DMF) at room temperature. Subsequent hydrolysis of the boc-protecting group can be achieved with TFA.

chlorotriazine 2.4. Alternatively, intermediate 2.4 can be prepared by addition of 1 equivalent of amide 2.2 and a base to cyanuric chloride, followed by addition of 1 equivalent of HNR5aR6a and a base. Intermediate 2.4 may then be treated with excess HY (commercially available or made from commercially available starting materials using methods known

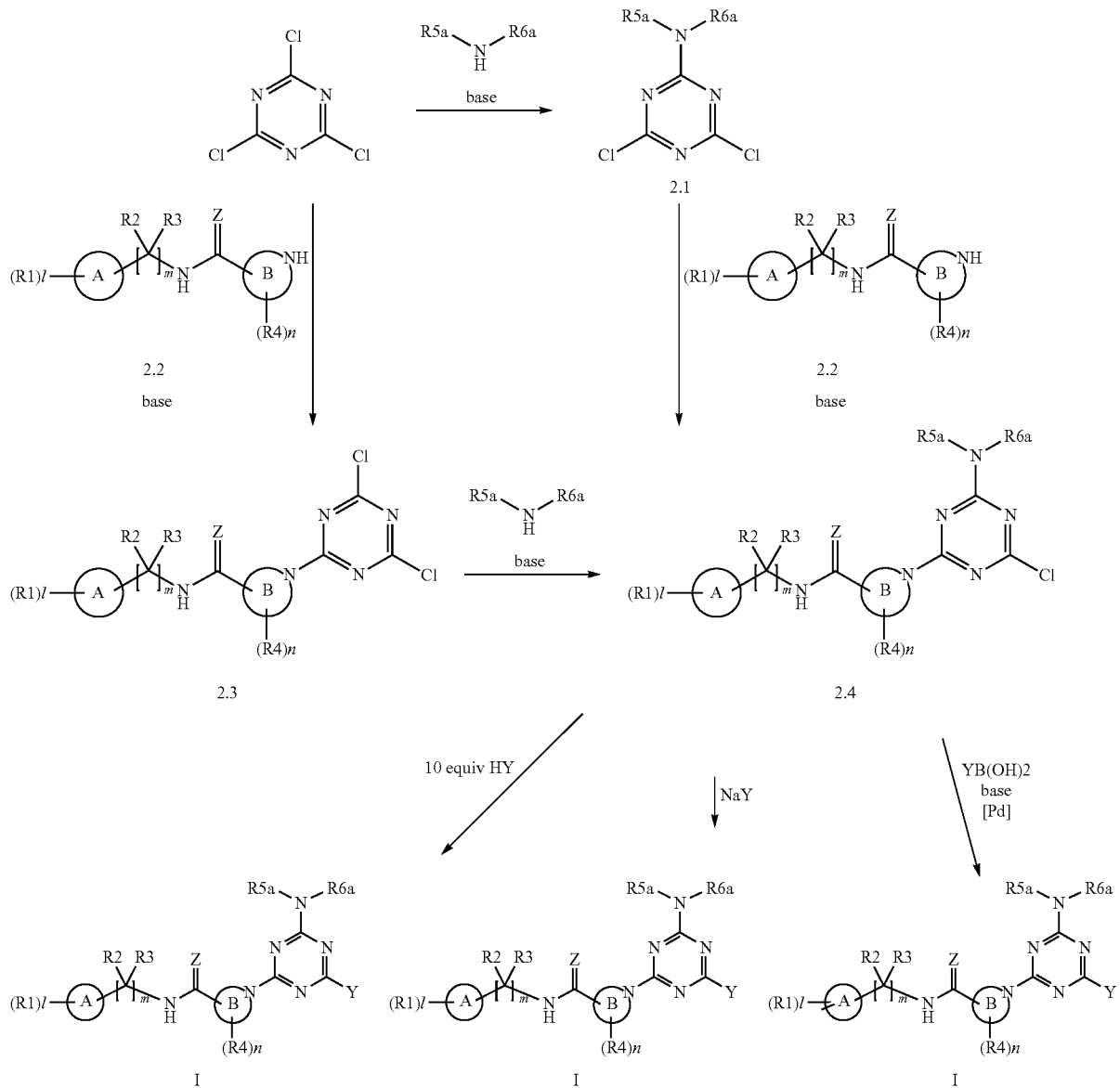

Scheme 2 represents a general reaction scheme for preparing certain compounds according to Formula I. The dichlorotriazine intermediate 2.1 can be synthesized by the treatment of cyanuric chloride (commercially available) with 1 equivalent of HNR5aR6a (commercially available or made from commercially available starting materials using methods known to those skilled in the art) and a base (such as NaOH or Hünig's base) in a solvent (such as MeCN and water) at 0° C. Subsequent addition of 1 equivalent of amide 2.2 (depicted above as intermediate 1.3) and a base (such as NaOH or Hünig's base) in a solvent (such as MeCN and water) at temperatures between 25 and 50° C. affords monoto those skilled in the art) to provide compounds according to Formula I wherein Y is NR5bR6b. Intermediate 2.4 may also be treated with NaY (commercially available or made from commercially available starting materials using methods known to those skilled in the art) to provide compounds according to Formula I wherein Y is OH or R12. Finally, intermediate 2.4 may also be treated with the boronic acid YB(OH)$_2$ (commercially available or made from commercially available starting materials using methods known to those skilled in the art), a palladium source (such as Pd (PPh$_3$)$_4$), and a base (such as Na$_2$CO$_3$) in a solvent (such as MeCN and water) at temperatures between 80 and 170° C.

(thermal or microwave heat) to provide compounds according to Formula I wherein Y is R7, R8, R9, R10, or R11.

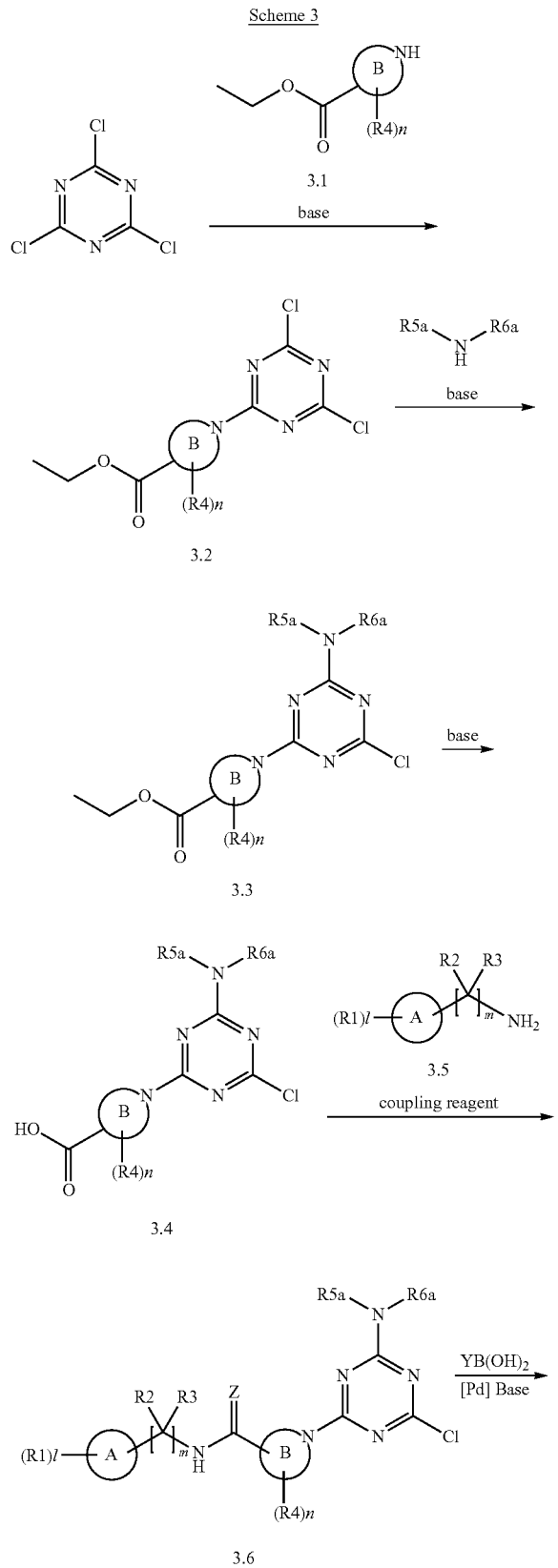

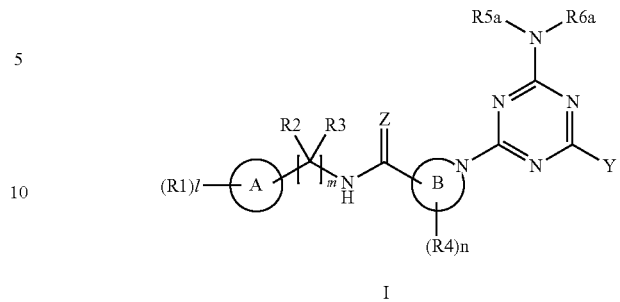

Scheme 3 represents another general reaction scheme for preparing certain compounds according to Formula I. As shown in Scheme 3, cyanuric chloride (commercially available) can be treated with 1 equivalent of amino ethylcarboxylate 3.1 (commercially available or made from commercially available starting materials using methods known to those skilled in the art) and a base (such as NaOH or Hünig's base) in a solvent (such as MeCN and water) at 0° C. Treatment of resulting intermediate 3.2 with 1 equivalent of HNR5aR6a (commercially available or made from commercially available starting materials using methods known to those skilled in the art) and a base (such as NaOH or Hünig's base) in a solvent (such as MeCN and water) at temperatures between 25 and 50° C. affords mono-chlorotriazine intermediate 3.3. The ester may then be hydrolyzed by heating in the presence of a base (such as NaOH) in a solvent (such as MeOH) at temperatures between 25 and 80° C. The resulting carboxylic acid 3.4 can be coupled to amine 3.5 (depicted above as intermediate 1.3) using a coupling reagent (such as EDCI or BOP) in a solvent (such as DMF) at room temperature. The resulting compound 3.6 can be treated with the boronic acid YB(OH)$_2$ (commercially available or made from commercially available starting materials using methods known to those skilled in the art), a palladium source (such as Pd(PPh$_3$)$_4$), and a base (such as Na$_2$CO$_3$) in a solvent (such as MeCN and water) at temperatures between 85 and 170° C. (thermal or microwave heat) to provide compounds according to Formula I wherein Y is R7, R8, R9, R10, or R11 (but not attached via a heteroatom).

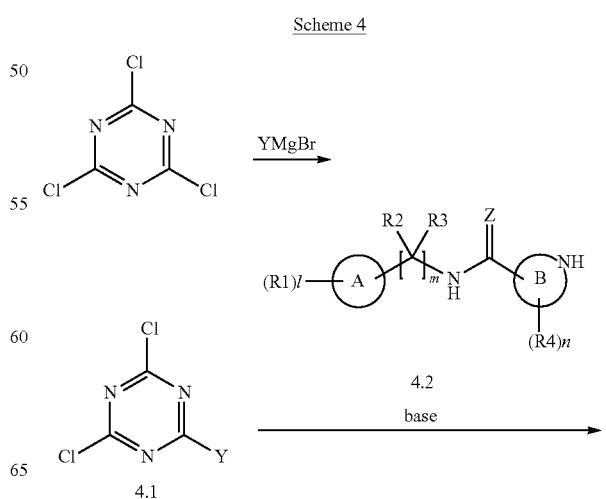

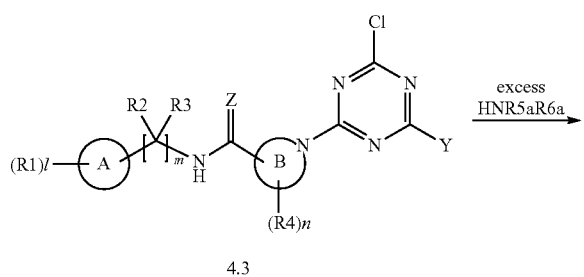

Scheme 4 represents another general reaction scheme for preparing certain compounds according to Formula I. 2,4-Dichlorotriazine 4.1 can be synthesized by addition of 1 equivalent of the appropriate Grignard reagent wherein Y is R7, R8, R9, R10, or R11 (commercially available or made from commercially available starting materials using methods known to those skilled in the art) to cyanuric chloride (commercially available) at 0° C. in a solvent (such as THF). Alternatively, intermediate 4.1 wherein Y is H is commercially available. Intermediate 4.1 can be treated with 1 equivalent of amide 4.2 (depicted above as intermediate 1.3) and a base (such as NaOH or Hünig's base) in a solvent (such as MeCN and water) at temperatures between 25 and 50° C. to afford mono-chlorotriazine 4.3. Intermediate 4.3 can be treated with excess HNR5aR6a (commercially available or made from commercially available starting materials using methods known to those skilled in the art) and a base (such as NaOH or Hünig's base) in a solvent (such as MeCN and water) at elevated temperature (60 to 80° C.) to provide compounds according to Formula I wherein Y is H, R7, R8, R9, R10, or R11.

Scheme 5 represents another general reaction scheme for preparing certain compounds according to Formula I. 2,4-Dichlorotriazine 5.1 can be synthesized by addition of 1 equivalent of the appropriate Grignard reagent wherein Y is R7, R8, R9, R10, or R11 (commercially available or made from commercially available starting materials using methods known to those skilled in the art) to cyanuric chloride in a solvent (such as THF) at 0° C. Alternatively, intermediate 5.1 wherein Y is H is commercially available. Intermediate 5.1 can be treated with 1 equivalent of HNR5aR6a (commercially available or made from commercially available starting materials using methods known to those skilled in the art) and a base (such as NaOH or Hünig's base) in a solvent (such as MeCN and water) at temperatures between 25 and 50° C. The resulting intermediate 5.2 can be reacted with excess amino acid 5.3 (commercially available or made from commercially available starting materials using methods known to those skilled in the art) at elevated temperature (60 to 80° C.) in a solvent (such as MeCN and water) to afford carboxylic acid 5.4. Intermediate 5.4 can be treated with amine 5.5 (depicted above as intermediate 1.1) and a coupling reagent (such as EDCI or BOP) in a solvent (such as DMF) at room temperature to provide compounds according to Formula I wherein Y is H, R7, R8, R9, R10, or R11 (but not attached via a heteroatom).

Scheme 6

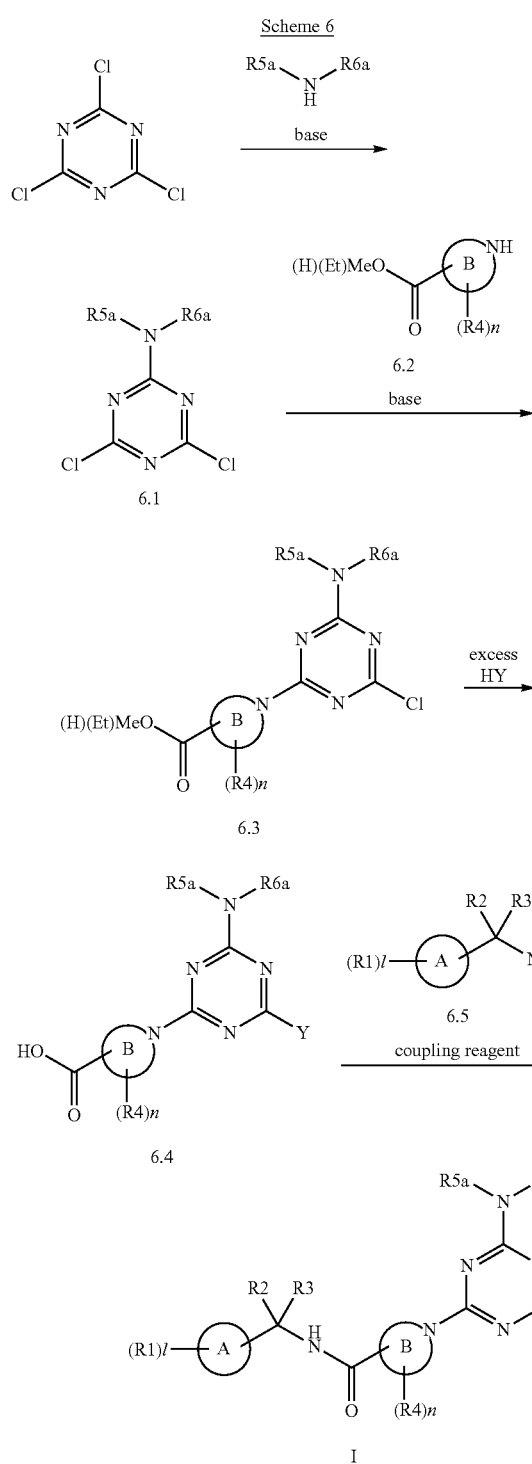

available or made from commercially available starting materials using methods known to those skilled in the art) and a base (such as NaOH or Hünig's base) in a solvent (such as MeCN and water) at temperatures between 25 and 50° C. to afford mono-chlorotriazine 6.3. In cases where reagent 6.2 contains an ester, hydrolysis of the product to the corresponding carboxylic acid 6.3 can be achieved with a base (such as NaOH) in a solvent (such as MeOH) at temperatures between 25 and 80° C. The resulting monochlorotriazine 6.3 can subsequently be treated with excess HY (commercially available or made from commercially available starting materials using methods known to those skilled in the art) and a base (such as NaOH or Hünig's base) in a solvent (such as MeCN and water) at elevated temperatures to afford intermediate 6.4. Finally, the resulting carboxylic acid can be coupled to amine 6.5 (depicted above as intermediate 1.1) using a coupling reagent (such as EDCI or BOP) in a solvent (such as DMF) at room temperature to provide compounds according to Formula I wherein Y is NR5bR6b.

Scheme 7

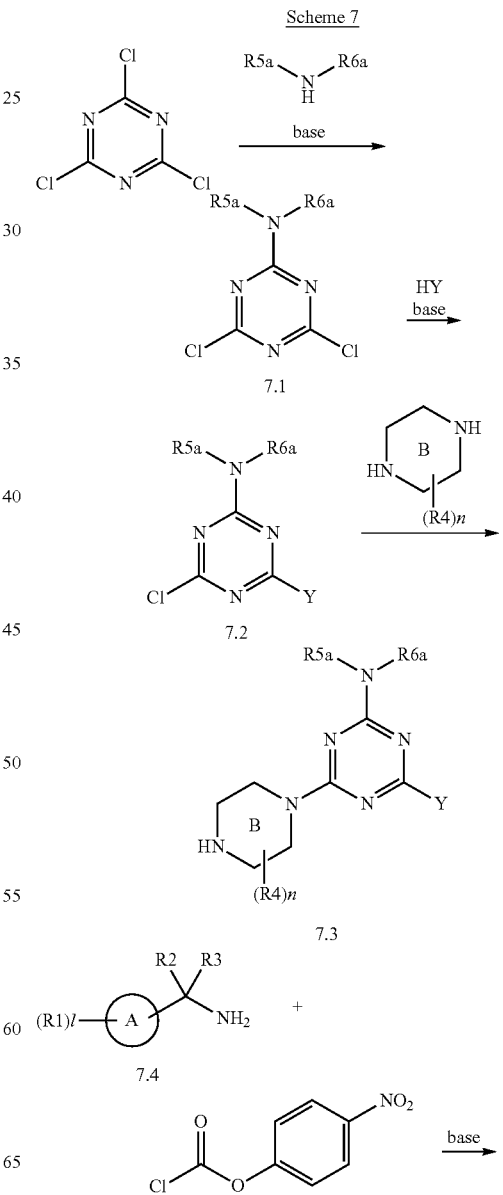

Scheme 6 represents another general reaction scheme for preparing certain compounds according to Formula I. As shown in Scheme 6, cyanuric chloride can be treated with 1 equivalent of HNR5aR6a (commercially available or made from commercially available starting materials using methods known to those skilled in the art) and a base (such as NaOH or Hünig's base) in a solvent (such as MeCN and water) at 0° C. to afford di-chlorotriazine 6.1. Intermediate 6.1 can be treated with 1 equivalent of amino methyl- or ethylcarboxylate or amino carboxylic acid 6.2 (commercially

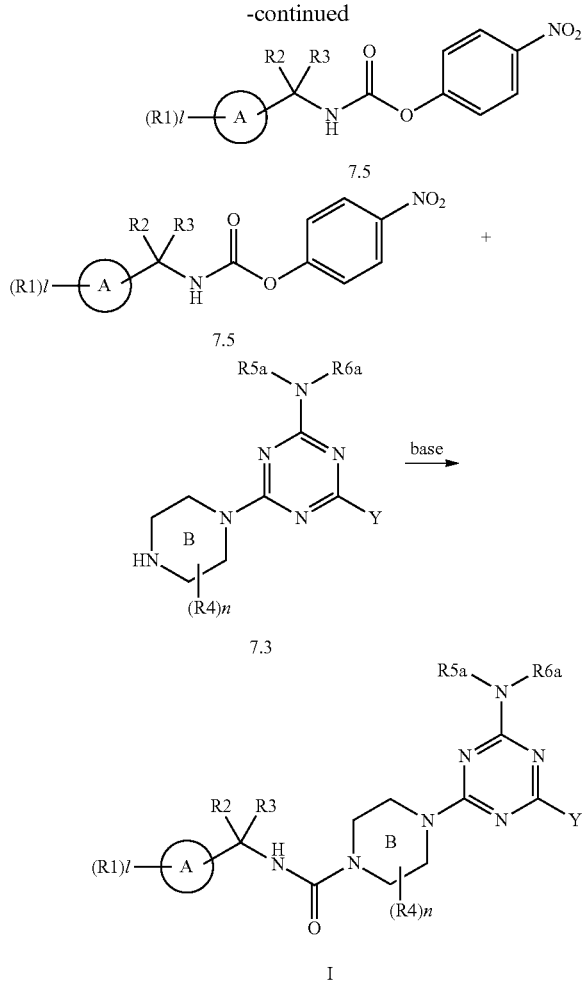

Scheme 7 represents another general reaction scheme for preparing certain compounds according to Formula I. As shown in Scheme 7, cyanuric chloride can be treated with 1 equivalent of HNR5aR6a (commercially available or made from commercially available starting materials using methods known to those skilled in the art) and a base (such as NaOH or Hünig's base) in a solvent (such as MeCN and water) at 0° C. to afford di-chlorotriazine 7.1. Intermediate 7.1 may be treated with 1 equivalent of HY (commercially available or made from commercially available starting materials using methods known to those skilled in the art) and a base (such as NaOH or Hünig's base) in a solvent (such as MeCN and water) at temperatures between 25 and 50° C. to provide mono-chlorotriazine 7.2. Intermediate 7.1 can subsequently be treated with excess piperazine and a base (such as NaOH or Hünig's base) in a solvent (such as MeCN and water) at temperatures between 60 and 80° C. to provide intermediate 7.3. Carbamate 7.5 can be synthesized via the slow addition of amine 7.4 (depicted above as intermediate 1.1) to p-nitrophenylchloroformate in the presence of a base (such as triethylamine) in a solvent (such as CH$_2$Cl$_2$). Carbamate 7.5 may then be treated with intermediate 7.3 and a base (such as triethylamine) in a solvent (such as CH$_2$Cl$_2$) to provide compounds according to Formula I wherein Y is —NR5bR6b and B is B4.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Intermediate 1

2,4-dichloro-6-methyl-1,3,5-triazine

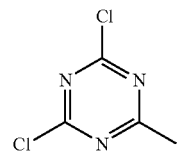

Methyl magnesium bromide (3M in ethyl ether, 9 ml, 27 mmol) was added dropwise over 10 min to a cooled (0° C.) solution of 2,4,6-trichloro-1,3,5-triazine (5 g, 27 mmol) in tetrahydrofuran (270 ml). The reaction mixture was stirred at ambient temperature for 20 hours and was then quenched with saturated NH$_4$Cl (aq) (100 mL). The aqueous layer was extracted using dichloromethane (3×50 mL), and the combined organic layers were dried over Na$_2$SO$_4$, filtered, and concentrated to remove the most of solvent. Celite was then added to the solution and the resulting suspension was concentrated to dryness under vacuum and purified using silica gel chromatography (120 g SiO$_2$ gel column; solvent dichloromethane/hexane from 0 to 30%) to give 2,4-dichloro-6-methyl-1,3,5-triazine (1.38 g of 90% purity, 7.57 mmol, 28%). MS (ES) m/e 164 [M+H]+.

Intermediate 2

1-[4-methyl-6-(methylamino)-1,3,5-triazin-2-yl]-4-piperidinecarboxylic acid

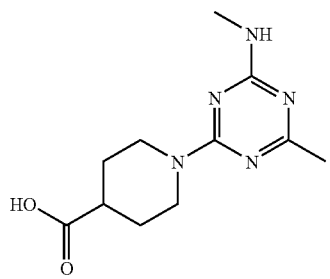

2,4-dichloro-6-methyl-1,3,5-triazine (5 g, 31 mmol) was dissolved in a 1:1 mixture of acetonitrile and water and treated with an aqueous solution of methyl amine (0.88 mL, 31 mmol) at a low temperature maintained by immersing the reaction flask in an ice bath. The pH of the reaction mixture was adjusted to 9-10 with 1M NaOH and the reaction was stirred for 30 minutes. Then, 4-piperidinecarboxylic acid (5 g, 39 mmol) was added and the pH was maintained between 9 and 10 with additions of 1M NaOH as needed. The reaction was allowed to warm to room temperature and stirred for one hour. The reaction mixture was then concentrated and purified by preparative HPLC to provide 1-[4-methyl-6-(methylamino)-1,3,5-triazin-2-yl]-4-piperidinecarboxylic acid (31 mmol, 100%) as a white solid. MS (ES) m/e 252 [M+H]+. $^1$H NMR (400 MHz, methanol-D4) ⊆ 4.7 (m, 2H), 3.3 (s, 2H), 3.0 (s, 3H), 2.7 (m, 1H), 2.4 (s, 3H), 2.0 (m, 2H), 1.7 (m, 2H)

Intermediate 3

4-(aminomethyl)-3-(trifluoromethyl)benzonitrile

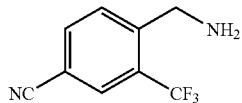

Step 1:
4-(bromomethyl)-3-(trifluoromethyl)benzonitrile

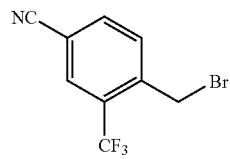

4-methyl-3-(trifluoromethyl)benzonitrile (10 g, 54 mmol) was dissolved in 200 mL of carbon tetrachloride and treated with N-bromosuccinimide (10.5 g, 59 mmol) and benzoyl peroxide (1.3 g, 0.54 mmol). The reaction mixture was heated to reflux temperature and stirred for one week. Then, 80 mL of water was added and the layers were separated. The aqueous layer was extracted with methylene chloride (2×50 mL). The combined organic layers were washed with water (2×50 mL), dried over magnesium sulfate, and concentrated to provide 4-(bromomethyl)-3-(trifluoromethyl)benzonitrile (14 g, 53 mmol) as a yellow oil which was used in the next step without further purification.

Step 2:
4-(aminomethyl)-3-(trifluoromethyl)benzonitrile

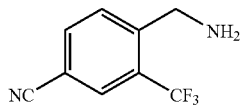

4-(bromomethyl)-3-(trifluoromethyl)benzonitrile (14 g) was dissolved in 500 mL of a solution of 5M ammonia in methanol and stirred for 24 hours at room temperature. The solvent was removed under vacuum to provide a yellow solid which was dissolved in 1M HCl and extracted with diethyl ether (3×30 mL). The aqueous layer was then adjusted to a pH of 9-10 with 1M NaOH and extracted with dichloromethane (3×80 mL). This provided 4-(aminomethyl)-3-(trifluoromethyl)benzonitrile (4.7 g, 23 mmol, 43%) as a yellow solid. MS (ES) m/e 201 [M+H]+.

Intermediate 4

{[4-(methyloxy)-2-(trifluoromethyl)phenyl]methyl}amine

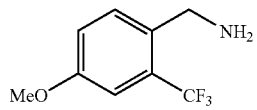

To a mixture of 4-(methyloxy)-2-(trifluoromethyl)benzaldehyde (14 g, 65 mmol, 1.0 equiv), aqueous NH$_3$ (25-28%, 370 mL, 5.20 mol, 80 equiv), and MeOH (300 mL) was added Raney-Ni (3.8 g, 65 mmol, 1.0 equiv). The flask was fitted with a hydrogen balloon, and the mixture was stirred for 7 days at room temperature. The reaction mixture was filtered through a celite cake, and the filtrate was concentrated. The residue was purified by HPLC to afford 9 g (67%) of the title compound as the trifluoroacetate salt. MS (ES+): m/e 206 [M+H]+. $^1$H NMR (400 MHz, DMSO-D6) ⊆ 7.6 (d, 1H), 7.3 (d, 1H), 7.2 (s, 1H), 4.1 (s, 2H), 3.8 (s, 3H)

Intermediate 5

N-[(2,4-dichlorophenyl)methyl]-4-piperidinecarboxamide

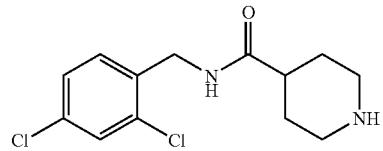

Step 1: 1,1-dimethylethyl-4-({[(2,4-dichlorophenyl)methyl]amino}carbonyl)-1-piperidinecarboxylate

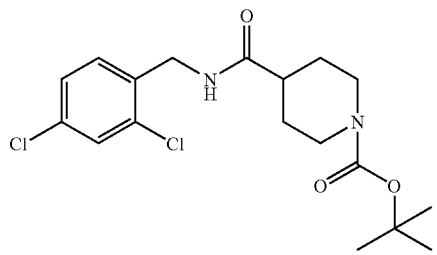

A 1000 mL round-bottom flask charged with argon was equipped with a magnetic stir bar, prior to the addition of 1-{[(1,1-dimethylethyl)oxy]carbonyl}-4-piperidinecarboxylic acid (16.32 g, 71.2 mmol), 2,4-dichlorobenzylamine (9.5 mL, 71.2 mmol) and 100 mL of DMF at room temperature. Afterwards, triethylamine (29.8 mL, 213.5 mmol) was added and the solution was allowed to stir for several minutes before a separate solution of 1H-1,2,3-benzotriazol-1-yloxy-tris(dimethylamino)-phosphonium hexafluorophosphate (BOP reagent, 31.5 g, 71.2 mmol) dissolved in 78 mL of DMF was delivered to the mixture at room temperature. The reaction was maintained at that temperature for 48 hours, before it was determined to be complete by LCMS (Rt=8.6 min and m/e 388 [M+1]+). Pouring the crude mixture into a vigorously stirring 50/50 solution of saturated sodium bicarbonate and water (1.5 L), resulted in the precipitation of the desired product as an off-white solid. The solid was recovered by vacuum filtration and dried for 24 hours under vacuum to give 27.2 g of 1,1-dimethylethyl-4-({[(2,4-dichlorophenyl)methyl]amino}carbonyl)-1-piperidinecarboxylate (70.2 mmol, 98.6%). MS (ES) m/e 388 [M+H]+. $^1$H NMR (400 MHz, DMSO-D6) ⌑ 8.4 (m, 1H), 7.6 (d, 1H), 7.3 (d, 1H), 4.3 (m, 2H), 4.0 (m, 2H), 2.7 (m, 2H), 2.3 (m, 1H), 1.7 (m, 2H), 1.5 (m, 2H), 1.4 (s, 9H)

Step 2: N-[(2,4-dichlorophenyl)methyl]-4-piperidinecarboxamide

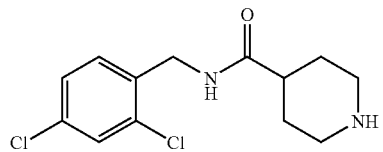

A 500 mL round bottom flask equipped with a magnetic stir bar was charged with 1,1-di methylethyl-4-({[(2,4-dichlorophenyl)methyl]amino}carbonyl)-1-piperidinecarboxylate (27.6 g, 71.2 mmol) and DCM (117 mL) at room temperature. Trifluoroacetic acid (117 mL) was added slowly, and the reaction was maintained at room temperature for 1 hour after which time LC/MS determined that the reaction was complete (Rt=6.03 min and m/e 287 [M+1]+). The volatiles were removed by rotary evaporation and the crude oil was dissolved in ethyl acetate and washed with saturated sodium bicarbonate solution (3×200 mL). The organic phase was dried over Na$_2$SO$_4$, filtered and concentrated to give 13.5 g of the title compound (47 mmol, 66%) as a pale yellow solid. MS (ES) m/e 287 [M+H]+. $^1$H NMR (400 MHz, DMSO-D6) ⌑ 8.6 (m, 1H), 7.4 (d, 1H), 7.3 (d, 1H), 4.3 (m, 2H), 3.2 (m, 2H), 2.8 (m, 2H), 2.5 (m, 1H shouldering on DMSO peak), 1.8 (m, 2H), 1.7 (m, 2H)

Intermediate 6

1-{4-bromo-2-[(trifluoromethyl)oxy]phenyl}methanamine

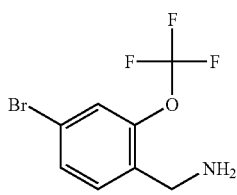

Step 1:
4-bromo-2-[(trifluoromethyl)oxy]benzaldehyde

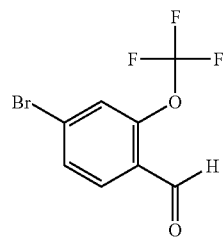

5-bromo-2-iodophenyl trifluoromethyl ether (500 mg, 1.37 mmol) was dissolved in 10 mL of anhydrous THF and cooled to −70° C. Then, n-butyllithium (0.55 mL of a 2.5 M solution, 1.37 mmol) was added dropwise over the course of 30 minutes. DMF (0.19 mL, 2.74 mmol) was added and the reaction was stirred for 30 minutes at −70° C. and then allowed to warm to 0° C. and stir for three hours. The reaction was quenched with 5 mL of saturated ammonium chloride solution and extracted with ethyl acetate. The organic layer was washed with water, dried over magnesium sulfate, filtered, and concentrated to provide 4-bromo-2-[(trifluoromethyl)oxy]benzaldehyde (100 mg, 0.37 mmol, 27%) as a yellow solid. $^1$H NMR (400 MHz, DMSO-D6) ⌑ 10.1 (s, 1H), 7.9 (s, 3H)

Step 2: 1-{4-bromo-2-[(trifluoromethyl)oxy]phenyl}methanamine

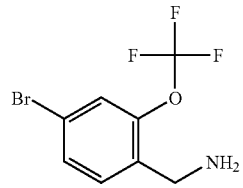

4-bromo-2-[(trifluoromethyl)oxy]benzaldehyde (3 g, 11.2 mmol) was dissolved in 100 mL of a 5M solution of ammonia in methanol and stirred overnight, after which the reaction mixture was treated with sodium borohydride (858 mg, 22.5 mmol) and stirred at room temperature for four days. The reaction was quenched by the addition of 20 mL of water and stirred for 30 minutes. The volatiles were removed and the residue was extracted with methylene chloride (3×20 mL). The methylene chloride was evaporated to give a yellow oil which was purified by preparative HPLC to provide the TFA salt of 1-{4-bromo-2-[(trifluoromethyl)oxy]phenyl}methanamine (900 mg, 3.3 mmol, 29%) as a white solid. MS (ES) m/e 270, 272 [M+H]+. $^1$H NMR (400 MHz, DMSO-D6) ⌑ 8.5 (bs, 2H), 7.8 (d, 1H), 7.7 (s, 1H), 7.6 (d, 1H), 4.1 (bs, 2H)

Example 1

1-(4-(Methylamino)-6-{[(2R)-2-phenylpropyl]amino}-1,3,5-triazin-2-yl)-N-{[2-(trifluoromethyl)phenyl]methyl}-4-piperidinecarboxamide

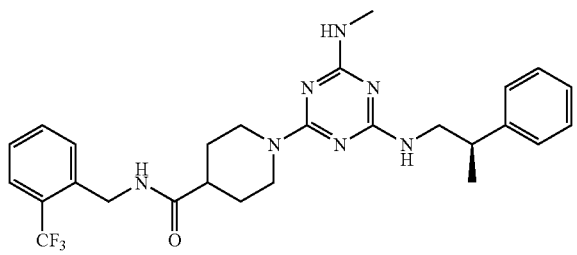

a) Preparation of N-{[2-(trifluoromethyl)phenyl]methyl}-4-piperidinecarboxamide To a cold (0° C.) solution of 1-{[(1,1-dimethylethyl)oxy]carbonyl}-4-piperidinecarboxylic acid (3.68 g, 16.1 mmol, 1.00 equiv), {[2-(trifluoromethyl)phenyl]methyl}amine (2.57 mL, 18.3 mmol, 1.14 equiv), and DMAP (392 mg, 3.21 mmol, 0.200 equiv) in $CH_2Cl_2$ (100 mL) was added diisopropylethylamine (DIEA, 3.49 ml, 20.1 mmol, 1.25 equiv) and EDCI (3.11 g, 20.1 mmol, 1.25 equiv). The reaction mixture was stirred at 0° C. for 30 min and then at room temperature overnight. The solution was washed with $H_2O$, sat $NaHCO_3$ (aq) and brine. The organic layer was dried over $Na_2SO_4$, filtered, and concentrated. The residue was stirred in $CH_2Cl_2$ (60 mL) and TFA (60 mL) for 20 min at room temperature, and then the solvents were removed in vacuo. The residue was diluted with $CH_2Cl_2$, and the resulting solution was neutralized carefully with sat $NaHCO_3$ (aq). Solid NaCl was used to saturate the aqueous layer, which was then extracted 3 times with ethyl acetate. The organic layers were combined, dried with $Na_2SO_4$, filtered and concentrated to afford 4.43 g (97% yield) of the desired product. MS (ES+): m/e 287.0 [M+H]+.

b) Preparation of 4,6-dichloro-N-methyl-1,3,5-triazin-2-amine

To a suspension of cyanuric chloride (300 mg, 1.63 mmol, 1.00 equiv) in 1:1 $CH_3CN:H_2O$ (2.7 mL) at 0° C. was added $NH_2Me$ (2.0 M solution in THF, 0.81 mL, 1.6 mmol). The solution was treated with 1 N NaOH to maintain a pH of 9-10 and stirred for 5 min at 0° C. The resulting suspension was used in the next step without workup or purification. MS (ES+): m/e 178.9 [M+H]+.

c) Preparation of 1-[4-chloro-6-(methylamino)-1,3,5-triazin-2-yl]-N-{[2-(trifluoromethyl)phenyl]methyl}-4-piperidinecarboxamide N-{[2-(Trifluoromethyl)phenyl]methyl}-4-piperidinecarboxamide (464 mg, 1.63 mmol, 1.00 equiv) was added to the suspension prepared in step b. The resulting mixture was heated to 40° C. and treated with 1 N NaOH to maintain a pH of 9-10. The reaction mixture was stirred for 2 h and then used immediately in the next step without workup or purification. MS (ES+): m/e 428.9 [M+H]+.

d) Preparation of 1-(4-(methylamino)-6-{[(2R)-2-phenylpropyl]amino}-1,3,5-triazin-2-yl)-N-{[2-(trifluoromethyl)phenyl]methyl}-4-piperidinecarboxamide Approximately half of the suspension prepared in step c was treated with (2R)-2-phenylpropylamine (1.16 mL, 8.14 mmol, 10.0 equiv). After heating to 80° C., the solvents were removed in vacuo, and the residue was purified by reverse-phase HPLC (Sunfire, 35-60% $CH_3CN/H_2O$, 0.1% TFA, 12 min) to afford 156 mg of the title compound. MS (ES+): m/e 528.1 [M+H]+.

Example 2

1-[4-[[2-(Dimethylamino)ethyl](methyl)amino]-6-(methylamino)-1,3,5-triazin-2-yl]-N-{[2-(trifluoromethyl)phenyl]methyl}-4-piperidinecarboxamide

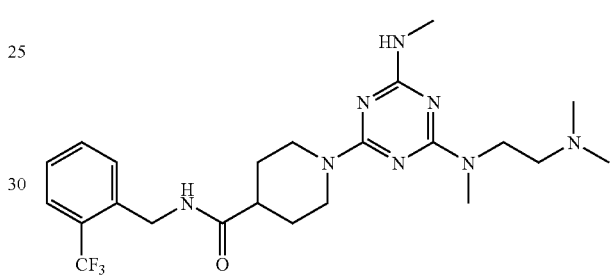

Example 2 was prepared using the general procedure described above in Example 1 substituting the appropriate starting materials. MS (ES+): m/e 495.1 [M+H]+.

Example 3

1-[4-[(1,1-Dimethylethyl)amino]-6-(4-methyl-1-piperazinyl)-1,3,5-triazin-2-yl]-N-{[2-(trifluoromethyl)phenyl]methyl}-4-piperidinecarboxamide

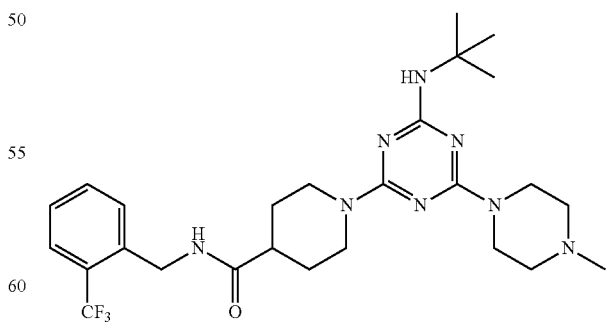

Example 3 was prepared using the general procedure described above in Example 1 substituting the appropriate starting materials. MS (ES+): m/e 535.0 [M+H]+.

Example 4

1-[4-(Methylamino)-6-(4-methyl-1-piperazinyl)-1,3,5-triazin-2-yl]-N-{[2-(trifluoromethyl)phenyl]methyl}-4-piperidinecarboxamide

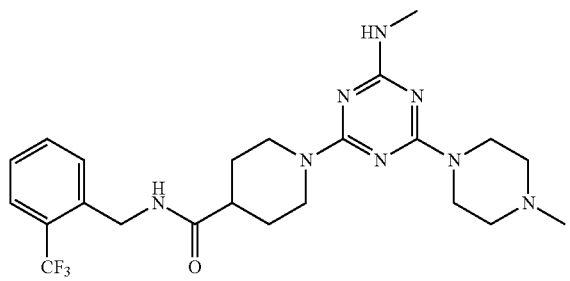

a) Preparation of 4,6-dichloro-N-methyl-1,3,5-triazin-2-amine

A mixture of cyanuric chloride (184 mg, 1.00 mmol, 1.00 equiv) in CH$_3$CN/H$_2$O (1/1, 33 ml) was cooled to 0° C. Methylamine (40 w % in H$_2$O) (0.252 ml, 3.25 mmol, 1.00 equiv) was added. The reaction mixture was adjusted to a pH of about 9-10 using 1 N NaOH. After being stirred at 0° for 10 min, the reaction was complete. The resulting suspension was used in the next step without workup or purification.

b) Preparation of methyl 1-[4-chloro-6-(methylamino)-1,3,5-triazin-2-yl]-4-piperidinecarboxylate To the above reaction mixture was added methyl isonipecotate (233 mg, 1.63 mmol, 1.00 equiv). The pH of the suspension was adjusted to about 9-10 using 1 N NaOH. The reaction mixture was stirred at room temperature for 2 h, while the pH was retained between 9 and 10. Without workup or purification, this material was used in the next step. MS (ES+): m/e 286.1 [M+H]$^+$.

c) Preparation of 1-[4-chloro-6-(methylamino)-1,3,5-triazin-2-yl]-4-piperidinecarboxylic acid To 12.5 ml (1.23 mmol) of the above mixture was added 3 ml of 5 M NaOH. The reaction was allowed to stir at room temperature for 2 h, then neutralized with 6 N HCl to give the desired carboxylic acid. Without workup or purification, this material was carried onto the next step. MS (ES+): m/e 272.1 [M+H]$^+$.

d) Preparation of 1-[4-(methylamino)-6-(4-methyl-1-piperazinyl)-1,3,5-triazin-2-yl]-4-piperidinecarboxylic acid To the above mixture (0.54 mmol) was added N-methylpiperazine (542 mg, 5.41 mmol, 10.0 equiv). The reaction mixture was heated at 80° C. for 16 h. The solvent was evaporated, and the residue was acidified and purified by reverse-phase HPLC with TFA buffer to give compound the title compound (44.7 mg). MS (ES+): m/e 336.1 [M+H]$^+$.

e) Preparation of 1-[4-(methylamino)-6-(4-methyl-1-piperazinyl)-1,3,5-triazin-2-yl]-N-{[2-(trifluoromethyl)phenyl]methyl}-4-piperidinecarboxamide A solution of 1-[4-(methylamino)-6-(4-methyl-1-piperazinyl)-1,3,5-triazin-2-yl]-4-piperidinecarboxylic acid as the TFA salt (44.7 mg, 0.100 mmol, 1.00 equiv), 2-trifluoromethyl benzylamine (26.6 mg, 0.150 mmol, 1.50 equiv) and DMAP (3.3 mg, 0.26 equiv) in dichloromethane (1 ml) was cooled in an ice bath. 1-Ethyl-3-[3-(dimethylamino)propyl] carbodiimide hydrochloride (EDCI, 32 mg, 0.17 mmol, 1.7 equiv) was added. The reaction mixture was stirred at room temperature for 2 h. The solution was diluted with dichloromethane (1 ml) and washed with saturated sodium bicarbonate and water. The solvent was removed, and the residue was purified by reverse-phase HPLC to give the title compound (66 mg, 82.5% yield). MS (ES+): m/e 493.3 [M+H]$^+$.

Example 5

1-[4-{[2-(Dimethylamino)ethyl]amino}-6-(methylamino)-1,3,5-triazin-2-yl]-N-{[2-(trifluoromethyl)phenyl]methyl}-4-piperidinecarboxamide

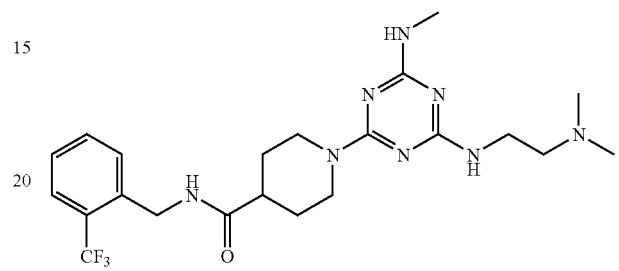

Example 5 was prepared using the general procedure described above in Example 4 substituting the appropriate starting materials. MS (ES+): m/e 481.2 [M+H]$^+$

Example 6

N-[2-(1-Cyclohexen-1-yl)ethyl]-1-(4-(methylamino)-6-{[(2R)-2-phenylpropyl]amino}-1,3,5-triazin-2-yl)-4-piperidinecarboxamide

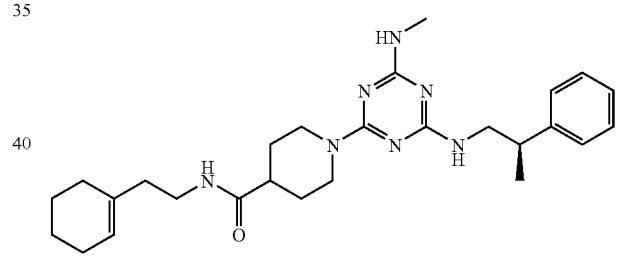

Example 6 was prepared using the general procedure described above in Example 4 substituting the appropriate starting materials. MS (ES+): m/e 478.3 [M+H]$^+$

Example 7

1-[4-(Methylamino)-6-(4-pyridinylamino)-1,3,5-triazin-2-yl]-N-{[2-(trifluoromethyl)phenyl]methyl}-4-piperidinecarboxamide

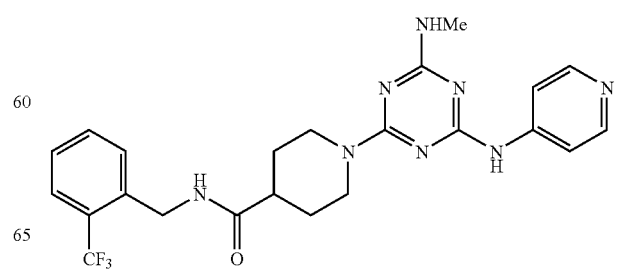

a) Preparation of 1,1-dimethylethyl 4-[({[2-(trifluoromethyl)phenyl]methyl}amino)carbonyl]-1-piperidinecarboxylate To a suspension of 1-{[(1,1-dimethylethyl)oxy]carbonyl}-4-piperidinecarboxylic acid (8.00 g, 34.9 mmol, 1.00 equiv) in CH$_2$Cl$_2$/DMF (7/1, 350 ml) at room temperature, 1-[2-(trifluoromethyl)phenyl]methanamine (4.90 mL, 34.9 mmol, 1.00 equiv), EDCI (8.03 g, 41.9 mmol, 1.20 equiv), HOBT (5.66 g, 41.9 mmol, 1.20 equiv), and diisopropylethylamine (DIEA, 18.3 ml, 105 mmol, 3.00 equiv) were added. Stirring was continued overnight at room temperature. The reaction mixture was partitioned between water and ethyl acetate (1:1, 600 ml). The product was extracted three times with ethyl acetate (100 ml). The organic extracts were combined and washed successively with saturated ammonium chloride (200 ml), water (200 ml), and saturated sodium chloride (200 ml). The ethyl acetate solution was dried with Na$_2$SO$_4$, filtered, and concentrated under reduced pressure to afford 11.67 g (87%) of the title compound. MS (ES+): m/e 408.9 [M+Na]$^+$.

b) Preparation of N-{[2-(trifluoromethyl)phenyl]methyl}-4-piperidinecarboxamide To a solution of 1,1-dimethylethyl 4-[({[2-(trifluoromethyl)phenyl]methyl}amino)-carbonyl]-1-piperidinecarboxylate and CH$_2$Cl$_2$ (180 ml) at 0° C., a premixed solution of CH$_2$Cl$_2$ and TFA (180 ml) was added. The reaction mixture was stirred at 0° C. for 10 min and at room temperature for 2 h. The solvents were removed under reduced pressure to afford 11.9 g of the title compound. MS (ES+): m/e 287.9 [M+H]$^+$.

c) Preparation of 1-(4,6-dichloro-1,3,5-triazin-2-yl)-N-{[2-(trifluoromethyl)phenyl]methyl}-4-piperidinecarboxamide To a solution of N-{[2-(trifluoromethyl)phenyl]methyl}-4-piperidinecarboxamide (950 mg, 3.32 mmol, 1.00 equiv) in acetonitrile (30 ml) at room temperature, cyanuric chloride (612 mg, 3.32 mmol, 1.00 equiv) and diisopropylethylamine (DIEA, 1.74 ml, 9.95 mmol, 3.00 equiv) were added dropwise. The reaction was stirred at room temperature for 3 h. Without workup or purification, the reaction mixture was carried forward to the next step. MS (ES+): m/e 435.9 [M+H]$^+$ d) Preparation of 1-[4-chloro-6-(methylamino)-1,3,5-triazin-2-yl]-N-{[2-(trifluoromethyl)phenyl]methyl}-4-piperidinecarboxamide A premixed solution of methylamine (1.66 ml, 3.32 mmol, 1.00 equiv), diisopropylethylamine (DIEA, 1.74 ml, 9.95 mmol, 3.00 equiv), and acetonitrile (10 ml) was added dropwise to the above reaction mixture. The reaction mixture was stirred for 3 h at room temperature. The solvents were removed under reduced pressure to provide 1.07 g of the title compound. MS (ES+): m/e 430.0 [M+H]$^+$ e) Preparation of 1-[4-(methylamino)-6-(4-pyridinylamino)-1,3,5-triazin-2-yl]-N-{[2-(trifluoromethyl)phenyl]methyl}-4-piperidinecarboxamide To a solution of 1-[4-chloro-6-(methylamino)-1,3,5-triazin-2-yl]-N-{[2-(trifluoromethyl)phenyl]methyl}-4-piperidinecarboxamide (75 mg, 0.18 mmol, 1.0 equiv) and diisopropylethylamine (DIEA, 154 μl, 0.875 mmol, 5.00 equiv) in acetonitrile (3 ml) at room temperature, 4-aminopyridine (43.0 mg, 0.349 mmol, 2.00 equiv) was added. The reaction mixture was heated to 65° C. and stirring was continued overnight. The reaction mixture was cooled to room temperature, and the solvent was removed under reduced pressure. The residue was dissolved up in 1.5 ml DMSO and purified via reverse-phase HPLC purification to afford the title compound. MS (ES+): m/e 487.1 [M+H]$^+$.

Example 8

1-[4-(Methylamino)-6-(1-piperazinyl)-1,3,5-triazin-2-yl]-N-{[2-(trifluoromethyl)phenyl]methyl}-4-piperidinecarboxamide

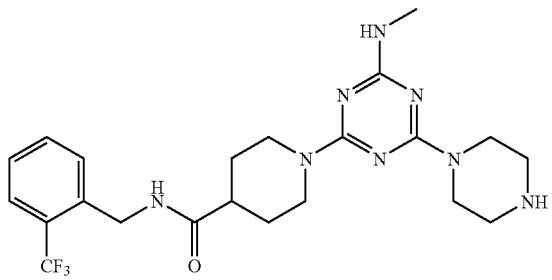

Example 8 was prepared using the general procedure described above in Example 7 substituting the appropriate starting materials. MS (ES+): m/e 478.9 [M+H]$^+$

Example 9

1-[4-Amino-6-(4-methyl-1-piperazinyl)-1,3,5-triazin-2-yl]-N-{[2-(trifluoromethyl)phenyl]methyl}-4-piperidinecarboxamide

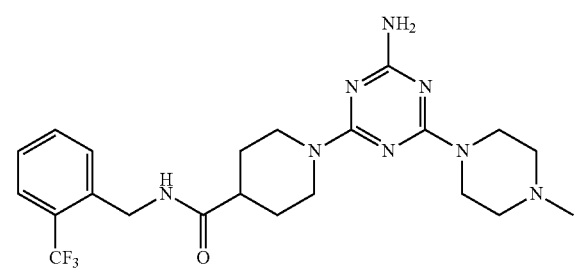

Example 9 was prepared using the general procedure described above in steps c and d of Example 1 substituting 4,6-dichloro-1,3,5-triazin-2-amine for 4,6-dichloro-N-methyl-1,3,5-triazin-2-amine in step c and N-methylpiperazine for (2R)-2-phenylpropylamine in step d. MS (ES+): m/e 478.8 [M+H]$^+$.

Example 10

1-[4-(Methylamino)-1,3,5-triazin-2-yl]-N-{[2-(trifluoromethyl)phenyl]methyl}-4-piperidinecarboxamide

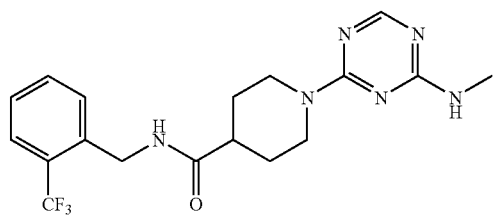

a) Preparation of 1-(4-chloro-1,3,5-triazin-2-yl)-N-{[2-(trifluoromethyl)phenyl]methyl}-4-piperidinecarboxamide To a solution of N-{[2-(trifluoromethyl)phenyl]methyl}-4-piperidinecarboxamide (315 mg, 1.10 mmol, 1.10 equiv) in acetonitrile (5 ml) at room temperature, 2,4-dichloro-1,3,5-triazine (150 mg, 1.00 mmol, 1.00 equiv) and diisopropylethylamine (DIEA, 0.875 ml, 5.00 mmol, 5.00 equiv) were added. The reaction mixture was stirred for 3 h at room temperature. Without workup or purification, the reaction was carried forward to the next step. MS (ES+): m/e 401.8 [M+H]$^+$ b) Preparation of 1-[4-(methylamino)-1,3,5-triazin-2-yl]-N-{[2-(trifluoromethyl)phenyl]methyl}-4-piperidinecarboxamide A premixed solution of methylamine (0.43 ml, 3.0 mmol, 3.0 equiv), diisopropylethylamine (DIEA, 0.87 ml, 3.0 mmol, 3.0 equiv), and acetonitrile (1 ml) was added dropwise to the above reaction (step a). The mixture was heated to 60° C. and stirring was continued for 3 h. The reaction mixture was cooled to room temperature and concentrated under reduced pressure. The residue was dissolved in DMSO and purified via reverse-phase HPLC purification to afford the title compound. MS (ES+): m/e 394.7 [M]$^+$.

Example 11

1-(4-{[(2R)-2-Phenylpropyl]amino}-1,3,5-triazin-2-yl)-N-{[2-(trifluoromethyl)phenyl]methyl}-4-piperidinecarboxamide

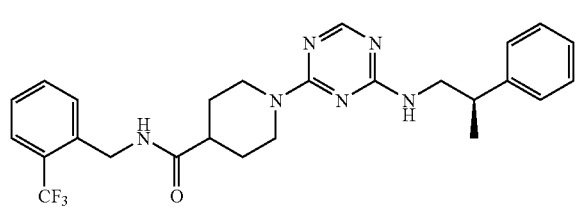

Example 11 was prepared using the general procedure described above in Example 10 substituting the appropriate starting materials. MS (ES+): m/e 499.0 [M+H]$^+$

Example 12

1-[4-({2-[(Phenylmethyl)thio]ethyl}amino)-1,3,5-triazin-2-yl]-N-{[2-(trifluoromethyl)phenyl]methyl}-4-piperidinecarboxamide

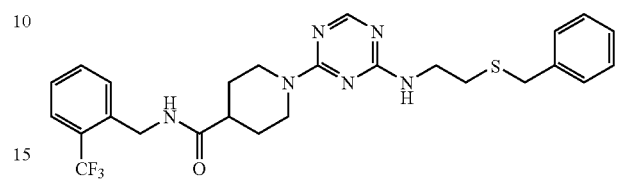

Example 12 was prepared using the general procedure described above in Example 10 substituting the appropriate starting materials. MS (ES+): m/e 530.8 [M]$^+$

Example 13

1-[4-(4-Methyl-1-piperazinyl)-1,3,5-triazin-2-yl]-N-{[2-(trifluoromethyl)phenyl]methyl}-4-piperidinecarboxamide

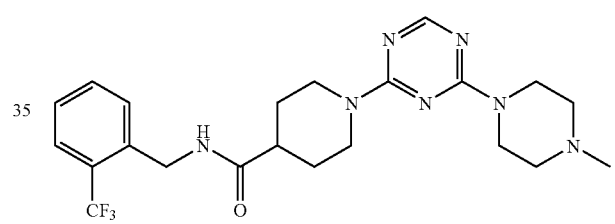

Example 13 was prepared using the general procedure described above in Example 10 substituting the appropriate starting materials. MS (ES+): m/e 464.4 [M+H]$^+$

Example 14

1-[4-(4-Morpholinyl)-1,3,5-triazin-2-yl]-N-{[2-(trifluoromethyl)phenyl]methyl}-4-piperidinecarboxamide

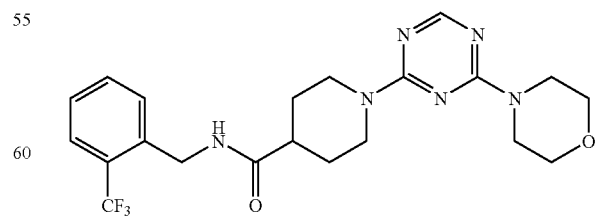

Example 14 was prepared using the general procedure described above in Example 10 substituting the appropriate starting materials. MS (ES+): m/e 451.5 [M+H]$^+$

Example 15

1-[4,6-Bis(4-methyl-1-piperazinyl)-1,3,5-triazin-2-yl]-N-{[2-(trifluoromethyl)phenyl]methyl}-4-piperidinecarboxamide

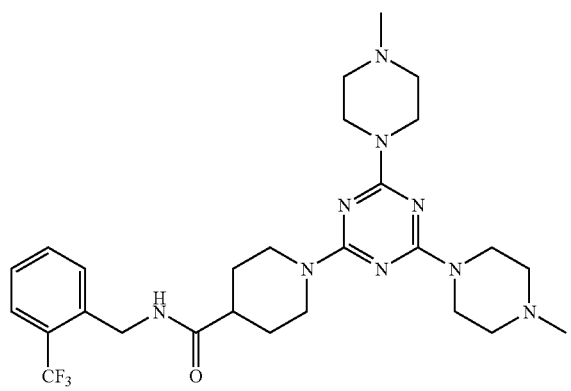

a) Preparation of 1-(4,6-dichloro-1,3,5-triazin-2-yl)-N-{[2-(trifluoromethyl)phenyl]methyl}-4-piperidinecarboxamide To a suspension of cyanuric chloride (1.00 g, 5.42 mmol, 1.00 equiv) in 1:1 CH$_3$CN:H$_2$O (9.0 mL) at 0° C. was added N-{[2-(trifluoromethyl)phenyl]methyl}-4-piperidinecarboxamide (1.55 g, 5.42 mmol, 1.00 equiv). This mixture was treated with 1 N NaOH to maintain a pH of 9-10, and the resulting suspension was stirred for 10 min at 0° C. This material was used in the next step without workup or purification. MS (ES+): m/e 433.8 [M+H]$^+$.

b) Preparation of 1-[4,6-bis(4-methyl-1-piperazinyl)-1,3,5-triazin-2-yl]-N-{[2-(trifluoromethyl)phenyl]methyl}-4-piperidinecarboxamide Approximately ⅕ of the mixture prepared in step a was transferred to a separate flask, where it was treated with N-methylpiperazine (1.20 mL, 54.2 mmol, 10.0 equiv). This mixture was heated at 80° C. for 10 min, and the resulting solution was filtered and purified by reverse-phase HPLC (Sunfire, 10-40% CH$_3$CN/H$_2$O, 0.1% TFA, 12 min) to provide 185 mg (30%) of the title compound. MS (ES+): m/e 562.3 [M+H]$^+$.

Example 16

1-(4,6-Bis{[(2R)-2-phenylpropyl]amino}-1,3,5-triazin-2-yl)-N-{[2-(trifluoromethyl)phenyl]methyl}-4-piperidinecarboxamide

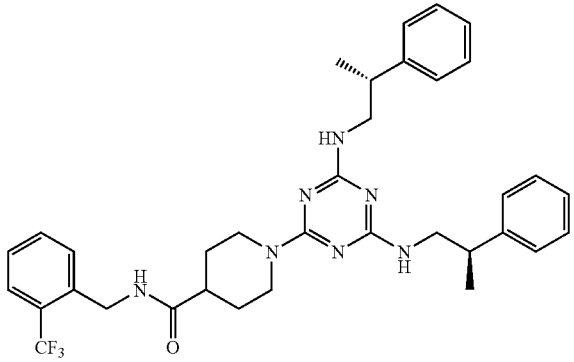

Example 16 was prepared using the general procedure described above in Example 15 substituting the appropriate starting materials. MS (ES+): m/e 632.3 [M+H]$^+$

Example 17

1-{4,6-Bis[[2-(dimethylamino)ethyl](methyl)amino]-1,3,5-triazin-2-yl}-N-{[2-(trifluoromethyl)phenyl]methyl}-4-piperidinecarboxamide

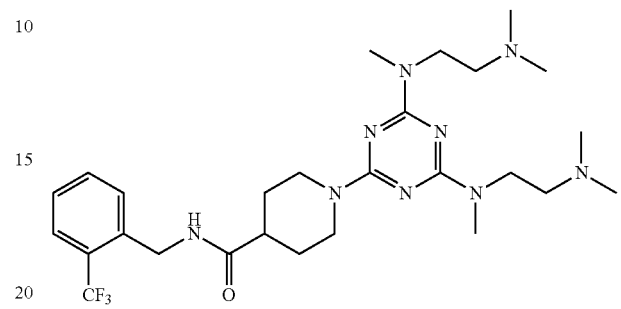

Example 17 was prepared using the general procedure described above in Example 15 substituting the appropriate starting materials. MS (ES+): m/e 566.3 [M+H]$^+$

Example 18

1-(4,6-Dihexahydro-1H-azepin-1-yl-1,3,5-triazin-2-yl)-N-{[2-(trifluoromethyl)phenyl]methyl}-4-piperidinecarboxamide

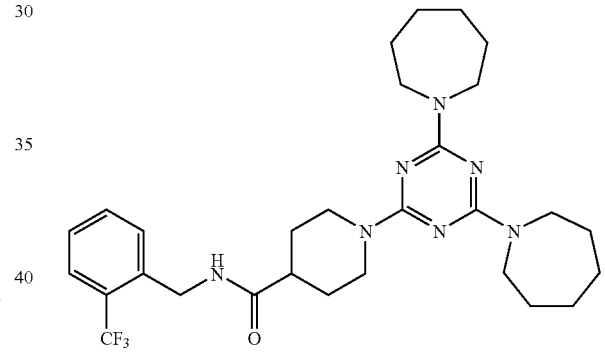

Example 18 was prepared using the general procedure described above in Example 15 substituting the appropriate starting materials. MS (ES+): m/e 560.3 [M+H]$^+$

Example 19

1-[4,6-Bis(methylamino)-1,3,5-triazin-2-yl]-N-{[2-(trifluoromethyl)phenyl]methyl}-4-piperidinecarboxamide

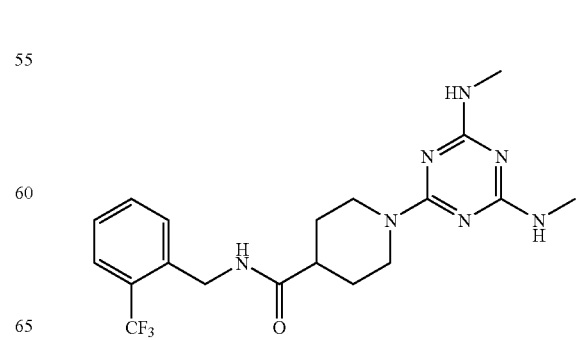

Example 19 was prepared using the general procedure described above in Example 15 substituting the appropriate starting materials. MS (ES+): m/e 424.2 [M+H]+

Example 20

1-[4-Hydroxy-6-(4-methyl-1-piperazinyl)-1,3,5-triazin-2-yl]-N-{[2-(trifluoromethyl)phenyl]methyl}-4-piperidinecarboxamide

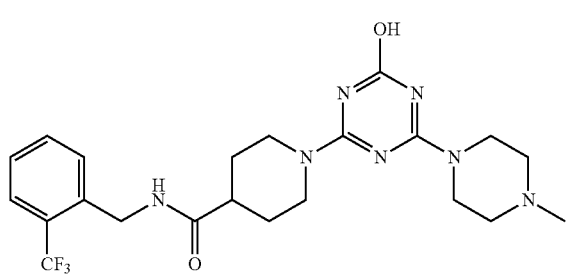

a) Preparation of 1-(4,6-dichloro-1,3,5-triazin-2-yl)-N-{[2-(trifluoromethyl)phenyl]methyl}-4-piperidinecarboxamide To a suspension of cyanuric chloride (500 mg, 2.71 mmol, 1.00 equiv) in 1:1 CH₃CN:H₂O (4.5 mL) at 0° C. was added N-{[2-(trifluoromethyl)phenyl]methyl}-4-piperidinecarboxamide (0.774 g, 2.71 mmol, 1.00 equiv). The solution was treated with 1 N NaOH to maintain a pH of 9-10 and stirred for 10 min at 0° C. The resulting suspension was used in the next step without workup or purification. MS (ES+): m/e 433.8 [M+H]+.

b) Preparation of 1-[4-chloro-6-(4-methyl-1-piperazinyl)-1,3,5-triazin-2-yl]-N-{[2-(trifluoromethyl)phenyl]methyl}-4-piperidinecarboxamide N-Methylpiperazine (0.31 mL, 2.7 mmol, 1.0 equiv) was added to the suspension prepared in step a. The resulting mixture was heated to 40° C. and treated with 1 N NaOH to maintain a pH of 9-10. The reaction mixture was stirred for 30 min and then used immediately in the next step without workup or purification. MS (ES+): m/e 498.1 [M+H]+.

c) Preparation of 1-[4-hydroxy-6-(4-methyl-1-piperazinyl)-1,3,5-triazin-2-yl]-N-{[2-(trifluoromethyl)phenyl]methyl}-4-piperidinecarboxamide To ⅕ of the suspension prepared in step b (0.542 mmol, 1.00 equiv) was added 6 N NaOH. The resulting mixture was heated to 80° C. for 1 h. The final solution was directly purified by reverse-phase HPLC (Sunfire, 20-40% CH₃CN, H₂O, 0.1% TFA, 12 min) to afford 21.2 mg of the title compound. MS (ES+): m/e 480.1 [M+H]+.

Example 21

1-[4-(Methoxy)-6-(4-methyl-1-piperazinyl)-1,3,5-triazin-2-yl]-N-{[2-(trifluoromethyl)phenyl]methyl}-4-piperidinecarboxamide

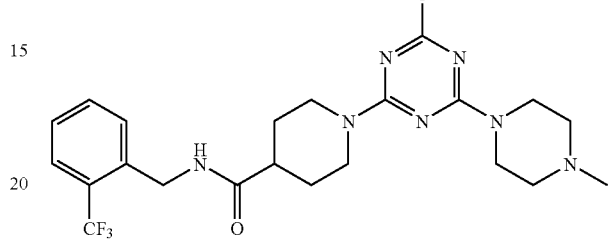

⅕ of the suspension prepared in step b of Example 20 (0.542 mmol, 1.00 equiv) was concentrated under reduced pressure. Then, sodium methoxide (1.24 mL of 25 wt % solution in MeOH, 5.42 mmol, 10.0 equiv) was added. The resulting mixture was heated to 80° C. for 1 h. The final solution was purified by reverse-phase HPLC (Sunfire, 20-40% CH₃CN, H₂O, 0.1% TFA, 12 min) to afford 12.2 mg of the title compound. MS (ES+): m/e 493.8 [M+H]+.

Example 22

1-[4-(4-Methyl-1-piperazinyl)-6-(methylthio)-1,3,5-triazin-2-yl]-N-{[2-(trifluoromethyl)phenyl]methyl}-4-piperidinecarboxamide

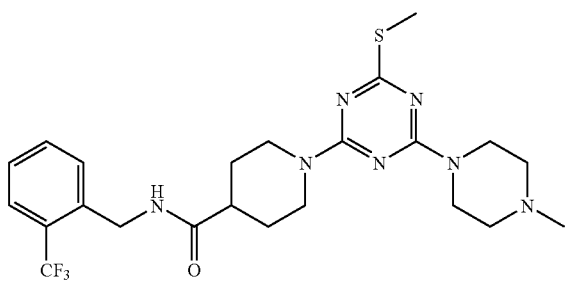

To ⅕ of the suspension prepared in step b of Example 20 (0.542 mmol, 1.00 equiv) was added NaSMe (380 mg, 5.42 mmol, 10.0 equiv) in EtOH (1.0 mL). The resulting mixture was heated to 80° C. for 1 h. The final solution was purified by reverse-phase HPLC (Sunfire, 20-50% CH₃CN, H₂O, 0.1% TFA, 12 min) to afford 27.9 mg of the title compound. MS (ES+): m/e 509.8 [M]+.

Example 23

1-[4-[(1-Methylethyl)amino]-6-(4-methyl-1-piperazinyl)-1,3,5-triazin-2-yl]-N-{[2-(trifluoromethyl)phenyl]methyl}-4-piperidinecarboxamide

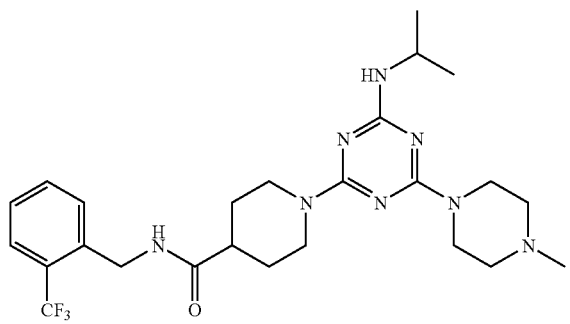

Example 23 was prepared using the general procedure described above in Example 20 substituting the appropriate starting materials. MS (ES+): m/e 520.9 [M]$^+$

Example 24

N-[(2,4-Dichlorophenyl)methyl]-1-[4-(methylamino)-6-(4-methyl-1-piperazinyl)-1,3,5-triazin-2-yl]-4-piperidinecarboxamide

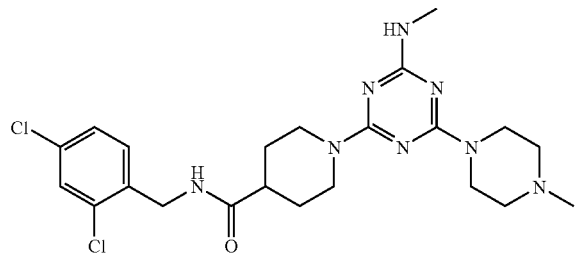

a) Preparation of 4,6-dichloro-N-methyl-1,3,5-triazin-2-amine

To a suspension of cyanuric chloride (3.00 g, 16.3 mmol, 1.00 equiv) in 1:1 CH$_3$CN:H$_2$O (27 mL) at 0° C. was added NH$_2$Me (2.0 M solution in THF, 8.13 mL, 16.3 mmol, 1.00 equiv). The mixture was treated with 1 N NaOH to maintain a pH of 9-10, and the resulting suspension was stirred for 5 min at 0° C. This material was used in the next step without workup or purification. MS (ES+): m/e 178.9 [M+H]$^+$.

b) Preparation of 1-[4-chloro-6-(methylamino)-1,3,5-triazin-2-yl]-4-piperidinecarboxylic acid 4-Piperidinecarboxylic acid (2.10 g, 16.3 mmol, 1.00 equiv) was added to the suspension prepared in step a. The resulting mixture was heated to 40° C. and treated with 1 N NaOH to maintain a pH of 9-10. The reaction mixture was stirred for 2 h at the same temperature and then used immediately in the next step without workup or purification. MS (ES+): m/e 428.9 [M+H]$^+$.

c) Preparation of 1-[4-(methylamino)-6-(4-methyl-1-piperazinyl)-1,3,5-triazin-2-yl]-4-piperidinecarboxylic acid The suspension prepared in step b was treated with N-methylpiperazine (18.0 mL, 163 mmol, 10.0 equiv). After refluxing at 80° C., the mixture was concentrated to a volume of ~10 mL and then purified by reverse-phase HPLC (Phenomenex, 1-15% CH$_3$CN/H$_2$O, 0.1% TFA, 12 min) gave 2.02 g (37%) of the desired compound. MS (ES+): m/e 336.0 [M+H]$^+$.

d) Preparation of N-[(2,4-dichlorophenyl)methyl]-1-[4-(methylamino)-6-(4-methyl-1-piperazinyl)-1,3,5-triazin-2-yl]-4-piperidinecarboxamide To a solution of 1-[4-(methylamino)-6-(4-methyl-1-piperazinyl)-1,3,5-triazin-2-yl]-4-piperidinecarboxylic acid (84 mg, 0.25 mmol, 1.0 equiv), [(2,4-dichlorophenyl)methyl]amine (44 µL, 0.31 mmol, 1.3 equiv), and diisopropylethylamine (DIEA, 70 µL, 0.38 mmol, 1.5 equiv) in DMF (1.6 mL) was added BOP (166 mg, 0.38 mmol, 1.5 equiv). The reaction mixture was stirred overnight at room temperature. The resulting solution was filtered and purified using reverse-phase HPLC (Sunfire, 10-45% CH$_3$CN/H$_2$O, 0.1% TFA, 12 min) to afford 28 mg (23%) of the title compound. MS (ES+): m/e 493.1 [M]$^+$.

Example 25

1-[4-(Methylamino)-6-(4-methyl-1-piperazinyl)-1,3,5-triazin-2-yl]-N-{[4-(trifluoromethyl)phenyl]methyl}-4-piperidinecarboxamide

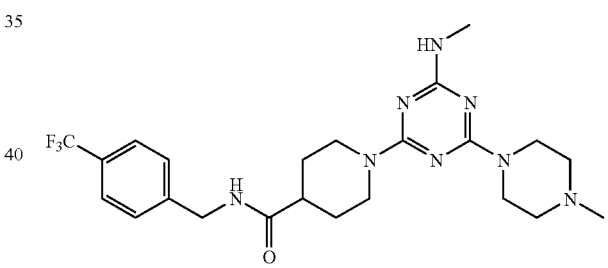

Example 25 was prepared using the general procedure described above in Example 24 substituting the appropriate starting materials. MS (ES+): m/e 493.1 [M+H]$^+$.

Example 26

1-[4-(Methylamino)-6-(4-methyl-1-piperazinyl)-1,3,5-triazin-2-yl]-N-({2-[(trifluoromethyl)oxy]phenyl}methyl)-4-piperidinecarboxamide

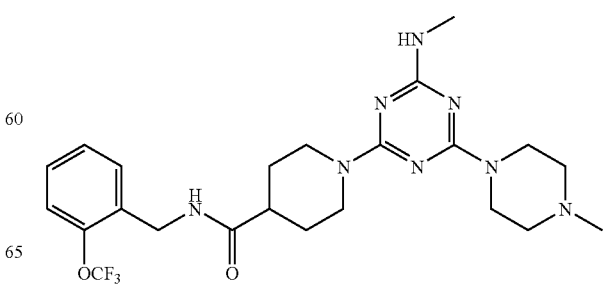

Example 26 was prepared using the general procedure described above in Example 24 substituting the appropriate starting materials. MS (ES+): m/e 509.2 [M+H]+.

Example 27

N-[(2-Chlorophenyl)methyl]-1-[4-(methylamino)-6-(4-methyl-1-piperazinyl)-1,3,5-triazin-2-yl]-4-piperidinecarboxamide99

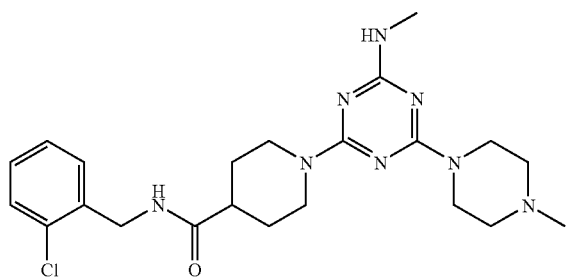

Example 27 was prepared using the general procedure described above in Example 24 substituting the appropriate starting materials. MS (ES+): m/e 459.1 [M+H].

Example 28

N-(Cyclohexylmethyl)-1-[4-(methylamino)-6-(4-methyl-1-piperazinyl)-1,3,5-triazin-2-yl]-4-piperidinecarboxamide

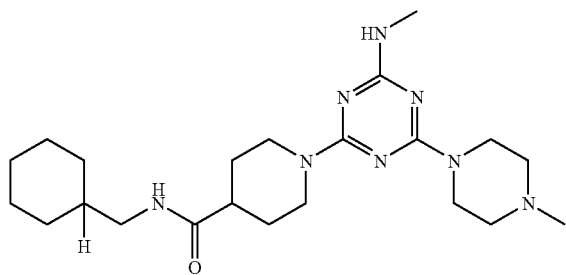

Example 28 was prepared using the general procedure described above in Example 24 substituting the appropriate starting materials. MS (ES+): m/e 431.2 [M+H]+.

Example 29

1-[4-(Methylamino)-6-(4-methyl-1-piperazinyl)-1,3,5-triazin-2-yl]-N-(2-pyridinylmethyl)-4-piperidinecarboxamide

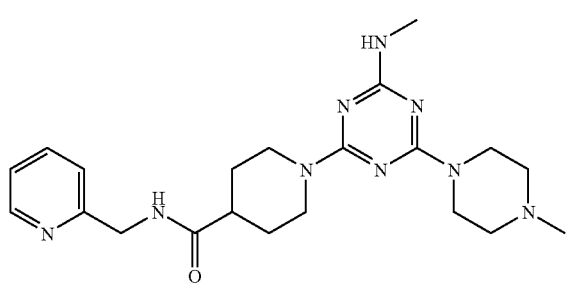

Example 29 was prepared using the general procedure described above in Example 24 substituting the appropriate starting materials. MS (ES+): m/e 426.1 [M+H]+.

Example 30

N-[(2-Trifluoro-phenyl)methyl)-benzyl]-1-[4-(methylamino)-6-(4-methyl-1-piperazinyl)-1,3,5-triazin-2-yl]-3-piperidinecarboxamide

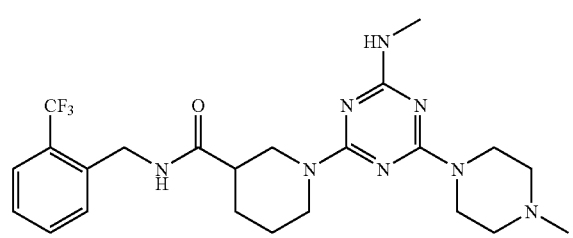

a) Preparation of 1-[4-(methylamino)-6-(4-methyl-1-piperazinyl)-1,3,5-triazin-2-yl]-3-piperidinecarboxylic acid To a suspension of cyanuric chloride (1.0 g, 4.1 mmol, 1.00 equiv) in 1:1 CH$_3$CN:H$_2$O at 0° C. was added NH$_2$Me (2.0 M solution in THF, 2.0 mL, 4.1 mmol, 1.00 equiv). The pH of the reaction mixture was adjusted to a pH of 8-9 by treating with 1 N NaOH. The pH was maintained between 8 and 9 for 30 min (reaction progress was monitored by LCMS). Next 3-piperidinecarboxylic acid (0.53 g, 4.1 mmol, 1.00 equiv) was added to the reaction mixture. The pH of the reaction mixture was again maintained between 8 and 9 using 1 N NaOH. Next N-methylpiperazine (4.0 mL, 41 mmol, 10.0 equiv) was added to the reaction mixture and the mixture was heated at reflux overnight. The reaction mixture was concentrated, the crude product was dissolved in a mixture of methanol and water, and purified by HPLC to provide 0.9 g of the title compound. MS (ES+): m/e 336.2 [M+H]+.

b) Preparation of N-[(2-trifluoromethyl-phenyl)methyl]-1-[4-(methylamino)-6-(4-methyl-1-piperazinyl)-1,3,5-triazin-2-yl]-3-piperidinecarboxamide A solution of 1-[4-(methylamino)-6-(4-methyl-1-piperazinyl)-1,3,5-triazin-2-yl]-3-piperidinecarboxylic acid (0.18 g, 0.55 mmol, 1.0 equiv), [(2-trifluoromethyl-phenyl)methyl]amine (0.12 g, 0.68 mmol, 1.25 equiv), and dimethylaminopyridine (DMAP, 14 mg, 0.11 mmol, 0.2 equiv) in CH$_2$Cl$_2$ and DMF was cooled to ~0° C. using an ice bath. Next EDCI (0.16 g, 0.82 mmol, 1.5 equiv) was added. The reaction mixture was stirred at 0° C. for 30 min and at room temperature for an additional 2 hours. The reaction was monitored by HPLC. The solution was then diluted with CH$_2$Cl$_2$ and washed with saturated aqueous NaCl. The organic layer was dried over Na$_2$SO$_4$, and concentrated to provide the crude product. The crude product was dissolved in methanol and purified by HPLC to afford 73 mg of the title compound. MS (ES+): m/e 493.3 [M+H]+.

Example 31

1-[4-(Methylamino)-6-(4-methyl-1-piperazinyl)-1,3,5-triazin-2-yl]-N-({2-[(trifluoromethyl)oxy]phenyl}methyl)-3-piperidinecarboxamide

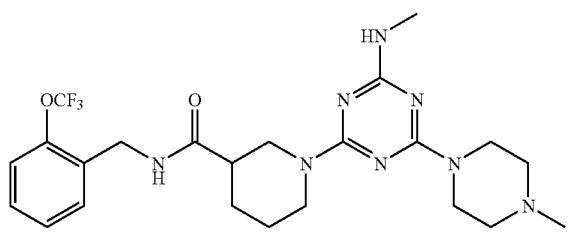

Example 31 was prepared using the general procedure described above in Example 30 substituting the appropriate starting materials. MS (ES+): m/e 509.3 [M+H]$^+$.

Example 32

N-[(2,4-Dichlorophenyl)methyl]-1-[4-(methylamino)-6-(4-methyl-1-piperazinyl)-1,3,5-triazin-2-yl]-3-piperidinecarboxamide

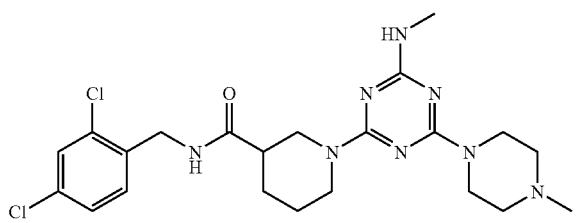

Example 32 was prepared using the general procedure described above in Example 30 substituting the appropriate starting materials. MS (ES+): m/e 493.2 [M]$^+$.

Example 33

1-[4-(Methylamino)-6-(4-methyl-1-piperazinyl)-1,3,5-triazin-2-yl]-N-{[2-(trifluoromethyl)phenyl]methyl}-3-pyrrolidinecarboxamide

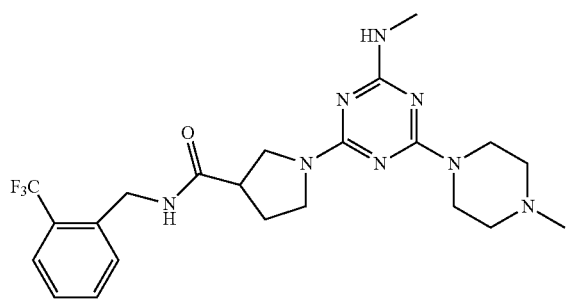

Example 33 was prepared using the general procedure described above in Example 30 substituting the appropriate starting materials. MS (ES+): m/e 479.3 [M+H]$^+$.

Example 34

1-[4-(Methylamino)-6-(4-methyl-1-piperazinyl)-1,3,5-triazin-2-yl]-N-({2-[(trifluoromethyl)oxy]phenyl}methyl)-3-pyrrolidinecarboxamide

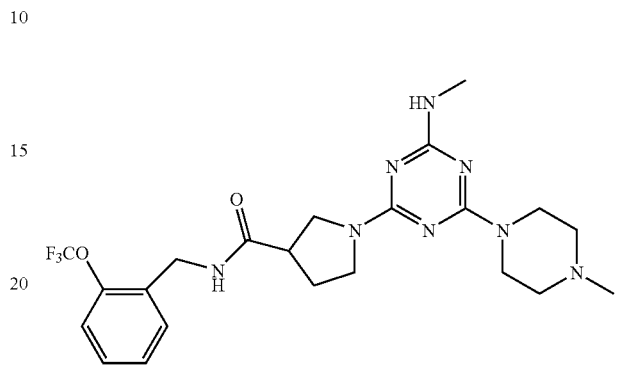

Example 34 was prepared using the general procedure described above in Example 30 substituting the appropriate starting materials. MS (ES+): m/e 495.1 [M+H]$^+$.

Example 35

2-{4-[4-(Methylamino)-6-(4-methyl-1-piperazinyl)-1,3,5-triazin-2-yl]-1-piperazinyl}-N-({2-[(trifluoromethyl)oxy]phenyl}methyl)acetamide

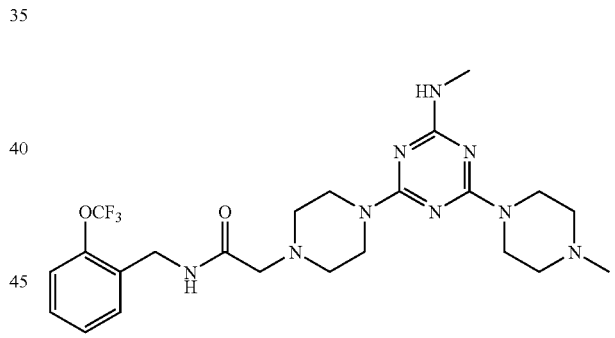

a) Preparation of 4,6-dichloro-N-methyl-1,3,5-triazin-2-amine

To a suspension of cyanuric chloride (1.00 g, 5.42 mmol, 1.00 equiv) in 1:1 CH$_3$CN:H$_2$O (9 mL) at 0° C. was added NH$_2$Me (2.0 M solution in THF, 2.71, 5.42 mmol, 1.00 equiv). The solution was treated with 1 N NaOH to maintain a pH of 9-10 and stirred for 5 min at 0° C. The resulting suspension was used in the next step without workup or purification. MS (ES+): m/e 179.0 [M+H]$^+$.

b) Preparation of Ethyl {4-[4-chloro-6-(methylamino)-1,3,5-triazin-2-yl]-1-piperazinyl}acetate Ethyl 1-piperazinylacetate (933 mg, 5.42 mmol, 1.00 equiv) was added to the suspension prepared in step a. The resulting mixture was heated to 40° C. and treated with 1 N NaOH to maintain a pH of 9-10. The reaction mixture was stirred for 30 min and then used immediately in the next step without workup or purification. MS (ES+): m/e 315.0 [M+H]⁺.

c) Preparation of ethyl {4-[4-(methylamino)-6-(4-methyl-1-piperazinyl)-1,3,5-triazin-2-yl]-1-piperazinyl}acetate N-Me-piperazine (6.00 mL, 54.2 mmol, 10.0 equiv) was added to the suspension obtained in step b. The reaction mixture was stirred at 80° C. for 1 h, and the resulting solution was used in the next step without workup or purification. MS (ES+): m/e 379.1 [M+H]⁺.

d) Preparation of {4-[4-(methylamino)-6-(4-methyl-1-piperazinyl)-1,3,5-triazin-2-yl]-1-piperazinyl}acetic acid To the solution prepared in step c was added 6 N NaOH (6 mL), and the resulting mixture was heated to 60° C. overnight. The reaction mixture was cooled to room temperature, and purified directly (without concentrating or work up) using reverse-phase HPLC (Phenomenex, 2-15% CH₃CN/H₂O, 0.1% TFA, 6 min) to afford 0.95 g (50%) of the title compound. MS (ES+): m/e 351.1 [M+H]⁺.

e) Preparation of 2-{4-[4-(methylamino)-6-(4-methyl-1-piperazinyl)-1,3,5-triazin-2-yl]-1-piperazinyl}-N-({2-[(trifluoromethyl)oxy]phenyl}methyl)acetamide To a solution of {-4-[4-(methylamino)-6-(4-methyl-1-piperazinyl)-1,3,5-triazin-2-yl]-1-piperazinyl}acetic acid (100 mg, 0.286 mmol, 1.00 equiv), {[2-(trifluoromethyl)phenyl]methyl}amine (48 μL, 0.34 mmol, 1.2 equiv), and diisopropylethylamine (DIEA, 75 μL, 0.43 mmol, 1.5 equiv) in DMF (1.8 mL) was added BOP (190 mg, 0.43 mmol, 1.5 equiv). The reaction mixture was stirred at room temperature for 1 h. The reaction mixture was filtered and purified by reverse-phase HPLC (Sunfire, 10-80% CH₃CN/H₂O, 0.1% TFA, 15 min) to give 30 mg (20%) of the title compound. MS (ES+): m/e 524.2 [M+H]⁺.

Example 36

2-{4-[4-(Methylamino)-6-(4-methyl-1-piperazinyl)-1,3,5-triazin-2-yl]-1-piperazinyl}-N-{[2-(trifluoromethyl)phenyl]methyl}acetamide

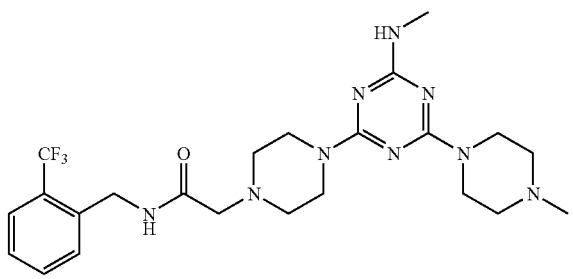

Example 36 was prepared using the general procedure described above in Example 35 substituting the appropriate starting materials. MS (ES+): m/e 508.3 [M+H]⁺.

Example 37

N-[(2,4-Dichlorophenyl)methyl]-2-{4-[4-(methylamino)-6-(4-methyl-1-piperazinyl)-1,3,5-triazin-2-yl]-1-piperazinyl}acetamide

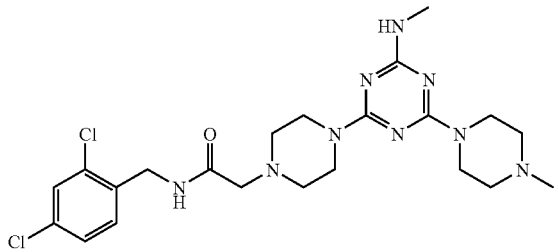

Example 37 was prepared using the general procedure described above in Example 35 substituting the appropriate starting materials. MS (ES+): m/e 508.2 [M]⁺.

Example 38

4-[4-(Methylamino)-6-(4-methyl-1-piperazinyl)-1,3,5-triazin-2-yl]-N-{[2-(trifluoromethyl)phenyl]methyl}-1-piperazinecarboxamide

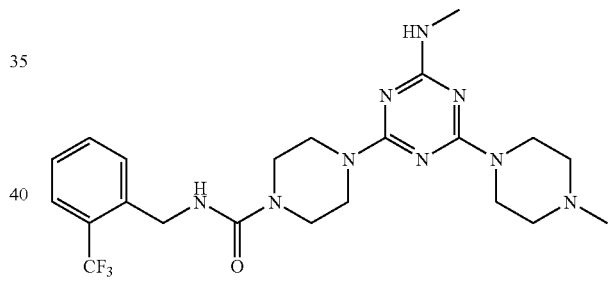

a) Preparation of N-methyl-4-(4-methyl-1-piperazinyl)-6-(1-piperazinyl)-1,3,5-triazin-2-amine To a suspension of cyanuric chloride (3.00 g, 16.3 mmol, 1.00 equiv) in 1:1 CH₃CN:H₂O (27 mL) at 0° C. was added NH₂Me (2.0 M solution in THF, 8.13, 16.3 mmol, 1.00 equiv). The solution was treated with 1 N NaOH to maintain a pH of 9-10 and stirred for 5 min at 0° C. N-Me-piperazine (1.80 mL, 16.3 mmol, 1.00 equiv) was added to the suspension. The resulting mixture was heated to 40° C. and treated with 1 N NaOH to maintain a pH of 9-10. The reaction mixture was stirred for 30 min. piperazine (14.1 g, 163 mmol, 10.0 equiv) was added to the suspension. The reaction mixture was stirred at 80° C., and the resulting solution was concentrated under reduced pressure to half the volume. The solution was acidified with 6 N HCl and the precipitate that formed was collected by filtration. The precipitate was next dissolved in water, and the aqueous solution was purified directly via reverse-phase HPLC (Phenomenex, 1-5% CH₃CN/H₂O, 0.1% TFA, 25 min) to afford 1.20 g (25%) of the title compound. MS (ES+): m/e 293.1 [M+H]⁺.

b) Preparation of 4-[4-(methylamino)-6-(4-methyl-1-piperazinyl)-1,3,5-triazin-2-yl]-N-{[2-(trifluoromethyl)phenyl]methyl}-1-piperazinecarboxamide 4-Nitrophenyl chloridocarbonate (60 mg, 0.30 mmol, 1.1 equiv) and triethylamine (0.14 mL, 1.0 mmol, 3.5 equiv) were dissolved in CH$_2$Cl$_2$ (3.0 mL). A solution of {[2-(trifluoromethyl)phenyl]methyl}amine (40 µL, 0.29 mmol, 1.0 equiv) in CH$_2$Cl$_2$ (2.0 mL) was added dropwise over 10 min. This mixture was stirred at room temperature for 15 min. A solution of N-methyl-4-(4-methyl-1-piperazinyl)-6-(1-piperazinyl)-1,3,5-triazin-2-amine (100 mg, 0.342 mmol, 1.20 equiv) in CH$_2$Cl$_2$ (1.0 mL) was added, followed by triethylamine (0.20 mL, 1.4 mmol, 5.0 equiv). After stirring the reaction mixture for 15 min, the solvent was removed in vacuo and the residue was purified by reverse-phase HPLC to afford 14 mg (10%) of the title compound. MS (ES+): m/e 494.2 [M+H]$^+$.

Example 39

4-[4-(Methylamino)-6-(4-methyl-1-piperazinyl)-1,3,5-triazin-2-yl]-N-({2-[(trifluoromethyl)oxy]phenyl}methyl)-1-piperazinecarboxamide

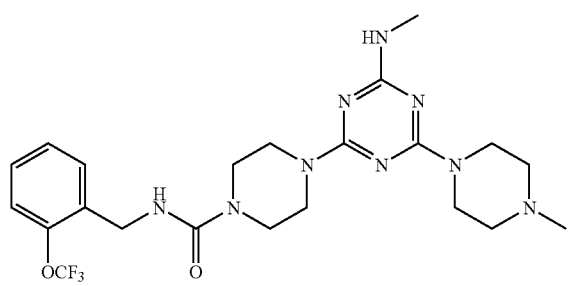

Example 39 was prepared using the general procedure described above in Example 38 substituting the appropriate starting materials. MS (ES+): m/e 510.2 [M+H]$^+$.

Example 40

1-[4-(Methylamino)-6-(2-methylphenyl)-1,3,5-triazin-2-yl]-N-{[2-(trifluoromethyl)phenyl]methyl}-4-piperidinecarboxamide

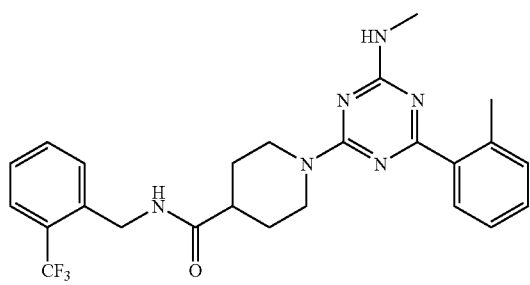

To a suspension of 1-[4-chloro-6-(methylamino)-1,3,5-triazin-2-yl]-N-{[2-(trifluoromethyl)phenyl]methyl}-4-piperidinecarboxamide (Intermediate 7d, 75 mg, 0.17 mmol, 1.0 equiv), (2-methylphenyl)boronic acid (29 mg, 0.21 mmol, 1.2 equiv), and Na$_2$CO$_3$ (37 mg, 0.35 mmol, 2.0 equiv) in 3:1 CH$_3$CN:H$_2$O was added Pd(PPh$_3$)$_4$ (10 mg, 0.0088 mmol, 0.05 equiv). The reaction mixture was heated at 90° C. for 1 h. The resulting suspension was filtered through an SCX resin (55 □m, 70 A, 2 g/12 mL giga tubes) using MeOH, and the product was recovered by eluting with 2.0 M NH$_3$ in MeOH. The filtrate was concentrated, and the resulting residue was purified using reverse-phase HPLC (XBridge, 10-80% CH$_3$CN/H$_2$O, 0.1% TFA, 12 min) to afford 25 mg (30%) of the title compound. MS (ES+): m/e 485.2 [M+H]$^+$.

Example 41

1-{4-(Methylamino)-6-[4-(trifluoromethyl)phenyl]-1,3,5-triazin-2-yl}-N-{[2-(trifluoromethyl)phenyl]methyl}-4-piperidinecarboxamide

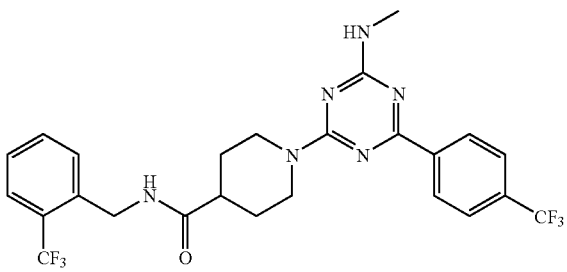

Example 41 was prepared using the general procedure described above in Example 40 substituting the appropriate starting materials. MS (ES+): m/e 539.2 [M+H]$^+$.

Example 42

1-[4-[4-(Acetylamino)phenyl]-6-(methylamino)-1,3,5-triazin-2-yl]-N-{[2-(trifluoromethyl)phenyl]methyl}-4-piperidinecarboxamide

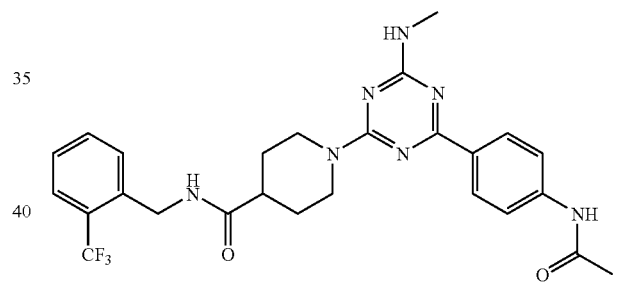

Example 42 was prepared using the general procedure described above in Example 40 substituting the appropriate starting materials. MS (ES+): m/e 527.9 [M+H]$^+$.

Example 43

1-[4-[4-(Dimethylamino)phenyl]-6-(methylamino)-1,3,5-triazin-2-yl]-N-{[2-(trifluoromethyl)phenyl]methyl}-4-piperidinecarboxamide

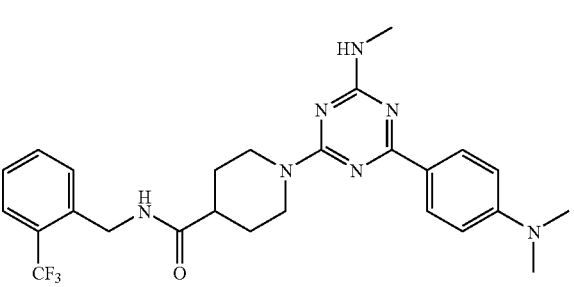

Example 43 was prepared using the general procedure described above in Example 40 substituting the appropriate starting materials. MS (ES+): m/e 514.2 [M+H]$^+$.

Example 44

1-{4-(Methylamino)-6-[3-(trifluoromethyl)phenyl]-1,3,5-triazin-2-yl}-N-{[2-(trifluoromethyl)phenyl]methyl}-4-piperidinecarboxamide

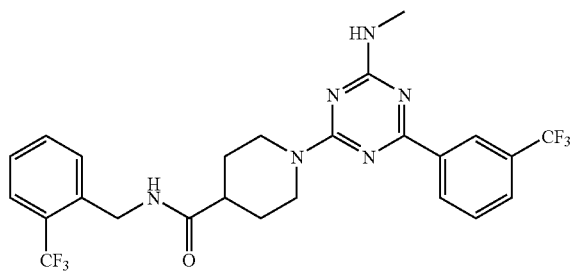

Example 44 was prepared using the general procedure described above in Example 40 substituting the appropriate starting materials. MS (ES+): m/e 538.9 [M+H]$^+$.

Example 45

1-[4-(2-Chlorophenyl)-6-(methylamino)-1,3,5-triazin-2-yl]-N-{[2-(trifluoromethyl)phenyl]methyl}-4-piperidinecarboxamide

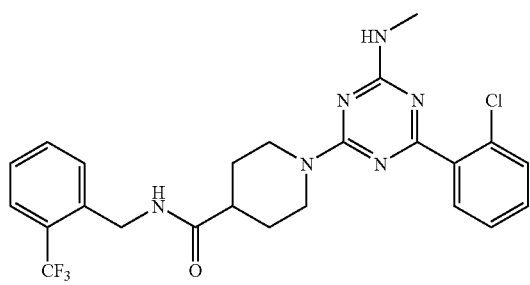

Example 45 was prepared using the general procedure described above in Example 40 substituting the appropriate starting materials. MS (ES+): m/e 505.1 [M+H]$^+$.

Example 46

1-[4-(3-Chlorophenyl)-6-(methylamino)-1,3,5-triazin-2-yl]-N-{[2-(trifluoromethyl)phenyl]methyl}-4-piperidinecarboxamide

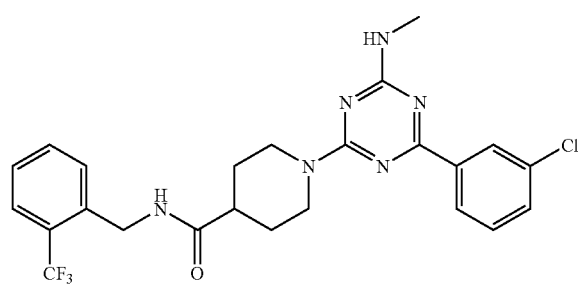

Example 46 was prepared using the general procedure described above in Example 40 substituting the appropriate starting materials. MS (ES+): m/e 505.1 [M+H]$^+$.

Example 47

1-[4-(3-Fluorophenyl)-6-(methylamino)-1,3,5-triazin-2-yl]-N-{[2-(trifluoromethyl)phenyl]methyl}-4-piperidinecarboxamide

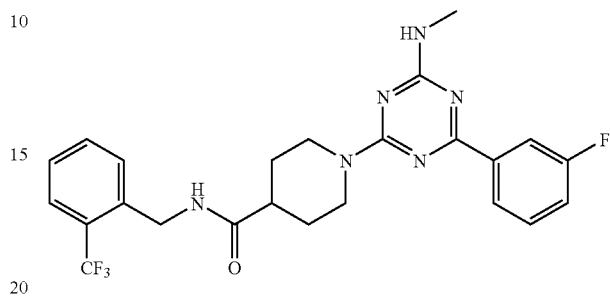

Example 47 was prepared using the general procedure described above in Example 40 substituting the appropriate starting materials. MS (ES+): m/e 489.2 [M+H]$^+$.

Example 48

1-[4-(4-Fluorophenyl)-6-(methylamino)-1,3,5-triazin-2-yl]-N-{[2-(trifluoromethyl)phenyl]methyl}-4-piperidinecarboxamide

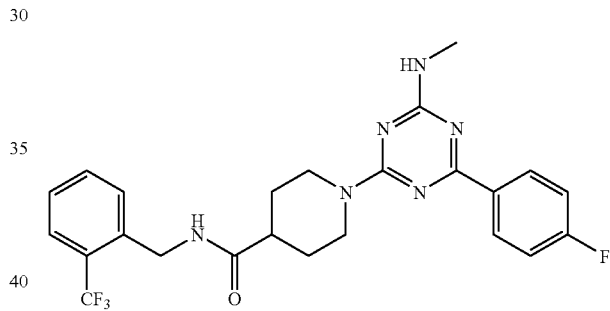

Example 48 was prepared using the general procedure described above in Example 40 substituting the appropriate starting materials. MS (ES+): m/e 489.1 [M+H]$^+$.

Example 49

1-{4-(Methylamino)-6-[2-(methoxy)phenyl]-1,3,5-triazin-2-yl}-N-{[2-(trifluoromethyl)phenyl]methyl}-4-piperidinecarboxamide

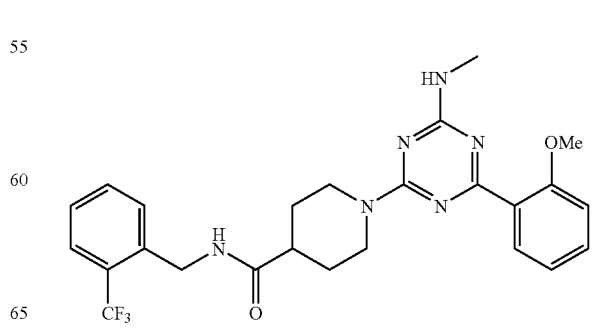

Example 49 was prepared using the general procedure described above in Example 40 substituting the appropriate starting materials. MS (ES+): m/e 501.3 [M+H]⁺.

Example 50

1-[4-[2,4-Bis(methoxy)phenyl]-6-(methylamino)-1,3,5-triazin-2-yl]-N-{[2-(trifluoromethyl)phenyl]methyl}-4-piperidinecarboxamide

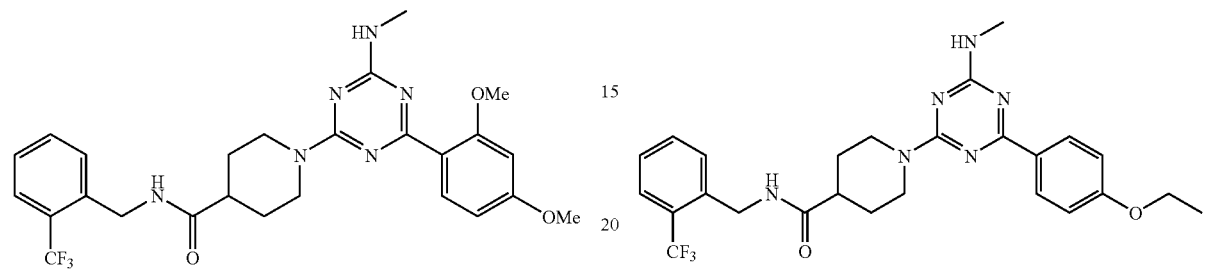

Example 50 was prepared using the general procedure described above in Example 40 substituting the appropriate starting materials. MS (ES+): m/e 531.2 [M+H]⁺.

Example 51

1-[4-(2,6-Dimethylphenyl)-6-(methylamino)-1,3,5-triazin-2-yl]-N-{[2-(trifluoromethyl)phenyl]methyl}-4-piperidinecarboxamide

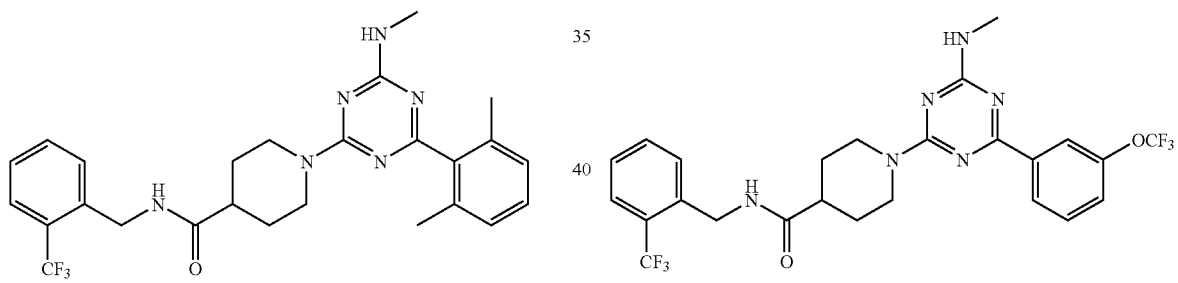

Example 51 was prepared using the general procedure described above in Example 40 substituting the appropriate starting materials. MS (ES+): m/e 499.1 [M+H]⁺.

Example 52

1-{4-(Methylamino)-6-[3-(methoxy)phenyl]-1,3,5-triazin-2-yl}-N-{[2-(trifluoromethyl)phenyl]methyl}-4-piperidinecarboxamide

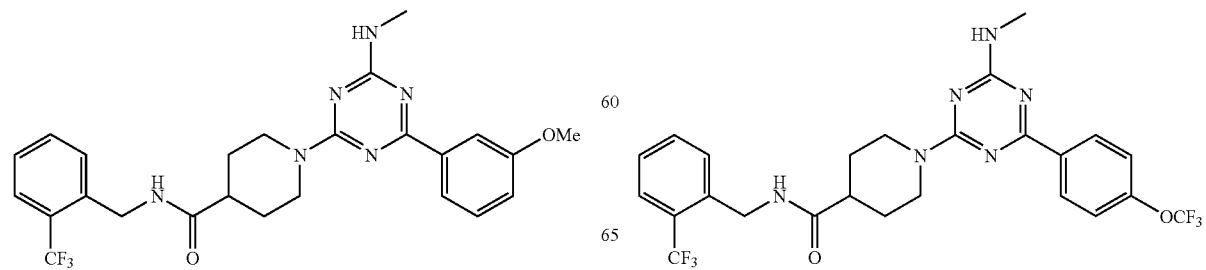

Example 52 was prepared using the general procedure described above in Example 40 substituting the appropriate starting materials. MS (ES+): m/e 500.9 [M+H]⁺.

Example 53

1-[4-[4-(Ethoxy)phenyl]-6-(methylamino)-1,3,5-triazin-2-yl]-N-{[2-(trifluoromethyl)phenyl]methyl}-4-piperidinecarboxamide

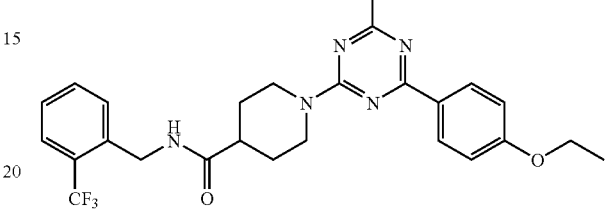

Example 53 was prepared using the general procedure described above in Example 40 substituting the appropriate starting materials. MS (ES+): m/e 515.1 [M+H]⁺.

Example 54

1-(4-(Methylamino)-6-{3-[(trifluoromethyl)oxy]phenyl}-1,3,5-triazin-2-yl)-N-{[2-(trifluoromethyl)phenyl]methyl}-4-piperidinecarboxamide

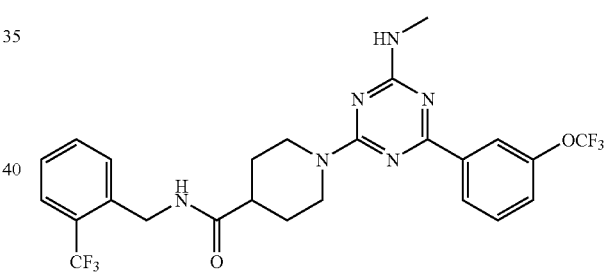

Example 54 was prepared using the general procedure described above in Example 40 substituting the appropriate starting materials. MS (ES+): m/e 555.0 [M+H]⁺.

Example 55

1-(4-(Methylamino)-6-{4-[(trifluoromethyl)oxy]phenyl}-1,3,5-triazin-2-yl)-N-{[2-(trifluoromethyl)phenyl]methyl}-4-piperidinecarboxamide

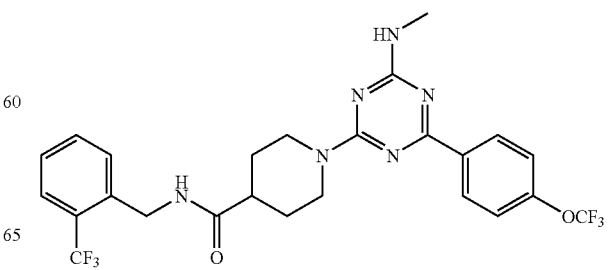

Example 55 was prepared using the general procedure described above in Example 40 substituting the appropriate starting materials. MS (ES+): m/e 555.0 [M+H]⁺.

Example 56

1-[4-[3-Chloro-4-(ethoxy)phenyl]-6-(methylamino)-1,3,5-triazin-2-yl]-N-{[2-(trifluoromethyl)phenyl]methyl}-4-piperidinecarboxamide

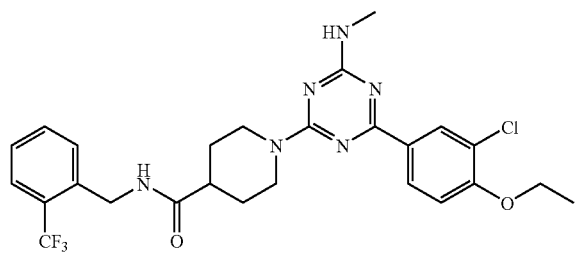

Example 56 was prepared using the general procedure described above in Example 40 substituting the appropriate starting materials. MS (ES+): m/e 548.9 [M]⁺.

Example 57

1-[4-[3-(Dimethylamino)phenyl]-6-(methylamino)-1,3,5-triazin-2-yl]-N-{[2-(trifluoromethyl)phenyl]methyl}-4-piperidinecarboxamide

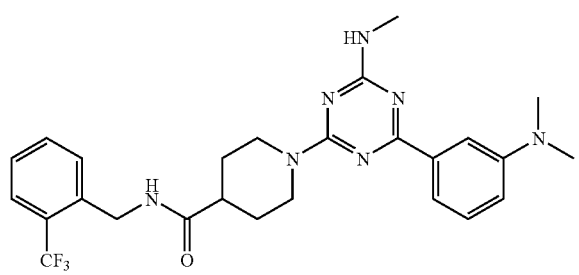

Example 57 was prepared using the general procedure described above in Example 40 substituting the appropriate starting materials. MS (ES+): m/e 514.1 [M+H]⁺.

Example 58

1-[4-(Methylamino)-6-(3-pyridinyl)-1,3,5-triazin-2-yl]-N-{[2-(trifluoromethyl)phenyl]methyl}-4-piperidinecarboxamide

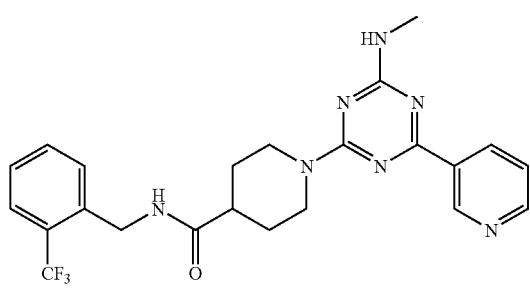

Example 58 was prepared using the general procedure described above in Example 40 substituting the appropriate starting materials. MS (ES+): m/e 471.9 [M+H]⁺.

Example 59

1-[4-(Methylamino)-6-(4-pyridinyl)-1,3,5-triazin-2-yl]-N-{[2-(trifluoromethyl)phenyl]methyl}-4-piperidinecarboxamide

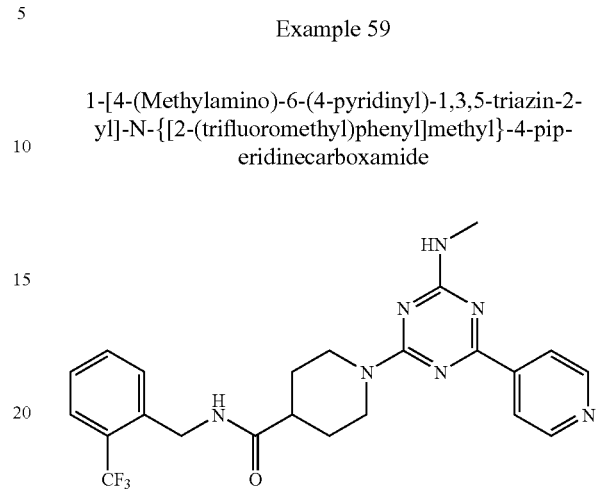

Example 59 was prepared using the general procedure described above in Example 40 substituting the appropriate starting materials. MS (ES+): m/e 471.9 [M+H]⁺.

Example 60

1-{4-(Methylamino)-6-[4-(methoxy)phenyl]-1,3,5-triazin-2-yl}-N-{[2-(trifluoromethyl)phenyl]methyl}-4-piperidinecarboxamide

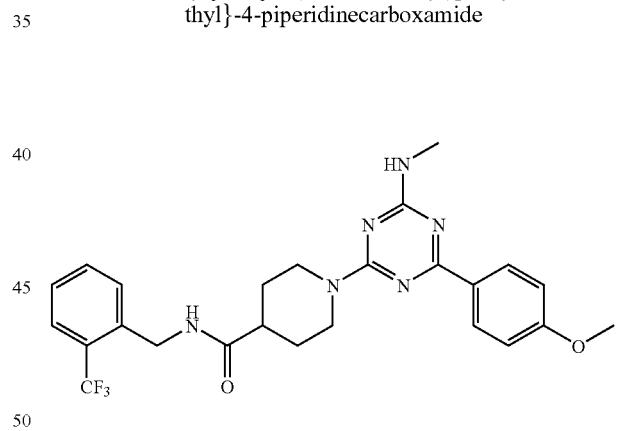

In a microwave vial, to a 1,4-dioxane (3.0 ml) suspension of 1-[4-chloro-6-(methylamino)-1,3,5-triazin-2-yl]-N-{[2-(trifluoromethyl)phenyl]methyl}-4-piperidine carboxamide (Intermediate 7d, 75 mg, 0.17 mmol, 1.0 equiv) was added (2-methylphenyl)boronic acid (29 mg, 0.21 mmol, 1.2 equiv), $Na_2CO_3$ (37 mg, 0.35 mmol, 2.0 equiv) in 3:1 $CH_3CN:H_2O$, and lastly Pd(PPh₃)₄ (10 mg, 0.0088 mmol, 0.05 equiv). The reaction mixture was heated at 150° C. for 25 minutes. The resulting suspension was diluted with ethyl acetate (10 ml), washed with water (5 ml), dried with sodium sulfate, filtered and concentrated under reduced pressure. The residue was taken up in 2.0 ml DMSO and purified via reverse-phase HPLC purification to afford the title compound. MS (ES+): m/e 501.0 [M+H]⁺.

Example 61

1-{4-(Methylamino)-6-[3-(methyloxy)phenyl]-1,3,5-triazin-2-yl}-N-{[2-(trifluoromethyl)phenyl]methyl}-4-piperidinecarboxamide

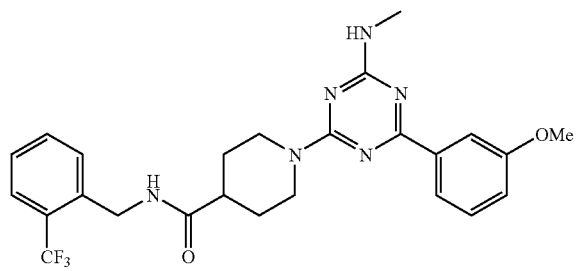

Example 61 was prepared using the general procedure described above in Example 60 substituting the appropriate starting materials. MS (ES+): m/e 501.0 [M+H]$^+$.

Example 62

1-[4-[4-(Ethoxy)phenyl]-6-(methylamino)-1,3,5-triazin-2-yl]-N-{[2-(trifluoromethyl)phenyl]methyl}-4-piperidinecarboxamide

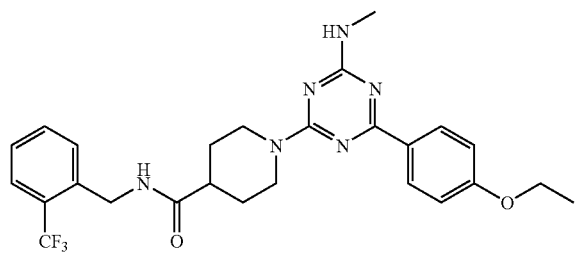

Example 62 was prepared using the general procedure described above in Example 60 substituting the appropriate starting materials. MS (ES+): m/e 515.2 [M+H]$^+$.

Example 63

1-[4-(3-Cyanophenyl)-6-(methylamino)-1,3,5-triazin-2-yl]-N-{[2-(trifluoromethyl)phenyl]methyl}-4-piperidinecarboxamide

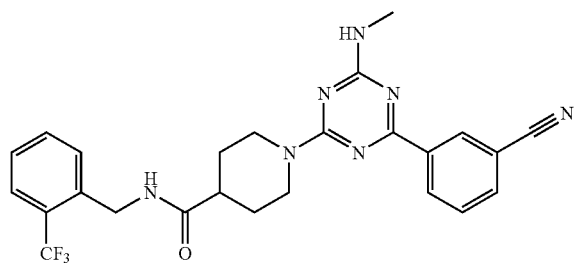

Example 63 was prepared using the general procedure described above in Example 60 substituting the appropriate starting materials. MS (ES+): m/e 496.1 [M+H]$^+$.

Example 64

1-[4-(4-Cyanophenyl)-6-(methylamino)-1,3,5-triazin-2-yl]-N-{[2-(trifluoromethyl)phenyl]methyl}-4-piperidinecarboxamide

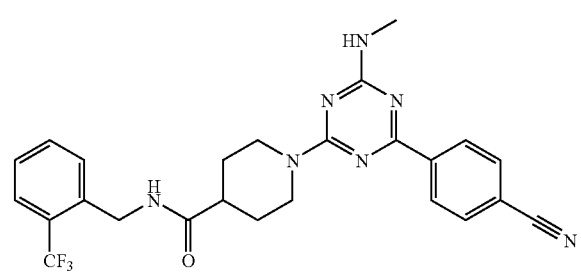

Example 64 was prepared using the general procedure described above in Example 60 substituting the appropriate starting materials. MS (ES+): m/e 496.1 [M+H]$^+$.

Example 65

1-{4-(Methylamino)-6-[4-(methylsulfonyl)phenyl]-1,3,5-triazin-2-yl}-N-{[2-(trifluoromethyl)phenyl]methyl}-4-piperidinecarboxamide

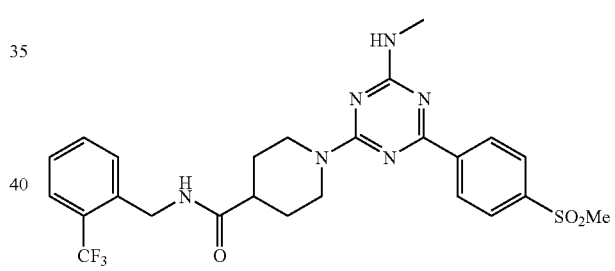

Example 65 was prepared using the general procedure described above in Example 60 substituting the appropriate starting materials. MS (ES+): m/e 549.0 [M+H]$^+$.

Example 66

1-[4-[4-(Ethylsulfonyl)phenyl]-6-(methylamino)-1,3,5-triazin-2-yl]-N-{[2-(trifluoromethyl)phenyl]methyl}-4-piperidinecarboxamide

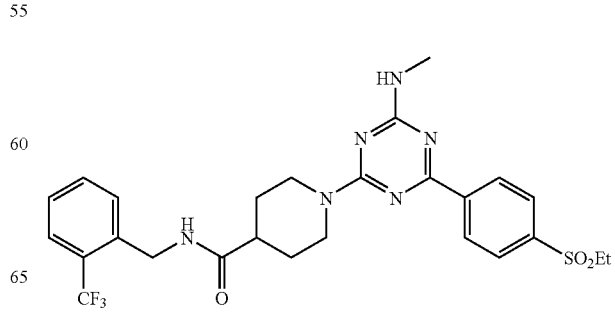

Example 66 was prepared using the general procedure described above in Example 60 substituting the appropriate starting materials. MS (ES+): m/e 563.3 [M+H]+.

Example 67

1-[4-(2-Fluorophenyl)-6-(methylamino)-1,3,5-triazin-2-yl]-N-{[2-(trifluoromethyl)phenyl]methyl}-4-piperidinecarboxamide

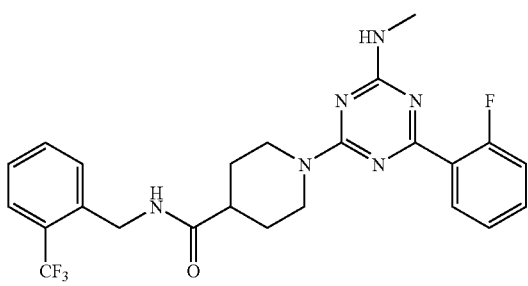

Example 67 was prepared using the general procedure described above in Example 60 substituting the appropriate starting materials. MS (ES+): m/e 489.1 [M+H]+.

Example 68

1-(4-(Methylamino)-6-{4-[(trifluoromethyl)oxy]phenyl}-1,3,5-triazin-2-yl)-N-{[2-(trifluoromethyl)phenyl]methyl}-4-piperidinecarboxamide

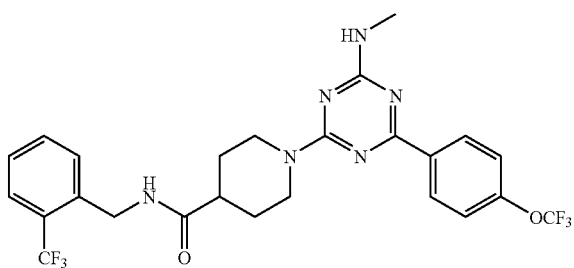

Example 68 was prepared using the general procedure described above in Example 60 substituting the appropriate starting materials. MS (ES+): m/e 555.0 [M+H]+.

Example 69

1-(4-(Methylamino)-6-{3-[(trifluoromethyl)oxy]phenyl}-1,3,5-triazin-2-yl)-N-{[2-(trifluoromethyl)phenyl]methyl}-4-piperidinecarboxamide

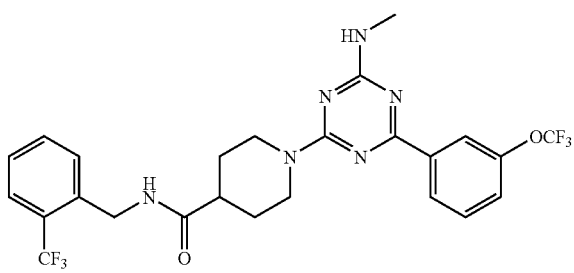

Example 69 was prepared using the general procedure described above in Example 60 substituting the appropriate starting materials. MS (ES+): m/e 555.0 [M+H]+.

Example 70

1-[4-Methyl-6-(methylamino)-1,3,5-triazin-2-yl]-N-{[2-(trifluoromethyl)phenyl]methyl}-4-piperidinecarboxamide

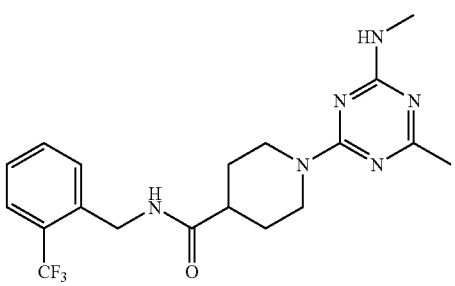

a) Preparation of 2,4-dichloro-6-methyl-1,3,5-triazine

Methylmagnesium bromide (9.00 mL of a 3.0 M solution in Et₂O, 27.1 mmol, 1.00 equiv) was added dropwise over 1 h to a cooled (0° C.) solution of cyanuric chloride (5.00 g, 27.1 mmol, 1.00 equiv) in THF (270 mL). The reaction mixture was stirred at room temperature overnight and was then quenched with sat NH₄Cl (aq). The aqueous layer was extracted 3 times using ethyl acetate, and the combined organic layers were dried over Na₂SO₄, filtered, and concentrated. The residue was purified using silica gel chromatography (0-40% CH₂Cl₂/hexanes) to afford 1.5 g (34%) of the title compound. MS (ES+): m/e 164.0 [M+H]+.

b) Preparation of 1-(4-chloro-6-methyl-1,3,5-triazin-2-yl)-N-{[2-(trifluoromethyl)phenyl]methyl}-4-piperidinecarboxamide To a solution of 2,4-dichloro-6-methyl-1,3,5-triazine (1.5 g, 9.1 mmol, 1.0 equiv) dissolved in CH₃CN (57 mL) was added {[2-(trifluoromethyl)phenyl]methyl}amine (2.6 g, 9.1 mmol, 1.0 equiv) and diisopropylethylamine (4.78 mL, 27.4 mmol, 3.00 equiv). The reaction mixture was stirred at room temperature for 30 min, and the resulting suspension was used in the next step without workup or purification. MS (ES+): m/e 414.1 [M+H]+.

c) Preparation of 1-[4-methyl-6-(methylamino)-1,3,5-triazin-2-yl]-N-{[2-(trifluoromethyl)phenyl]methyl}-4-piperidinecarboxamide Methylamine (23.0 mL of a 2.0 M solution in THF, 45.7 mmol, 5.00 equiv) was added to the suspension prepared above in step 70b, and the reaction mixture was heated at 40° C. for 1 h. The solvent was removed in vacuo, and the residue was purified by reverse-phase HPLC (Phenomenex, 10-55% CH₃CN/H₂O, 0.1% TFA, 12 min) to afford 1.67 g (43%) of the title compound. MS (ES+): m/e 409.1 [M+H]+.

Example 70 was also prepared using the general procedure described below for Example 83 substituting the appropriate starting materials. MS (ES+): m/e 409.1 [M+H]⁺.

Example 71

1-(4-Amino-6-methyl-1,3,5-triazin-2-yl)-N-{[2-(trifluoromethyl)phenyl]methyl}-4-piperidinecarboxamide

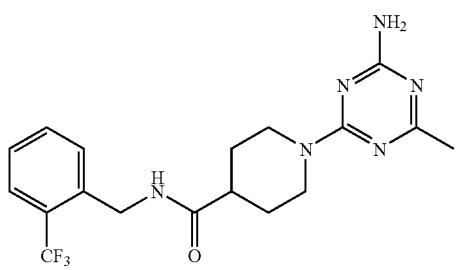

a) Preparation of 2,4-dichloro-6-methyl-1,3,5-triazine

To a THF (8 ml) solution of 2,4,6-trichloro-1,3,5-triazine (300 mg, 1.63 mmol, 1.00 equiv) at 0° C., methylmagnesium bromide (0.596 ml, 1.79 mmol, 1.10 equiv) was added. The reaction was allowed to warm to room temperature and stirring was continued overnight. The reaction was quenched by addition of water. The product was extracted with ethyl acetate; washed with sat sodium chloride; dried with sodium sulfate; filtered and concentrated under reduced pressure to afford the title compound. The crude product was carried forward. MS (ES+): m/e 186.1 [M+Na]⁺.

b) Preparation of 1-(4-chloro-6-methyl-1,3,5-triazin-2-yl)-N-{[2-(trifluoromethyl)phenyl]methyl}-4-piperidinecarboxamide The title compound was prepared using the crude product obtained above from step a, and following the general procedure described in Example 70 step b, substituting the appropriate starting materials. MS (ES+): m/e 415.8 [M+H]⁺.

c) Preparation of 1-(4-amino-6-methyl-1,3,5-triazin-2-yl)-N-{[2-(trifluoromethyl)phenyl]methyl}-4-piperidinecarboxamide A solution of 2.0 M ammonia in methanol (6.78 ml, 13.6 mmol, 10.0 equiv) and DIEA (1.19 ml, 6.78 mmol, 5.00 equiv) was added dropwise to the previous reaction (step b). The reaction mixture was stirred at room temperature overnight in a capped scintillation vial. The reaction was concentrated under reduced pressure. The residue was dissolved in 1.5 ml DMSO and purified via reverse-phase HPLC purification to afford the title compound. MS (ES+): m/e 395.3 [M+H]⁺.

Example 72

1-[4-Ethyl-6-(4-methyl-1-piperazinyl)-1,3,5-triazin-2-yl]-N-{[2-(trifluoromethyl)phenyl]methyl}-4-piperidinecarboxamide

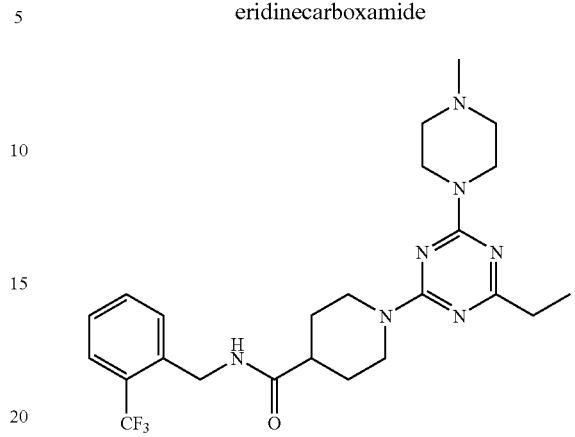

Example 72 was prepared using the general procedure described above in Example 71 substituting the appropriate starting materials. MS (ES+): m/e 492.0 [M+H]⁺.

Example 73

1-[4-Ethyl-6-(4-morpholinyl)-1,3,5-triazin-2-yl]-N-{[2-(trifluoromethyl)phenyl]methyl}-4-piperidinecarboxamide

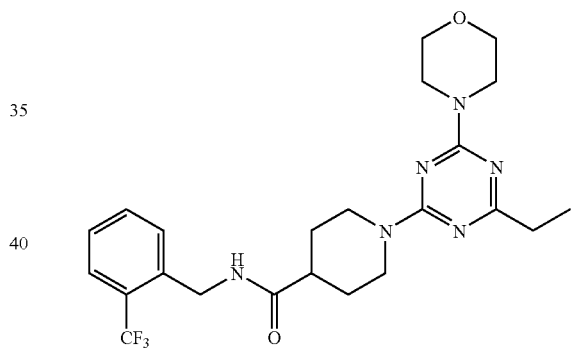

Example 73 was prepared using the general procedure described above in Example 71 substituting the appropriate starting materials. MS (ES+): m/e 479.4 [M+H]⁺.

Example 74

1-(4-Amino-6-ethyl-1,3,5-triazin-2-yl)-N-{[2-(trifluoromethyl)phenyl]methyl}-4-piperidinecarboxamide

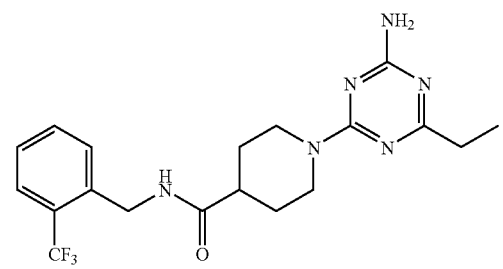

Example 74 was prepared using the general procedure described above in Example 71 substituting the appropriate starting materials. MS (ES+): m/e 409.5 [M+H]+.

Example 75

1-[4-Amino-6-(1-methylethyl)-1,3,5-triazin-2-yl]-N-{[2-(trifluoromethyl)phenyl]methyl}-4-piperidinecarboxamide

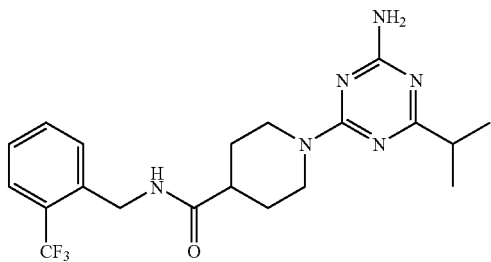

Example 75 was prepared using the general procedure described above in Example 71 substituting the appropriate starting materials. MS (ES+): m/e 423.5 [M+H]+.

Example 76

1-[4-Amino-6-(2-methylpropyl)-1,3,5-triazin-2-yl]-N-{[2-(trifluoromethyl)phenyl]methyl}-4-piperidinecarboxamide

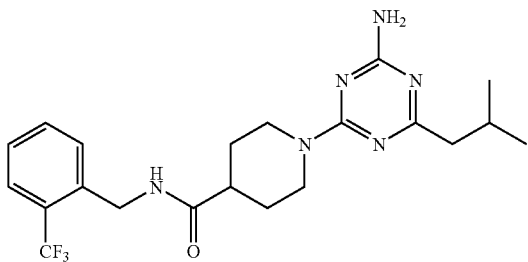

Example 76 was prepared using the general procedure described above in Example 71 substituting the appropriate starting materials. MS (ES+): m/e 437.5 [M+H]+.

Example 77

1-(4-Amino-6-phenyl-1,3,5-triazin-2-yl)-N-{[2-(trifluoromethyl)phenyl]methyl}-4-piperidinecarboxamide

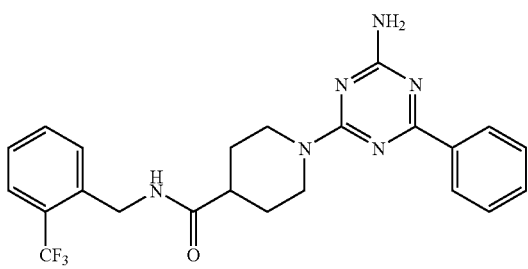

Example 77 was prepared using the general procedure described above in Example 71 substituting the appropriate starting materials. MS (ES+): m/e 457.5 [M+H]+.

Example 78

1-[4-Ethyl-6-(methylamino)-1,3,5-triazin-2-yl]-N-{[2-(trifluoromethyl)phenyl]methyl}-4-piperidinecarboxamide

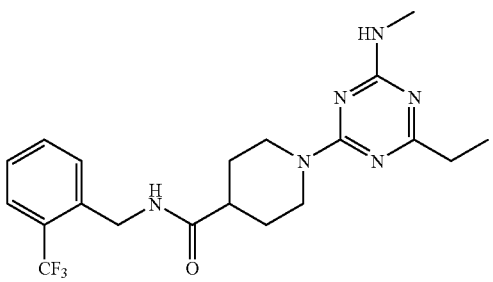

Example 78 was prepared using the general procedure described above in Example 71 substituting the appropriate starting materials. MS (ES+): m/e 422.8 [M+H]+.

Example 79

N-[(4-Chlorophenyl)methyl]-1-[4-(methylamino)-6-phenyl-1,3,5-triazin-2-yl]-4-piperidinecarboxamide

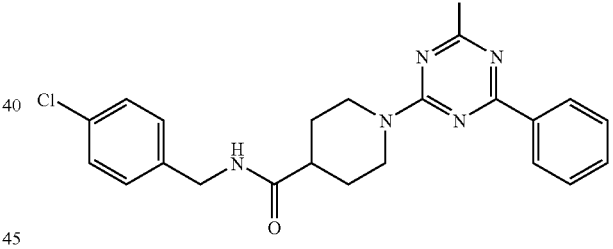

a) Preparation of 2,4-dichloro-6-phenyl-1,3,5-triazine

To a solution of cyanuric chloride (18.0 g, 97.6 mmol, 1.00 equiv) in THF was added phenylmagnesium bromide (97.6 ml of a 1.0 M solution in THF, 97.6 mmol, 1.00 equiv), dropwise, at 0° C. After the addition the mixture was stirred at room temperature for 1 h (monitored by TLC). The reaction mixture was poured onto ice and stirred at room temperature for 30 min. The product was extracted with ethyl acetate, and the combined organic extracts were washed with aqueous sodium chloride. The ethyl acetate extracts were then dried (over $Na_2SO_4$), and concentrated to afford 16 g of the title compound. The crude product was carried forward without purification.

b) Preparation of 4-chloro-N-methyl-6-phenyl-1,3,5-triazin-2-amine

A mixture of 2,4-dichloro-6-phenyl-1,3,5-triazine (16.0 g, 70.8 mmol, 1.00 equiv) dissolved in 1:1 $CH_3CN:H_2O$ (80 mL) was cooled (0° C.), and a solution of NH₂Me (8.00 g, 27.5% solution in H₂O, 70.8 mmol, 1.00 equiv) was added. The pH of the reaction mixture was adjusted to 9-10 by treating with 1 N NaOH. The pH was maintained at 9-10 for 15 min (product formation monitored by LCMS). The mixture was diluted with water, and filtered to provide 12 g of crude product (filtered solid was washed with additional water). A portion of this material (8 g) was purified by HPLC to afford 3.6 g of the title compound. MS (ES+): m/e 221.1 [M+H]$^+$.

c) Preparation of 1-[4-(methylamino)-6-phenyl-1,3,5-triazin-2-yl]-4-piperidinecarboxylic acid A mixture of 4-chloro-N-methyl-6-phenyl-1,3,5-triazin-2-amine (10.0 g, 45.3 mmol, 1.00 equiv) dissolved in 1:1 CH₃CN:H₂O (60 mL) was cooled (0° C.), and 4-piperidinecarboxylic acid (11.7 g, 90.6 mmol, 2.00 equiv) was added. The pH of the reaction mixture was adjusted to 9-10 by treating with 1 N NaOH. The pH was maintained at 9-10 for 24 hours (product formation monitored by LCMS). The mixture was diluted with water, and filtered to provide the crude product (filtered solid was washed with additional water). The resulting solid was purified by HPLC to afford 9.1 g of the title compound. MS (ES+): m/e 314.2 [M+H]$^+$.

d) Preparation of N-[(4-chlorophenyl)methyl]-1-[4-(methylamino)-6-phenyl-1,3,5-triazin-2-yl]-4-piperidinecarboxamide A mixture of 1-[4-(methylamino)-6-phenyl-1,3,5-triazin-2-yl]-4-piperidinecarboxylic acid (80.0 mg, 0.255 mmol), 4-chlorobenzylamine (32.0 mg, 0.255 mmol), EDCI (49.0 mg, 0.255 mmol), HOBt (35.0 mg, 0.255 mmol) and N-methylmorpholine (26.0 mg, 0.255 mmol) in CH₂Cl₂ (5 mL) was stirred for 20 h (reaction progress monitored by LCMS). The solvent was removed under vacuum, and the residue was purified by preparative HPLC to yield 75 mg of the title compound as a white solid. MS (ES+): m/e 437.1 [M+H]$^+$.

Example 80

1-[4-(Methylamino)-6-phenyl-1,3,5-triazin-2-yl]-N-[(2,4,6-trimethylphenyl)methyl]-4-piperidinecarboxamide

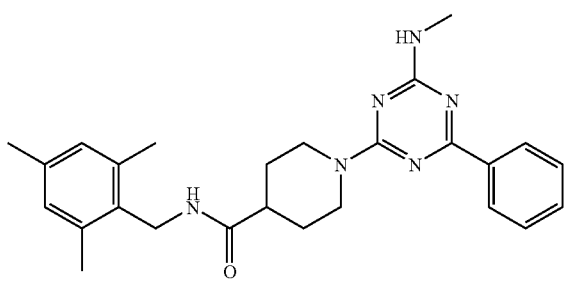

Example 80 was prepared using the general procedure described above in Example 79 substituting the appropriate starting materials. MS (ES+): m/e 445.3 [M+H]$^+$.

Example 81

N-[(2,4-Dichlorophenyl)methyl]-1-[4-(methylamino)-6-phenyl-1,3,5-triazin-2-yl]-3-piperidinecarboxamide

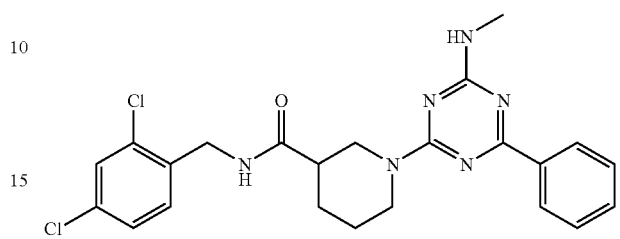

Example 81 was prepared using the general procedure described above in Example 79 substituting the appropriate starting materials. MS (ES+): m/e 471.2 [M+H]$^+$.

Example 82

1-[4-(Methylamino)-6-phenyl-1,3,5-triazin-2-yl]-N-{[2-(trifluoromethyl)phenyl]methyl}-3-piperidinecarboxamide

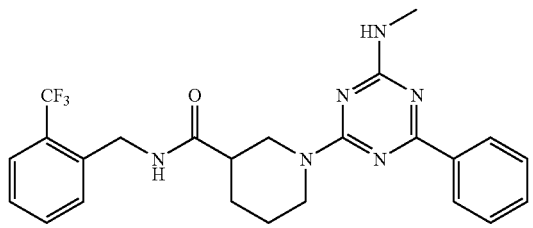

Example 82 was prepared using the general procedure described above in Example 79 substituting the appropriate starting materials. MS (ES+): m/e 471.2 [M+H]$^+$.

Example 83

1-[4-(Methylamino)-6-phenyl-1,3,5-triazin-2-yl]-N-{[2-(trifluoromethyl)phenyl]methyl}-4-piperidinecarboxamide

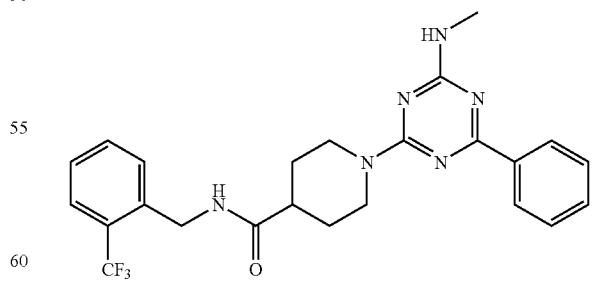

a) Preparation of ethyl 1-(4,6-dichloro-1,3,5-triazin-2-yl)-4-piperidinecarboxylate To a suspension of 2,4,6-trichloro-1,3,5-triazine (5.0 g, 27 mmol, 1.0 equiv) in dichloromethane (50 ml) at −50° C., a premixed solution of ethyl 4-piperidinecarboxylate (4.1 ml, 27 mmol, 1.0 equiv) and diisopropylethylamine (DIEA, 14.2 ml, 81.3 mmol, 3.00 equiv) in dichloromethane (100 ml) was added dropwise via an addition funnel. The reaction mixture was allowed to warm to room temperature, and stirring was continued overnight. The solvent was removed under reduced pressure to yield 7.95 g (96%) of the title compound. MS (ES+): m/e 305.3 [M+H]$^+$.

b) Preparation of ethyl 1-[4-chloro-6-(methylamino)-1,3,5-triazin-2-yl]-4-piperidinecarboxylate To a solution of ethyl 1-(4,6-dichloro-1,3,5-triazin-2-yl)-4-piperidinecarboxylate (1.0 g, 3.3 mmol, 1.0 equiv) in dichloromethane (20 ml) at room temperature, a premixed solution of methylamine (1.6 ml, 3.3 mmol, 1.0 equiv) and diisopropylethylamine (DIEA, 1.7 ml, 9.8 mmol, 3.0 equiv) in dichloromethane (10 ml) was added dropwise. The reaction was stirred for 3 h at room temperature. The solvent was removed under reduced pressure to afford 983 mg (100%) of the title compound. MS (ES+): m/e 300.1 [M+H]$^+$.

c) Preparation of 1-[4-chloro-6-(methylamino)-1,3,5-triazin-2-yl]-4-piperidinecarboxylic acid To a solution of ethyl 1-[4-chloro-6-(methylamino)-1,3,5-triazin-2-yl]-4-piperidinecarboxylate (983 mg, 3.28 mmol, 1.00 equiv) in tetrahydrofuran (21 ml) at 0° C., a premixed solution of lithium hydroxide monohydrate (275 mg, 6.56 mmol, 2.00 equiv) and water (7 ml) was added dropwise. Methanol (7 ml) was added. The reaction was allowed to warm to room temperature over 1 h and stirring was continued for 3 h. The solvent was removed under reduced pressure, yielding a colorless oil. Ethyl acetate was added to the oil, and the desired product precipitated as a white solid. The solid was filtered and dried under reduced pressure to provide 885 mg (99%) of the title compound. MS (ES+): m/e 272.0 [M+H]$^+$.

d) Preparation of 1-[4-chloro-6-(methylamino)-1,3,5-triazin-2-yl]-N-{[2-(trifluoromethyl)phenyl]methyl}-4-piperidinecarboxamide To a suspension of 1-[4-chloro-6-(methylamino)-1,3,5-triazin-2-yl]-4-piperidinecarboxylic acid (885 mg, 3.25 mmol, 1.00 equiv) in DMF (32 ml) at room temperature, {[2-(trifluoromethyl)phenyl]methyl}amine (456 μL, 3.25 mmol, 1.00 equiv), EDCI (748 mg, 3.90 mmol, 1.20 equiv), HOBT (527 mg, 3.90 mmol, 1.00 equiv), and diisopropylethylamine (DIEA, 2.80 ml, 16.3 mmol, 5.00 equiv) were added. Stirring was continued overnight at room temperature. The reaction mixture was partitioned between 1:1 water and ethyl acetate (200 ml). The product was extracted three times with ethyl acetate (50 ml). The ethyl acetate extracts were combined and washed successively with saturated ammonium chloride (100 ml), water (100 ml), and saturated sodium chloride (100 ml). The ethyl acetate solution was dried with Na$_2$SO$_4$, filtered, and concentrated under reduced pressure to yield 1.23 g (88%) of the title compound. MS ES+): m/e 428.7 [M+H]$^+$.

e) Preparation of 1-[4-(methylamino)-6-phenyl-1,3,5-triazin-2-yl]-N-{[2-(trifluoromethyl)phenyl]methyl}-4-piperidinecarboxamide A 5 ml microwave vial was charged with palladium (II) acetate (0.38 mg, 0.0017 mmol, 0.010 equiv), tricyclohexylphosphine (0.95 mg, 0.0034 mmol, 0.020 equiv), and phenyl boronic acid (30.9 mg, 0.253 mmol, 1.50 equiv). A premixed solution of 1,4-dioxane (0.875 ml) and 1-[4-chloro-6-(methylamino)-1,3,5-triazin-2-yl]-N-{[2-(trifluoromethyl)phenyl]methyl}-4-piperidinecarboxamide was added, followed by a premixed solution of water (0.125 ml) and potassium phosphate tribasic (71.7 mg, 0.338 mmol, 2.00 equiv). The reaction was heated via a microwave reactor for 20 min at 150° C. The reaction was diluted with water (5 ml) and extracted three times with ethyl acetate (5 ml). The ethyl acetate extracts were combined, dried with Na$_2$SO$_4$, filtered, and concentrated under reduced pressure. The residue was dissolved in 1.5 ml DMSO and purified via reverse-phase HPLC purification to afford the title compound. MS (ES+): m/e 470.9 [M+H]$^+$.

Example 84

1-[4-(Methylamino)-6-(3-thienyl)-1,3,5-triazin-2-yl]-N-{[2-(trifluoromethyl)phenyl]methyl}-4-piperidinecarboxamide

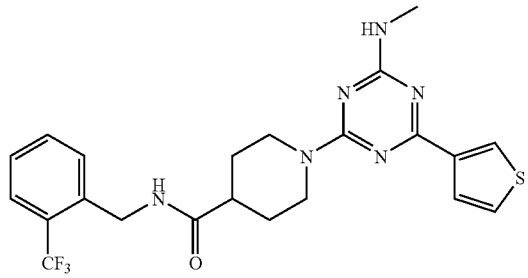

Example 84 was prepared using the general procedure described above in Example 83 substituting the appropriate starting materials. MS (ES+): m/e 476.8 [M+H]$^+$.

Example 85

1-[4-[4-(1,1-Dimethylethyl)phenyl]-6-(methylamino)-1,3,5-triazin-2-yl]-N-{[2-(trifluoromethyl)phenyl]methyl}-4-piperidinecarboxamide

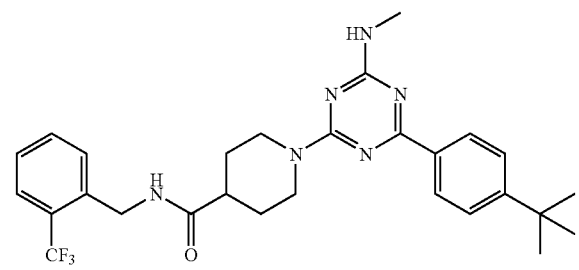

Example 85 was prepared using the general procedure described above in Example 83 substituting the appropriate starting materials. MS (ES+): m/e 527.1 [M+H]$^+$.

Example 86
N-{[4-cyano-2-(trifluoromethyl)phenyl]methyl}-1-[4-methyl-6-(methylamino)-1,3,5-triazin-2-yl]-4-piperidinecarboxamide

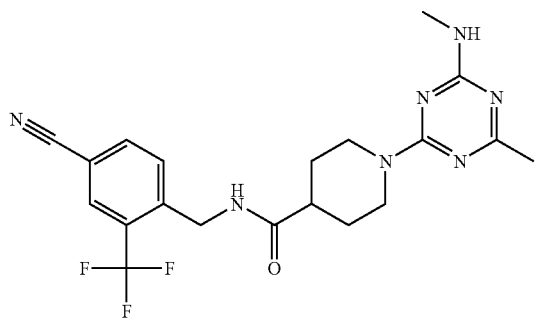

1-[4-methyl-6-(methylamino)-1,3,5-triazin-2-yl]-4-piperidinecarboxylic acid (163 mg, 0.65 mmol) was dissolved in 10 mL of dichloromethane and treated with EDCI (150 mg, 0.72 mmol), HOBt (88 mg, 0.65 mmol), N-methylmorpholine (0.2 mL, 1.5 mmol), and 4-(aminomethyl)-3-(trifluoromethyl)benzonitrile (130 mg, 0.65 mmol) at room temperature for 12 hours. The reaction mixture was concentrated and purified by preparative HPLC to provide N-{[4-cyano-2-(trifluoromethyl)phenyl]methyl}-1-[4-methyl-6-(methylamino)-1,3,5-triazin-2-yl]-4-piperidinecarboxamide (7 mg, 0.02 mmol, 2%) as a white solid. MS (ES+): m/e 434 [M+H]$^+$.

Example 87
1-[4-methyl-6-(methylamino)-1,3,5-triazin-2-yl]-N-({2-[(trifluoromethyl)thio]phenyl}methyl)-4-piperidinecarboxamide

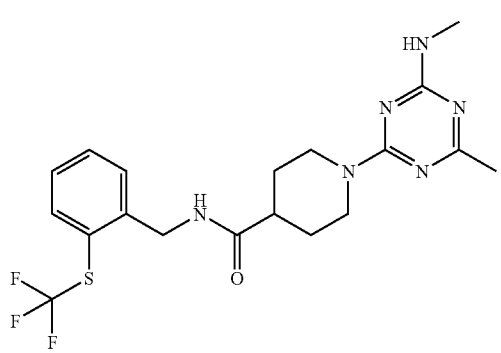

Example 87 was prepared using the general procedure described above in Example 86 substituting 1-{2-[(trifluoromethyl)thio]phenyl}methanamine for 4-(aminomethyl)-3-(trifluoromethyl)benzonitrile. MS (ES+): m/e 441 [M+H]$^+$.

Example 88
1-[4-methyl-6-(methylamino)-1,3,5-triazin-2-yl]-N-({2-[(trifluoromethyl)thio]phenyl}methyl)-4-piperidinecarboxamide

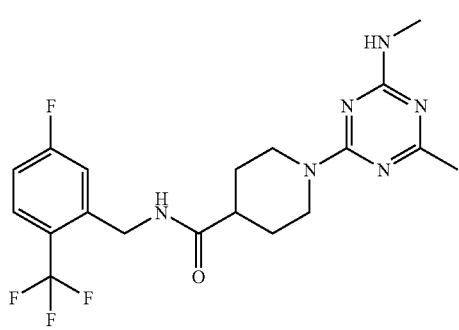

Example 88 was prepared using the general procedure described above in Example 86 substituting 1-[5-fluoro-2-(trifluoromethyl)phenyl]methanamine for 4-(aminomethyl)-3-(trifluoromethyl)benzonitrile. MS (ES+): m/e 427 [M+H]$^+$.

Example 89
1-[4-methyl-6-(methylamino)-1,3,5-triazin-2-yl]-N-{[4-(methyloxy)-2-(trifluoromethyl)phenyl]methyl}-4-piperidinecarboxamide

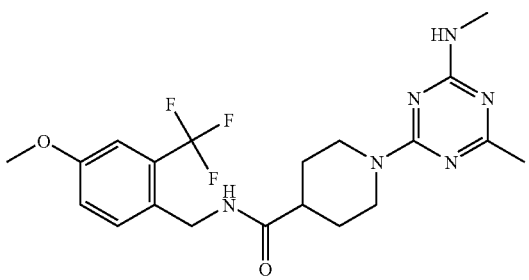

Example 89 was prepared using the general procedure described above in Example 86 substituting 1-[4-(methyloxy)-2-(trifluoromethyl)phenyl]methanamine for 4-(aminomethyl)-3-(trifluoromethyl)benzonitrile. MS (ES+): m/e 439 [M+H]$^+$. $^1$H NMR (400 MHz, DMSO-D6) ⊏ 7.4 (d, 1H), 7.2 (s, 1H), 7.1 (d, 1H), 4.9 (m, 2H), 4.5 (m, 2H), 3.8 (s, 3H), 3.1 (m, 2H), 3.0 (s, 3H), 2.6 (s, 1H), 2.4 (s, 3H), 1.9 (m, 2H), 1.7 (m, 2H)

Example 90
N-[(2,4-dichlorophenyl)methyl]-1-{4-[(2-hydroxyethyl)amino]-6-methyl-1,3,5-triazin-2-yl}-4-piperidinecarboxamide

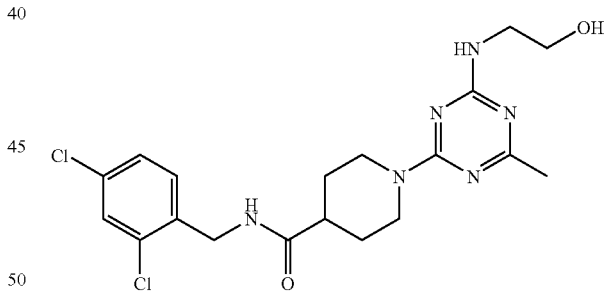

Step 1: 1,1-dimethylethyl-4-({[(2,4-dichlorophenyl)methyl]amino}carbonyl)-1-piperidinecarboxylate

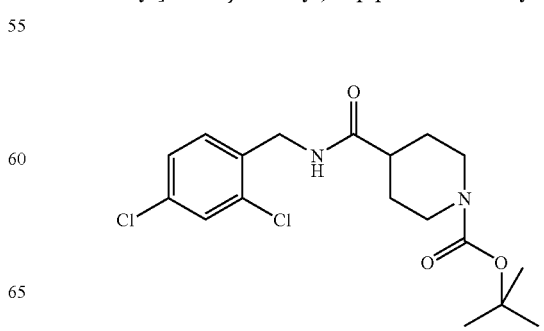

A 1000 mL round-bottom flask charged with argon was equipped with a magnetic stir bar, prior to the addition of 1-{[(1,1-dimethylethyl)oxy]carbonyl}-4-piperidinecarboxylic acid (16.32 g, 71.2 mmol), 2,4-dichlorobenzylamine (9.5 mL, 71.2 mmol) and 100 mL of DMF at room temperature. Afterwards, triethylamine (29.8 mL, 213.5 mmol) was added and the solution was allowed to stir for several minutes before a separate solution of 1H-1,2,3-benzotriazol-1-yloxytris(dimethylamino)-phosphonium hexafluorophosphate (BOP reagent, 31.5 g, 71.2 mmol) dissolved in 78 mL of DMF was delivered to the mixture at room temperature. The reaction was maintained at that temperature for 48 hours, before it was determined to be complete by LCMS (Rt=8.6 min and m/e 388 [M+1]$^+$). Pouring the crude mixture into a vigorously stirring 50/50 solution of saturated sodium bicarbonate and water (1.5 L), resulted in the precipitation of the desired product as an off-white solid. The solid was recovered by vacuum filtration and dried for 24 hours under vacuum to give 27.2 g of 1,1-dimethylethyl-4-({[(2,4-dichlorophenyl)methyl]amino}carbonyl)-1-piperidinecarboxylate (70.2 mmol, 98.6%). MS (ES) m/e 388 [M+H]$^+$. $^1$H NMR (400 MHz, DMSO-D6) ☐ 8.4 (m, 1H), 7.6 (d, 1H), 7.3 (d, 1H), 4.3 (m, 2H), 4.0 (m, 2H), 2.7 (m, 2H), 2.3 (m, 1H), 1.7 (m, 2H), 1.5 (m, 2H), 1.4 (s, 9H)

Step 2: N-[(2,4-dichlorophenyl)methyl]-4-piperidinecarboxamide

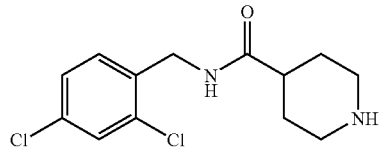

A 500 mL round bottom flask equipped with a magnetic stir bar was charged with 1,1-dimethylethyl-4-({[(2,4-dichlorophenyl)methyl]amino}carbonyl)-1-piperidinecarboxylate (27.6 g, 71.2 mmol) and DCM (117 mL) at room temperature. Trifluoroacetic acid (117 mL) was added slowly, and the reaction was maintained at room temperature for 1 hour after which time LC/MS determined that the reaction was complete (Rt=6.03 min and m/e 287 [M+1]$^+$). The volatiles were removed by rotary evaporation and the crude oil was dissolved in ethyl acetate and washed with saturated sodium bicarbonate solution (3×200 mL). The organic phase was dried over Na$_2$SO$_4$, filtered and concentrated to give 13.5 g of N-[(2,4-dichlorophenyl)methyl]-4-piperidinecarboxamide (47 mmol, 66%) as a pale yellow solid. MS (ES) m/e 287 [M+H]$^+$. $^1$H NMR (400 MHz, DMSO-D6) ☐ 8.6 (m, 1H), 7.4 (d, 1H), 7.3 (d, 1H), 4.3 (m, 2H), 3.2 (m, 2H), 2.8 (m, 2H), 2.5 (m, 1H shouldering on DMSO peak), 1.8 (m, 2H), 1.7 (m, 2H)

Step 3: 1-(4-chloro-6-methyl-1,3,5-triazin-2-yl)-N-[(2,4-dichlorophenyl)methyl]-4-piperidinecarboxamide

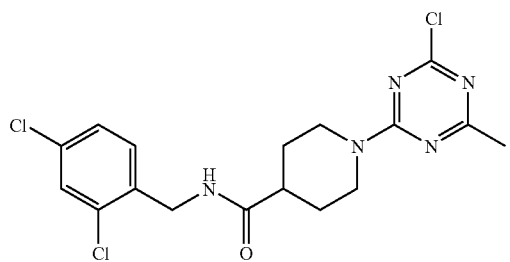

To a 25 mL round-bottomed flask was added 2,4-dichloro-6-methyl-1,3,5-triazine (800 mg, 2.79 mmol) and N-[(2,4-dichlorophenyl)methyl]-4-piperidinecarboxamide (859 mg, 2.79 mmol) in acetonitrile (8.7 mL). Diisopropylethylamine (1.46 mL, 8.36 mmol) was added to give a yellow suspension. The reaction mixture was stirred at room temperature for 15 minutes, at which time LC-MS showed the reaction was complete. This suspension was filtered through a Buchner funnel to afford 1-(4-chloro-6-methyl-1,3,5-triazin-2-yl)-N-[(2,4-dichlorophenyl)methyl]-4-piperidinecarboxamide (596 mg, 1.44 mmol, 52%) as a white solid which was used in the next step without further purification. MS (ES) m/e 416 [M+H]$^+$.

Step 4: N-[(2,4-dichlorophenyl)methyl]-1-{4-[(2-hydroxyethyl)amino]-6-methyl-1,3,5-triazin-2-yl}-4-piperidinecarboxamide

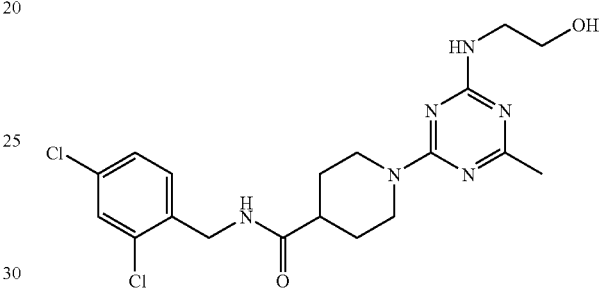

To a 10 mL reaction vial was added the 1-(4-chloro-6-methyl-1,3,5-triazin-2-yl)-N-[(2,4-dichlorophenyl)methyl]-4-piperidinecarboxamide (50 mg, 0.121 mmol) and acetonitrile (0.754 mL) to give a white suspension. Then, [2-(methyloxy)ethyl]amine (0.105 mL, 1.206 mmol) and DIEA (0.063 mL, 0.362 mmol) were added. The reaction was heated for 1 h at 80° C. The reaction mixture was diluted with DMSO and purified by preparative HPLC to provide N-[(2,4-dichlorophenyl)methyl]-1-{4-[(2-hydroxyethyl)amino]-6-methyl-1,3,5-triazin-2-yl}-4-piperidinecarboxamide (46 mg, 0.078 mmol, 65%) as a white solid. MS (ES) m/e 439, 441 [M+H]$^+$. $^1$H NMR (400 MHz, DMSO-D6) 8.5 (bs, 1H), ☐ 8.3 (bs, 1H), 7.7 (s, 1H), 7.4 (m, 1H), 7.3 (m, 1H), 4.7 (m, 2H), 4.3 (m, 2H), 3.8-3.3 (3H under H$_2$O peak), 3.1 (m, 4H), 2.6 (m, 1H), 2.3 (s, 3H), 1.8 (m, 2H), 1.5 (m, 2H)

In an alternative preparation of N-[(2,4-dichlorophenyl)methyl]-1-{4-[(2-hydroxyethyl)amino]-6-methyl-1,3,5-triazin-2-yl}-4-piperidinecarboxamide, this compound was prepared on a larger scale: To a 250 mL round bottom flask was added 2,4-dichloro-6-methyl-1,3,5-triazine (1.5 g, 9.15 mmol), acetonitrile (91 ml), N-[(2,4-dichlorophenyl)methyl]-4-piperidinecarboxamide (2.63 g, 9.15 mmol), and diisopropylethylamine (1.598 ml, 9.15 mmol). The mixture was stirred for 30 min, at which time LC-MS showed that the reaction was complete. Next, 2-aminoethanol (0.559 g, 9.15 mmol) was added, and the reaction mixture was heated to 40° C. overnight. The product was collected by Buchner filtration to afford 4.99 g of a white solid. 1 g of the crude product was purified by preparative HPLC to afford 670 mgs of N-[(2,4-dichlorophenyl)methyl]-1-{4-[(2-hydroxyethyl)amino]-6-methyl-1,3,5-triazin-2-yl}-4-piperidinecarboxamide as the TFA salt. This material was converted to the HCl salt by repeated addition and concentration of 2 M HCl in ether. In the final cycle, the HCl salt was collected by filtration. The HCl salt was recrystallized from ethanol to provide N-[(2,4-dichlorophenyl)methyl]-1-{4-[(2-hydroxyethyl)amino]-6-methyl-1,3,5-triazin-2-yl}-4-piperidinecarboxamide, HCl salt (229 mg, 0.46 mmol) as a crystalline solid. MS (ES) m/e 439, 441 [M+H]+. 1H NMR (400 MHz, DMSO-D6) ☐ 8.5 (bs, 1H), 8.2 (bs, 1H), 7.6 (s, 1H), 7.4 (m, 1H), 7.3 (m, 1H), 4.7 (m, 2H), 4.3 (m, 2H), 3.5 (m, 2H), 3.4 (m, 2H), 3.1 (m, 2H), 2.6 (m, 1H), 2.4 (m, 1H), 2.3 (s, 3H), 1.8 (m, 2H), 1.5 (m, 2H)

Example 91

N-({4-bromo-2-[(trifluoromethyl)oxy]phenyl}methyl)-1-[4-methyl-6-(methylamino)-1,3,5-triazin-2-yl]-4-piperidinecarboxamide

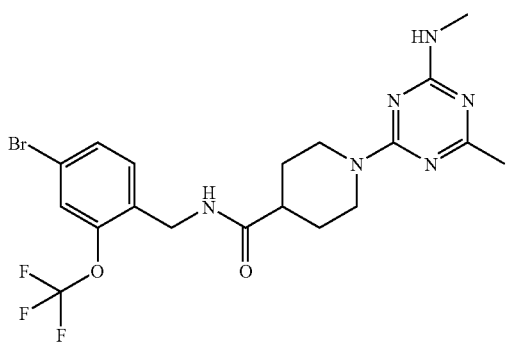

1-[4-methyl-6-(methylamino)-1,3,5-triazin-2-yl]-4-piperidinecarboxylic acid (100 mg, 0.4 mmol) was dissolved in 3 mL of dichloromethane and treated with EDCI (115 mg, 0.6 mmol), HOBt (65 mg, 0.48 mmol), triethylamine (0.44 mL, 3.2 mmol), and 1-{4-bromo-2-[(trifluoromethyl)oxy]phenyl}methanamine (152 mg, 0.4 mmol) at 8° C. for 4 days. The reaction mixture was concentrated and purified by preparative HPLC to provide N-{[4-cyano-2-(trifluoromethyl)phenyl]methyl}-1-[4-methyl-6-(methylamino)-1,3,5-triazin-2-yl]-4-piperidinecarboxamide (3.5 mg, 0.02 mmol, 2%) as a white solid. MS (ES+): m/e 503, 505 [M+H]+. 1H NMR (400 MHz, methanol-D4) ∟ 7.4 (m, 2H), 7.2 (d, 1H), 4.8 (2H under MeOH peak), 4.3 (s, 2H), 3.1 (m, 2H), 2.9 (s, 3H), 2.5 (m, 1H), 2.3 (s, 3H), 1.8 (m, 2H), 1.6 (m, 2H)

Example 92

N-{[4-fluoro-2-(trifluoromethyl)phenyl]methyl}-1-[4-methyl-6-(methylamino)-1,3,5-triazin-2-yl]-4-piperidinecarboxamide

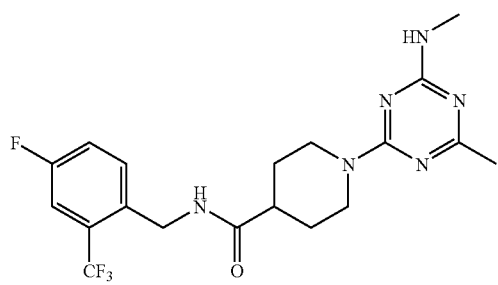

Example 92 was prepared using the general procedure described above in Example 86 substituting 1-[4-fluoro-2-(trifluoromethyl)phenyl]methanamine for 4-(aminomethyl)-3-(trifluoromethyl)benzonitrile. MS (ES+): m/e 427 [M+H]+.

As used above, the phrase "using the general procedure described above" indicates that the procedure used employs similar, but not necessarily identical, reaction conditions to those referred to.

Biological Activity

The compounds according to Formula I are sEH inhibitors. The compounds according to Formula I, therefore, are useful in the treatment of hypertension and other conditions involving sEH activity. As stated above, mEH provides an important detoxification pathway in mammals. Compounds that exhibit pharmacological selectivity for sEH over mEH therefore are desirable in the methods of treatment described below. Accordingly, in one embodiment the invention is directed to a compound according to Formula I wherein the compound exhibits a selectivity ratio equal to or greater than 10:1 for sEH over mEH. In another embodiment the invention is directed to a compound according to Formula I wherein the compound exhibits a selectivity ratio equal to or greater than 100:1 for sEH over mEH. In another embodiment the invention is directed to a compound according to Formula I wherein the compound exhibits a selectivity ratio equal to or greater than 1000:1 for sEH over mEH.

The biological activity of the compounds according to Formula I can be determined using any suitable assay for determining the activity of a candidate compound as an sEH and/or mEH inhibitor, as well as suitable tissue and/or in vivo models.

In Vitro Fluorescence Assay

Inhibition of Soluble Epoxide Hydrolase (sEH) activity is measured in a fluorescent assay based upon the format described by Wolf et al. (Analytical Biochemistry Vol. 355 (2006) pp. 71-80). In the presence of sEH, PHOME ((3-Phenyl-oxiranyl)-acetic acid cyano-(6-methoxy-naphthalen-2-yl)-methyl ester), is hydrolyzed to a diol which goes through an intramolecular cyclization and the release and decomposition of cyanohydrin (products=cyanide and 6-methoxy-2-naphthaldehyde). Production of 6-methoxy-2-naphthaldehyde is monitored at excitation of 360 nm and an emission of 465 nm.

The assay is used in a quenched assay format by sequentially adding enzyme (5 uL; 200 µM sEH in 25 mM Hepes at pH 7.0, 0.01% CHAPS (w/v), 0.005% Casein (w/v); 10 minute ambient pre-incubation after addition) then PHOME substrate (5 ul; 10 uM PHOME substrate in 25 mM Hepes at pH 7.0, 0.01% CHAPS (w/v), 0.005% Casein (w/v)) to a 384 well assay plate (Greiner 784076) pre-stamped with 25-100 mL compound at the desired concentration. The reaction is incubated for 30 minutes at room temperature, then quenched by the addition of stop solution (5 uL; 10 mM ZnSO4 in 25 mM Hepes at pH 7.0, 0.01% CHAPS (w/v), 0.005% Casein (w/v)). Microtiter plates are centrifuged after each addition for 30 seconds at 500 rpm. The fluorescence is measured on an EnVision plate reader platform (Perkin Elmer) using a 360 nm excitation filter, 465 nm emission filter, and 400 nm dichroic filter.

Compounds are first prepared in neat DMSO at a concentration of 10 mM, then diluted as required to achieve the desired assay concentration. For inhibition curves, compounds are diluted using a three fold serial dilution and tested at 11 concentrations (e.g. 50 µM-0.8 nM or 25 µM-0.42 nM or 2.5 µM to 42 pM). Curves are analysed using ActivityBase and XLfit, and results are expressed as $pIC_{50}$ values.

Cell-Based sEH Inhibitor Assay

Cell based sEH inhibition is measured using the 14,15-DHET immunoassay ELISA kit available from Detroit R&D (Cat. No. DH1), according to the following procedure:

HEK293 cells (BioCat ID 80556) are transduced by sEH BacMam virus to increase sEH expression (other cell lines may be suitable) as follows: One day before the experiment, 1.5 million HEK293 cells (BioCat ID 80556) are seated in 3 ml of DMEM/F12 (with L-Glutamine, with 15 mM HEPES, pH7.30, from Media Prep Lab), with 10% fetal bovine serum (from SAFC Biosciences, Cat. No. 12176-1000M), no antibiotic, in a 25 cm$^2$ flask (from Corning Incorporated, Cat. No. 430639) and 30 µL sEH BacMam virus is added. The cells are gently mixed then incubated at 37° C., 5% $CO_2$, for 24 hours.

The cells are trypsinized to release them from the growth flask, washed once with PBS, then re-suspended in 5 mL DMEM/F12 without phenol red (from Media Prep lab). Cell density should be approximately 3*10$^5$ cells/mL (=300 cells/µL), counted using the Cedex AS[20] (from Innovatis).

The cells are then diluted in DMEM/F12 to 5.1 cells/µL, and 98 µL/well (=500 cells/well) of this cell suspension is transferred to an assay plate (96 well, clear polystyrene, flat bottom, from Whatman, Cat. No. 7701-1350). 2 µL of the diluted test compound is then added to the cells in the assay plate. The reaction plate is shaken gently and incubated at room temperature for 30 min, after which 10 µL of substrate solution is added (substrate solution is prepared by diluting 1.24 µL of 14,15-EET from Cayman Chemical, Cat. No. 50651 with 8.24 µL DMEM/F12). The assay plate is then incubated for one hour at room temperature.

After the 1 hour reaction, the reaction mixture is diluted 3 fold with provided sample dilution buffer (ex. Add 220 µL to the 110 µL reaction mixture), mixed well, and spun for 5 min at 500 rpm.

100 µL of the diluted reaction mixture is then transferred from the reaction plates to the ELISA plates, and the ELISA is performed according to the instructions provided in the kit.

IC50s and pIC50s are then calculated. The IC50 can be calculated directly using the 14,15-DHET concentration or using the % inhibition [% inhibition=100*(1−(sample DHET−0 cell DHET)/(500 cells DHET−0 cell DHET)].

Compounds are first prepared in neat DMSO at a concentration of 0.5 mM, then diluted as required to achieve the desired assay concentration. For inhibition curves, compounds are diluted using a three fold serial dilution and tested at 9 concentrations (e.g. 10 µM-1.5 nM). Curves are analysed using ActivityBase and XLfit, and results are expressed as pIC50 values.

Biological Activity Results

All of the compounds exemplified above were tested for activity as sEH inhibitors. Where the assay for a particular compound had been performed two or more times, the following conclusion regarding their activities is based on the average of individual experiments: All exemplified compounds were found to have an IC50 in the range of 0.1 and 10,000 nM.

Methods of Use

The compounds of the invention inhibit the sEH enzyme and can be useful in the treatment of conditions wherein the underlying pathology is (at least in part) attributable to sEH involvement or in conditions wherein sEH inhibition offers some clinical benefit even though the underlying pathology is not (even in part) attributable to sEH involvement. Examples of such conditions include hypertension, organ failure/damage (including heart failure, renal failure, and liver failure), cardiac and renal fibrosis, peripheral vascular disease (including ischemic limb disease, intermittent claudication, endothelial dysfunction, erectile dysfunction, Raynaud's disease, and diabetic vasculopathies e.g. retinopathy), atherothrombotic disorders (including coronary artery disease, coronary vasospasm, angina, stroke, myocardial ischemia, myocardial infarction, and hyperlipidemia), metabolic disorders (including diabetes), and inflammatory disorders (including arthritis, inflammatory pain, overactive bladder, asthma, and COPD). Accordingly, in another aspect the invention is directed to methods of treating such conditions.

Essential hypertension is commonly associated with the development of significant end organ damage such as renal, endothelial, myocardial, and erectile dysfunction. Such conditions occur "secondary" to the elevated systemic arterial blood pressure. Secondary conditions may be prevented by treatment of the underlying ("primary") cause. Accordingly, in another aspect the invention is directed to methods of preventing such secondary conditions.

Heart failure is a complex heterogenous disorder characterized by reduced cardiac output, resulting in the inability of the heart to meet perfusion demands of the body. Cardiac proinflammatory cytokine recruitment and maladaptive cardiac hypertrophy, fibrosis and apoptosis/necrosis are factors associated with the progression of heart failure. Compounds of the invention are directed to methods of treating such conditions.

In addition, sEH is indirectly involved in the regulation of platelet function through its effect on EETs. Drugs that inhibit platelet aggregation are believed to decrease the risk of atherothrombotic events, such as myocardial infarction and stroke, in patients with established cardiovascular atherosclerotic disease. Accordingly, in another aspect the invention is directed to methods of preventing atherothrombotic events, such as myocardial infarction and stroke in patients with a history of recent myocardial infarction, stroke, transient ischemic attacks, unstable angina, or atherosclerosis.

The methods of treating and the methods of preventing described above comprise administering a safe and effective amount of a compound of the invention to a patient in need thereof.

As used herein, "treatment" in reference to a condition means: (1) the amelioration or prevention of the condition being treated or one or more of the biological manifestations of the condition being treated, (2) the interference with (a) one or more points in the biological cascade that leads to or is responsible for the condition being treated or (b) one or more of the biological manifestations of the condition being treated, or (3) the alleviation of one or more of the symptoms or effects associated with the condition being treated.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to significantly induce a positive modification in the condition to be treated but low enough to avoid serious side effects (at a reasonable benefit/risk ratio) within the scope of sound medical judgment. A safe and effective amount of a compound of the invention will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient being treated; the duration of the treatment; the nature of concurrent therapy; the desired therapeutic effect; and like factors, but can nevertheless be determined by the skilled artisan.

As used herein, "patient" refers to a human or other animal.

Compositions

The compounds of the invention will normally, but not necessarily, be formulated into a pharmaceutical composition prior to administration to a patient. Accordingly, in another aspect the invention is directed to pharmaceutical compositions comprising a compound of the invention and a pharmaceutically-acceptable excipient.

The pharmaceutical compositions of the invention may be prepared and packaged in bulk form wherein a safe and effective amount of a compound of the invention can be extracted and then given to the patient such as with powders, syrups, and solutions for injection. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds. Conversely, the pharmaceutical compositions of the invention typically contain more than one pharmaceutically-acceptable excipient. However, in certain embodiments, the pharmaceutical compositions of the invention contain one pharmaceutically-acceptable excipient.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excepients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the amount administered and the duration such regimens are administered, for a compound of the invention depend on the condition being treated, the severity of the condition being treated, the age and physical condition of the patient being treated, the medical history of the patient to be treated, the nature of concurrent therapy, the particular route of administration chosen, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Typical daily dosages range from 1 mg to 1000 mg.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

What is claimed is:
1. A compound according to Formula I:

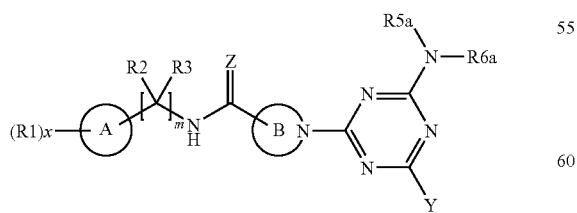

Formula I wherein:
A is phenyl, monocyclic heteroaryl, or C5-C6 cycloalkyl;
when A is phenyl or monocyclic heteroaryl each R1 is independently selected from the group consisting of:
halo, CN, Ra, ORb, C(O)ORc, C(O)NRcRc, NRcRc, NRcC(O)Rb, NRcS(O$_2$)Ra, SRb, S(O$_2$)Ra, and S(O$_2$)NRcRc;
when A is C5-C6 cycloalkyl each R1 is independently selected from the group consisting of: Ra, ORb, C(O)ORc, C(O)NRcRc, NRcRc, and NRcC(O)Rb;
x is an integer from 0 to 5;
R2 is H;
R3 is H;
m is 1 or 2;
Z is O or S;
B is B1, B2, B3, B4, or B5;
B1 is

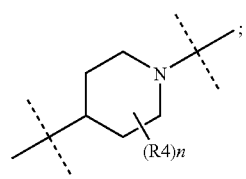

B2 is

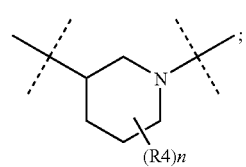

B3 is

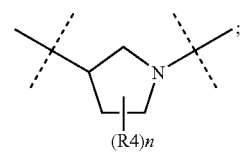

B4 is

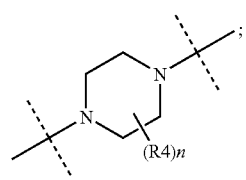

B5 is

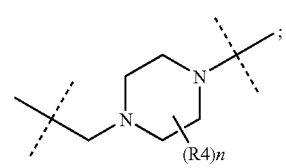

each R4 is independently C1-C3 alkyl;
n is an integer from 0 to 4;
Y is H, OH, R7, R8, R9, R10, R11, R12, or NR5bR6b;

R5a and R5b are each independently H, R51, R52, R53, R54, R55, —C(O)Rb, —C(O)NRcRc, —S(O₂)Ra, or —S(O₂)NRcRc;

each R51 is C1-C6 alkyl optionally substituted with one or more substituents selected from the group consisting of: halo, ORd, SRk, C(O)ORc, C(O)NReRe, NReRe, Rg, Rh, Ri, Rj;

each R52 is C3-C6 cycloalkyl optionally substituted with one or more substituents selected from the group consisting of: halo, ORd, SRd, C(O)ORc, C(O)NReRe, NReRe, C1-C3 alkyl, and C1-C3 haloalkyl;

R53 is monocyclic heterocycloalkyl optionally substituted with one or more C1-C3 alkyl;

R54 is phenyl optionally substituted with one or more substituents selected from the group consisting of: halo, CN, Ra, ORb, C(O)ORc, C(O)NRcRc, NRcRc, NRcC(O)Rb, NRcS(O₂)Ra, SRb, S(O₂)Ra, and S(O₂)NReRe;

R55 is monocyclic heteroaryl optionally substituted with one or more substituents selected from the group consisting of: halo, —CN, C1-C3 alkyl, C1-C3 haloalkyl, ORd, and NReRe;

R6a and R6b are each independently H, R51, or R52; or

R5a and R6a and/or R5b and R6b, independently in each instance, taken together with the nitrogen atom to which they are attached form a saturated monocyclic ring having from 5 to 7 member atoms wherein said ring optionally contains one additional heteroatom as a member atom and wherein said ring is optionally substituted with one or more substituents selected from the group consisting of: C1-C3 alkyl, ORd, and NRfRf;

R7 is C1-C8 alkyl optionally substituted with one or more substituents selected from the group consisting of: halo, ORd, SRd, NReRe, C3-C6 cycloalkyl, Ri, and Rj;

R8 is C3-C6 cycloalkyl optionally substituted with one or more substituents selected from the group consisting of: halo, ORd, SRd, NReRe, C1-C3 alkyl, and C1-C3 haloalkyl;

R9 monocyclic heterocycloalkyl optionally substituted with one or more C1-C3 alkyl;

R10 is phenyl optionally substituted with one or more substituents selected from the group consisting of: halo, CN, Ra, ORb, C(O)ORc, C(O)NReRe, NReRe, NRcC(O)Rb, NRcS(O₂)Ra, SRb, S(O₂)Ra, and S(O₂)NRcRc R11 is heteroaryl optionally substituted with one or more substituents selected from the group consisting of: halo, CN, Ra, ORb, C(O)ORc, C(O)NReRe, NReRe, NRcC(O)Rb, NRcS(O₂)Ra, SRb, S(O₂)Ra, and S(O₂)NRcRc;

R12 is —OR7, —OR8, —OR9, —OR10, —OR11, —SR7, —SR8, —SR9, —SR10, or SR11;

each Ra is independently C1-C6 alkyl or C1-C6 haloalkyl;

each Rb is independently H, C1-C6 alkyl or C1-C6 haloalkyl;

each Rc is independently H or C1-C6 alkyl;

where there are two Rc groups attached to a nitrogen;

both Rc groups, independently in each instance, taken together with the nitrogen atom to which they are attached form a saturated monocyclic ring having from 5 to 7 member atoms wherein said ring optionally contains one additional heteroatom as a member atom and wherein said ring is optionally substituted with one or more substituents selected from the group consisting of: C1-C3 alkyl, ORd, and NRfRf;

each Rd is independently H, C1-C3 alkyl or C1-C3 haloalkyl;

each Re is independently H, C1-C3 alkyl, CH₂—CF₃; or both Re groups, independently in each instance, taken together with the nitrogen atom to which they are attached form a saturated monocyclic ring having from 5 to 7 member atoms wherein said ring optionally contains one additional heteroatom as a member atom and wherein said ring is optionally substituted with one or more substituents selected from the group consisting of: C1-C3 alkyl, ORd, and NRfRf;

each Rf is independently H or C1-C3 alkyl, each Rg is C3-C6 cycloalkyl optionally substituted with one or more substituents selected from the group consisting of: halo, ORd, SRd, C(O)ORc, C(O)NReRe, NReRe, and C1-C3 alkyl;

each Rh is monocyclic heterocycloalkyl optionally substituted with one or more C1-C3 alkyl;

each Ri is phenyl optionally substituted with one or more substituents selected from the group consisting of: halo, —CN, C1-C3 alkyl, C1-C3 haloalkyl, ORd, and NReRe;

each Rj is monocyclic heteroaryl optionally substituted with one or more substituents selected from the group consisting of: halo, —CN, C1-C3 alkyl, C1-C3 haloalkyl, ORd, and NReRe; and each Rk is independently H, C1-C3 alkyl, C1-C3 haloalkyl, or benzyl optionally substituted with one or more substituents selected from the group consisting of: halo, —CN, C1-C3 alkyl, C1-C3 haloalkyl, ORd, and NReRe;

or a pharmaceutically acceptable salt thereof.

2. A compound or salt according to claim 1 wherein:

A is phenyl, thiophenyl, or pyridyl;

R1 is CF₃, halo, OCF₃, CN, OC₁-C₆ alkyl, morpholino, CO₂H, or N(CH₃)₂;

x is 1, 2, or 3;

B is B1, B2 or B3;

n is 0;

Z is O;

Y is C1-C3 alkyl, phenyl, thiophenyl, or pyridyl; wherein the phenyl, thiophenyl or pyridyl may be substituted by —CO₂H, SO₂Me, CF₃, halo, or CN;

R5a is hydrogen or C1-C6 alkyl; and

R6a is hydrogen or C1-C6 alkyl;

or a pharmaceutically acceptable salt thereof.

3. A compound or salt according to claim 1 wherein:

A is phenyl;

R1 is CF₃, halo, OCF₃, CN, OC₁-C₆ alkyl, or morpholino;

x is 1, or 2;

B is B1;

n is 0

Z is O;

Y is methyl;

R5a is hydrogen; and

R6a is methyl;

or a pharmaceutically acceptable salt thereof.

4. A compound of claim 1 chosen from:

1-(4-(Methylamino)-6-{[(2R)-2-phenylpropyl]amino}-1,3,5-triazin-2-yl)-N-{[2-(trifluoromethyl)phenyl]methyl}-4-piperidinecarboxamide;

1-[4-[[2-(Dimethylamino)ethyl](methyl)amino]-6-(methylamino)-1,3,5-triazin-2-yl]-N-{[2-(trifluoromethyl)phenyl]methyl}-4-piperidinecarboxamide;

1-[4-[(1,1-Dimethylethyl)amino]-6-(4-methyl-1-piperazinyl)-1,3,5-triazin-2-yl]-N-{[2-(trifluoromethyl)phenyl]methyl}-4-piperidinecarboxamide;

1-[4-(Methylamino)-6-(4-methyl-1-piperazinyl)-1,3,5-triazin-2-yl]-N-{[2-(trifluoromethyl)phenyl]methyl}-4-piperidinecarboxamide;

1-[4-{[2-(Dimethylamino)ethyl]amino}-6-(methylamino)-1,3,5-triazin-2-yl]-N-{[2-(trifluoromethyl)phenyl]methyl}-4-piperidinecarboxamide;

N-[2-(1-Cyclohexen-1-yl)ethyl]-1-(4-(methylamino)-6-{[(2R)-2-phenylpropyl]amino}-1,3,5-triazin-2-yl)-4-piperidinecarboxamide;

1-[4-(Methylamino)-6-(4-pyridinylamino)-1,3,5-triazin-2-yl]-N-{[2-(trifluoromethyl)phenyl]methyl}-4-piperidinecarboxamide;

1-[4-(Methylamino)-6-(1-piperazinyl)-1,3,5-triazin-2-yl]-N-{[2-(trifluoromethyl)phenyl]methyl}-4-piperidinecarboxamide;

1-[4-Amino-6-(4-methyl-1-piperazinyl)-1,3,5-triazin-2-yl]-N-{[2-(trifluoromethyl)phenyl]methyl}-4-piperidinecarboxamide;

1-[4-(Methylamino)-1,3,5-triazin-2-yl]-N-{[2-(trifluoromethyl)phenyl]methyl}-4-piperidinecarboxamide;

1-(4-{[(2R)-2-Phenylpropyl]amino}-1,3,5-triazin-2-yl)-N-{[2-(trifluoromethyl)phenyl]methyl}-4-piperidinecarboxamide;

1-[4-({2-[(Phenylmethyl)thio]ethyl}amino)-1,3,5-triazin-2-yl]-N-{[2-(trifluoromethyl)phenyl]methyl}-4-piperidinecarboxamide;

1-[4-(4-Methyl-1-piperazinyl)-1,3,5-triazin-2-yl]-N-{[2-(trifluoromethyl)phenyl]methyl}-4-piperidinecarboxamide;

1-[4-(4-Morpholinyl)-1,3,5-triazin-2-yl]-N-{[2-(trifluoromethyl)phenyl]methyl}-4-piperidinecarboxamide;

1-[4,6-Bis(4-methyl-1-piperazinyl)-1,3,5-triazin-2-yl]-N-{[2-(trifluoromethyl)phenyl]methyl}-4-piperidinecarboxamide;

1-(4,6-Bis{[(2R)-2-phenylpropyl]amino}-1,3,5-triazin-2-yl)-N-{[2-(trifluoromethyl)phenyl]methyl}-4-piperidinecarboxamide;

1-{4,6-Bis[[2-(dimethylamino)ethyl](methyl)amino]-1,3,5-triazin-2-yl}-N-{[2-(trifluoromethyl)phenyl]methyl}-4-piperidinecarboxamide;

1-(4,6-Dihexahydro-1H-azepin-1-yl-1,3,5-triazin-2-yl)-N-{[2-(trifluoromethyl)phenyl]methyl}-4-piperidinecarboxamide;

1-[4,6-Bis(methylamino)-1,3,5-triazin-2-yl]-N-{[2-(trifluoromethyl)phenyl]methyl}-4-piperidinecarboxamide;

1-[4-Hydroxy-6-(4-methyl-1-piperazinyl)-1,3,5-triazin-2-yl]-N-{[2-(trifluoromethyl)phenyl]methyl}-4-piperidinecarboxamide;

1-[4-(Methoxy)-6-(4-methyl-1-piperazinyl)-1,3,5-triazin-2-yl]-N-{[2-(trifluoromethyl)phenyl]methyl}-4-piperidinecarboxamide;

1-[4-(4-Methyl-1-piperazinyl)-6-(methylthio)-1,3,5-triazin-2-yl]-N-{[2-(trifluoromethyl)phenyl]methyl}-4-piperidinecarboxamide;

1-[4-[(1-Methylethyl)amino-6-(4-methyl-1-piperazinyl)-1,3,5-triazin-2-yl]-N-{[2-(trifluoromethyl)phenyl]methyl}-4-piperidinecarboxamide;

N-[(2,4-Dichlorophenyl)methyl]-1-[4-(methylamino)-6-(4-methyl-1-piperazinyl)-1,3,5-triazin-2-yl]-4-piperidinecarboxamide;

1-[4-(Methylamino)-6-(4-methyl-1-piperazinyl)-1,3,5-triazin-2-yl]-N-{[4-(trifluoromethyl)phenyl]methyl}-4-piperidinecarboxamide;

1-[4-(Methylamino)-6-(4-methyl-1-piperazinyl)-1,3,5-triazin-2-yl]-N-({2-[(trifluoromethyl)oxy]phenyl}methyl)-4-piperidinecarboxamide;

N-[(2-Chlorophenyl)methyl]-1-[4-(methylamino)-6-(4-methyl-1-piperazinyl)-1,3,5-triazin-2-yl]-4-piperidinecarboxamide;

N-(Cyclohexylmethyl)-1-[4-(methylamino)-6-(4-methyl-1-piperazinyl)-1,3,5-triazin-2-yl]-4-piperidinecarboxamide;

1-[4-(Methylamino)-6-(4-methyl-1-piperazinyl)-1,3,5-triazin-2-yl]-N-(2-pyridinylmethyl)-4-piperidinecarboxamide;

N-[2-Trifluoro-phenyl)methyl)-benzyl]-1-[4-(methylamino)-6-(4-methyl-1-piperazinyl)-1,3,5-triazin-2-yl]-3-piperidinecarboxamide;

1-[4-(Methylamino)-6-(4-methyl-1-piperazinyl)-1,3,5-triazin-2-yl]-N-({2-[(trifluoromethyl)oxy]phenyl}methyl)-3-piperidinecarboxamide;

N-[(2,4-Dichlorophenyl)methyl]-1-[4-(methylamino)-6-(4-methyl-1-piperazinyl)-1,3,5-triazin-2-yl]-3-piperidinecarboxamide;

1-[4-(Methylamino)-6-(4-methyl-1-piperazinyl)-1,3,5-triazin-2-yl]-N-{[2-(trifluoromethyl)phenyl]methyl}-3-pyrrolidinecarboxamide;

1-[4-(Methylamino)-6-(4-methyl-1-piperazinyl)-1,3,5-triazin-2-yl]-N-({2-[(trifluoromethyl)oxy]phenyl}methyl)-3-pyrrolidinecarboxamide;

2-{4-[4-(Methylamino)-6-(4-methyl-1-piperazinyl)-1,3,5-triazin-2-yl]-1-piperazinyl}-N-({2-[(trifluoromethyl)oxy]phenyl}methyl)acetamide;

2-{4-[4-(Methylamino)-6-(4-methyl-1-piperazinyl)-1,3,5-triazin-2-yl]-1-piperazinyl}-N-{[2-(trifluoromethyl)phenyl]methyl}acetamide;

N-[(2,4-Dichlorophenyl)methyl]-2-{4-[4-(methylamino)-6-(4-methyl-1-piperazinyl)-1,3,5-triazin-2-yl]-1-piperazinyl}acetamide;

4-[4-(Methylamino)-6-(4-methyl-1-piperazinyl)-1,3,5-triazin-2-yl]-N-{[2-(trifluoromethyl)phenyl]methyl}-1-piperazinecarboxamide;

4-[4-(Methylamino)-6-(4-methyl-1-piperazinyl)-1,3,5-triazin-2-yl]-N-({2-[(trifluoromethyl)oxy]phenyl}methyl)-1-piperazinecarboxamide;

1-[4-(Methylamino)-6-(2-methylphenyl)-1,3,5-triazin-2-yl]-N-{[2-(trifluoromethyl)phenyl]methyl}-4-piperidinecarboxamide;

1-{4-(Methylamino)-6-[4-(trifluoromethyl)phenyl]-1,3,5-triazin-2-yl}-N-{[2-(trifluoromethyl)phenyl]methyl}-4-piperidinecarboxamide;

1-[4-[4-(Acetylamino)phenyl]-6-(methylamino)-1,3,5-triazin-2-yl]-N-{[2-(trifluoromethyl)phenyl]methyl}-4-piperidinecarboxamide;

1-[4-[4-(Dimethylamino)phenyl]-6-(methylamino)-1,3,5-triazin-2-yl]-N-{[2-(trifluoromethyl)phenyl]methyl}-4-piperidinecarboxamide;

1-{4-(Methylamino)-6-[3-(trifluoromethyl)phenyl]-1,3,5-triazin-2-yl}-N-{[2-(trifluoromethyl)phenyl]methyl}-4-piperidinecarboxamide;

1-[4-(2-Chlorophenyl)-6-(methylamino)-1,3,5-triazin-2-yl]-N-{[2-(trifluoromethyl)phenyl]methyl}-4-piperidinecarboxamide;

1-[4-(3-Chlorophenyl)-6-(methylamino)-1,3,5-triazin-2-yl]-N-{[2-(trifluoromethyl)phenyl]methyl}-4-piperidinecarboxamide;

1-[4-(3-Fluorophenyl)-6-(methylamino)-1,3,5-triazin-2-yl]-N-{[2-(trifluoromethyl)phenyl]methyl}-4-piperidinecarboxamide;

1-[4-(4-Fluorophenyl)-6-(methylamino)-1,3,5-triazin-2-yl]-N-{[2-(trifluoromethyl)phenyl]methyl}-4-piperidinecarboxamide;

1-(4-(Methylamino)-6-[2-(methoxy)phenyl]-1,3,5-triazin-2-yl)-N-{[2-(trifluoromethyl)phenyl]methyl}-4-piperidinecarboxamide;

1-[4-[2,4-Bis(methoxy)phenyl]-6-(methylamino)-1,3,5-triazin-2-yl]-N-{[2-(trifluoromethyl)phenyl]methyl}-4-piperidinecarboxamide;
1-[4-(2,6-Dimethylphenyl)-6-(methylamino)-1,3,5-triazin-2-yl]-N-{[2-(trifluoromethyl)phenyl]methyl}-4-piperidinecarboxamide;
1-{4-(Methylamino)-6-[3-(methoxy)phenyl]-1,3,5-triazin-2-yl}-N-{[2-(trifluoromethyl)phenyl]methyl}-4-piperidinecarboxamide;
1-[4-[4-(Ethoxy)phenyl]-6-(methylamino)-1,3,5-triazin-2-yl]-N-{[2-(trifluoromethyl)phenyl]methyl}-4-piperidinecarboxamide;
1-(4-(Methylamino)-6-{3-[(trifluoromethyl)oxy]phenyl}-1,3,5-triazin-2-yl)-N-{[2-(trifluoromethyl)phenyl]methyl}-4-piperidinecarboxamide;
1-(4-(Methylamino)-6-{4-[(trifluoromethyl)oxy]phenyl}-1,3,5-triazin-2-yl)-N-{[2-(trifluoromethyl)phenyl]methyl}-4-piperidinecarboxamide;
1-[4-[3-Chloro-4-(ethoxy)phenyl]-6-(methylamino)-1,3,5-triazin-2-yl]-N-{[2-(trifluoromethyl)phenyl]methyl}-4-piperidinecarboxamide;
1-[4-[3-(Dimethylamino)phenyl]-6-(methylamino)-1,3,5-triazin-2-yl]-N-{[2-(trifluoromethyl)phenyl]methyl}-4-piperidinecarboxamide;
1-[4-(Methylamino)-6-(3-pyridinyl)-1,3,5-triazin-2-yl]-N-{[2-(trifluoromethyl)phenyl]methyl}-4-piperidinecarboxamide;
1-[4-(Methylamino)-6-(4-pyridinyl)-1,3,5-triazin-2-yl]-N-{[2-(trifluoromethyl)phenyl]methyl}-4-piperidinecarboxamide;
1-{4-(Methylamino)-6-[4-(methoxy)phenyl]-1,3,5-triazin-2-yl}-N-{[2-(trifluoromethyl)phenyl]methyl}-4-piperidinecarboxamide;
1-{4-(Methylamino)-6-[3-(methyloxy)phenyl]-1,3,5-triazin-2-yl}-N-{[2-(trifluoromethyl)phenyl]methyl}-4-piperidinecarboxamide;
1-[4-[4-(Ethoxy)phenyl]-6-(methylamino)-1,3,5-triazin-2-yl]-N-{[2-(trifluoromethyl)phenyl]methyl}-4-piperidinecarboxamide;
1-[4-(3-Cyanophenyl)-6-(methylamino)-1,3,5-triazin-2-yl]-N-{[2-(trifluoromethyl)phenyl]methyl}-4-piperidinecarboxamide;
1-[4-(4-Cyanophenyl)-6-(methylamino)-1,3,5-triazin-2-yl]-N-{[2-(trifluoromethyl)phenyl]methyl}-4-piperidinecarboxamide;
1-{4-(Methylamino)-6-[4-(methylsulfonyl)phenyl]-1,3,5-triazin-2-yl}-N-{[2-(trifluoromethyl)phenyl]methyl}-4-piperidinecarboxamide;
1-[4-[4-(Ethylsulfonyl)phenyl]-6-(methylamino)-1,3,5-triazin-2-yl]-N-{[2-(trifluoromethyl)phenyl]methyl}-4-piperidinecarboxamide;
1-[4-(2-Fluorophenyl)-6-(methylamino)-1,3,5-triazin-2-yl]-N-{[2-(trifluoromethyl)phenyl]methyl}-4-piperidinecarboxamide;
1-(4-(Methylamino)-6-{4-[(trifluoromethyl)oxy]phenyl}-1,3,5-triazin-2-yl)-N-{[2-(trifluoromethyl)phenyl]methyl}-4-piperidinecarboxamide;
1-(4-(Methylamino)-6-{3-[(trifluoromethyl)oxy]phenyl}-1,3,5-triazin-2-yl)-N-{[2-(trifluoromethyl)phenyl]methyl}-4-piperidinecarboxamide;
1-[4-Methyl-6-(methylamino)-1,3,5-triazin-2-yl]-N-{[2-(trifluoromethyl)phenyl]methyl}-4-piperidinecarboxamide;
1-(4-Amino-6-methyl-1,3,5-triazin-2-yl)-N-{[2-(trifluoromethyl)phenyl]methyl}-4-piperidinecarboxamide
1-[4-Ethyl-6-(4-methyl-1-piperazinyl)-1,3,5-triazin-2-yl]-N-{[2-(trifluoromethyl)phenyl]methyl}-4-piperidinecarboxamide;
1-[4-Ethyl-6-(4-morpholinyl)-1,3,5-triazin-2-yl]-N-{[2-(trifluoromethyl)phenyl]methyl}-4-piperidinecarboxamide;
1-(4-Amino-6-ethyl-1,3,5-triazin-2-yl)-N-{[2-(trifluoromethyl)phenyl]methyl}-4-piperidinecarboxamide
1-[4-Amino-6-(1-methylethyl)-1,3,5-triazin-2-yl]-N-{[2-(trifluoromethyl)phenyl]methyl}-4-piperidinecarboxamide;
1-[4-Amino-6-(2-methylpropyl)-1,3,5-triazin-2-yl]-N-{[2-(trifluoromethyl)phenyl]methyl}-4-piperidinecarboxamide;
1-(4-Amino-6-phenyl-1,3,5-triazin-2-yl)-N-{[2-(trifluoromethyl)phenyl]methyl}-4-piperidinecarboxamide;
1-[4-Ethyl-6-(methylamino)-1,3,5-triazin-2-yl]-N-{[2-(trifluoromethyl)phenyl]methyl}-4-piperidinecarboxamide;
N-[(4-Chlorophenyl)methyl]-1-[4-(methylamino)-6-phenyl-1,3,5-triazin-2-yl]-4-piperidinecarboxamide
1-[4-(Methylamino)-6-phenyl-1,3,5-triazin-2-yl]-N-[(2,4,6-trimethylphenyl)methyl]-4-piperidinecarboxamide;
N-[(2,4-Dichlorophenyl)methyl]-1-[4-(methylamino)-6-phenyl-1,3,5-triazin-2-yl]-3-piperidinecarboxamide;
1-[4-(Methylamino)-6-phenyl-1,3,5-triazin-2-yl]-N-{[2-(trifluoromethyl)phenyl]methyl}-3-piperidinecarboxamide;
1-[4-(Methylamino)-6-phenyl-1,3,5-triazin-2-yl]-N-{[2-(trifluoromethyl)phenyl]methyl}-4-piperidinecarboxamide;
1-[4-(Methylamino)-6-(3-thienyl)-1,3,5-triazin-2-yl]-N-{[2-(trifluoromethyl)phenyl]methyl}-4-piperidinecarboxamide;
1-[4-[4-(1,1-Dimethylethyl)phenyl]-6-(methylamino)-1,3,5-triazin-2-yl]-N-{[2-(trifluoromethyl)phenyl]methyl}-4-piperidinecarboxamide;
N-{[4-cyano-2-(trifluoromethyl)phenyl]methyl}-1-[4-methyl-6-(methylamino)-1,3,5-triazin-2-yl]-4-piperidinecarboxamide;
1-[4-methyl-6-(methylamino)-1,3,5-triazin-2-yl]-N-({2-[(trifluoromethyl)thio]phenyl}methyl)-4-piperidinecarboxamide;
1-[4-methyl-6-(methylamino)-1,3,5-triazin-2-yl]-N-({2-[(trifluoromethyl)thio]phenyl}methyl)-4-piperidinecarboxamide;
1-[4-methyl-6-(methylamino)-1,3,5-triazin-2-yl]-N-{[4-(methyloxy)-2-(trifluoromethyl)phenyl]methyl}-4-piperidinecarboxamide;
N-[(2,4-dichlorophenyl)methyl]-1-{4-[(2-hydroxyethyl)amino]-6-methyl-1,3,5-triazin-2-yl}-4-piperidinecarboxamide;
N-({4-bromo-2-[(trifluoromethyl)oxy]phenyl}methyl)-1-[4-methyl-6-(methylamino)-1,3,5-triazin-2-yl]-4-piperidinecarboxamide; and
N-{[4-fluoro-2-(trifluoromethyl)phenyl]methyl}-1-[4-methyl-6-(methylamino)-1,3,5-triazin-2-yl]-4-piperidinecarboxamide;

or a pharmaceutically acceptable salt thereof.

5. A compound of claim 1 which is -[(trifluoromethyl)oxy]phenyl}methyl)-1-[4-methyl-6-(methylamino)-1,3,5-triazin-2-yl]-4-piperidinecarboxamide; or a pharmaceutically acceptable salt thereof.

6. A pharmaceutical composition comprising a compound or salt according to claim 1 and one or more pharmaceutically-acceptable excipient.

7. A method for treating hypertension, heart failure, peripheral vascular disease, coronary artery disease, myocardial ischemia, and angina comprising administering a safe and effective amount of a compound or salt according to claim 1 to a human in need thereof.

8. A method for treating renal or liver failure comprising administering a safe and effective amount of a compound or salt according to claim 1 to a human in need thereof.

9. A method for treating COPD and asthma comprising administering a safe and effective amount of a compound or salt according to claim 1 to a human in need thereof.

10. A method for treating glucose intolerance, insulin insensitivity, diabetes and obesity comprising administering a safe and effective amount of a compound or salt according to claim 1 to a human in need thereof.

11. A method according to claim 7 wherein the compound is administered orally.

12. A method according to claim 7 wherein the compound is administered intravenously.

13. A method according to claim 7 wherein the compound is administered by inhalation.

14. A method according to claim 9 wherein the compound is administered orally.

15. A method according to claim 9 wherein the compound is administered intravenously.

16. A method according to claim 9 wherein the compound is administered by inhalation.

* * * * *